(12) United States Patent
Brewer

(10) Patent No.: US 7,416,741 B2
(45) Date of Patent: Aug. 26, 2008

(54) COPPER LOWERING TREATMENT OF INFLAMMATORY AND FIBROTIC DISEASES

(75) Inventor: George J. Brewer, Ann Arbor, MI (US)

(73) Assignee: The Regents of the University of Michigan, Ann Arbor, MI (US)

(*) Notice: Subject to any disclaimer, the term of this patent is extended or adjusted under 35 U.S.C. 154(b) by 597 days.

(21) Appl. No.: 11/057,353

(22) Filed: Feb. 14, 2005

(65) Prior Publication Data

US 2005/0147694 A1 Jul. 7, 2005

Related U.S. Application Data

(63) Continuation of application No. 10/444,204, filed on May 23, 2003, now Pat. No. 6,855,340.

(60) Provisional application No. 60/382,993, filed on May 24, 2002.

(51) Int. Cl.
*A01N 59/20* (2006.01)
*A61K 33/34* (2006.01)
*A61K 31/30* (2006.01)

(52) U.S. Cl. ............... 424/630; 424/637; 424/646; 514/499

(58) Field of Classification Search ............... 424/630, 424/637, 646; 514/499
See application file for complete search history.

(56) References Cited

U.S. PATENT DOCUMENTS

| | | | |
|---|---|---|---|
| 4,678,667 A | 7/1987 | Meares et al. ............... 424/85 |
| 4,762,705 A | 8/1988 | Rubin ............... 424/85 |
| 4,766,226 A | 8/1988 | Hill et al. ............... 556/18 |
| 4,952,607 A | 8/1990 | Sorenson et al. ............... 514/589 |
| 5,057,302 A | 10/1991 | Johnson et al. ............... 424/1 |
| 5,100,885 A | 3/1992 | Abrams et al. ............... 54/184 |
| 5,169,858 A | 12/1992 | Rubin ............... 514/365 |
| 5,385,933 A | 1/1995 | Rabinovitz et al. ............... 514/499 |
| 5,512,559 A | 4/1996 | Skalkos et al. ............... 514/185 |
| 5,563,132 A | 10/1996 | Bodaness ............... 514/185 |
| 5,565,491 A | 10/1996 | Schieven ............... 514/492 |
| RE35,458 E | 2/1997 | Azuara ............... 556/16 |
| 6,323,218 B1 | 11/2001 | Bush et al. |
| 6,951,890 B2 | 10/2005 | Cooper et al. |

OTHER PUBLICATIONS

Kumaratilake et al, Intravenously administered tetrathiomolybate and the removal of copper for the liver of copper loaded sheep, J. of Comparative Patholoaht, 1989, 101 (2), 177-99. (ABS only).*
Brewer, Current Opinion in Chemical Biology 7:207-212 (2003).
Sparks et al., PNAS 100:11065-11069 (2003).
DR Brigstock, Endocr. Rev., 20(2):189-206 [1999].
RK Coker and GJ Laurent, Thorax., 52(3):294-296 [1997].
SH Phan, Thorax., 50(4):415-421 [1995].
WA Border and NA Noble, N. Engl. J. Med., 331(19):1286-1292 [1994].
JT Allen et al., Cell Mol. Biol., 21:693-700 [1999].
JF Pittet et al., J. Clin. Invest., 107:537-1544 [2001].
SH Phan and SL Kunkel, Exp. Lung. Res., 18:29-43 [1992].
GJ Brewer, PSEBM, 223(1):39-49 [2000].
GJ Brewer, Soc. for Exp. Biol. and Med., 226:665-673 [2001].
K Hsiao, Exp. Gerontol., 33:883-889 [1998].
C Sturchler-Pierrat et al., Proc. Natl. Acad. Sci. USA, 94:13287-13292 [1997].
TP Wong et al., J. Neurosci., 19:2706-2716 [1999].
GJ Brewer et al., Clin. Cancer., 6:1-10 [2000].
C Cox et al., Laryngoscope 111:696-701 [2001].
K van Golen et al., Neoplasia, 4(5):373-379 [2002].
Mills et al., J. Inorg. Biochem., 14:189 [1981].
Mills et al., J. Inorg. Biochem., 14:163 [1981].
Bremmer et al., J. Inorg. Biochem., 16:109 [1982].
Brewer et al., Arch. Neurol., 51(6):545-554 [1994].
Brewer et al., Arch. Neurol., 53:1017-1025 [1996].
GJ Brewer and Yuzbasiyan-Gurkan, Medicine, 71(3):139-164 [1992].
Hill et al., Hepatology, 7:522-528 [1987].
Brewer et al. (1987) J. Lab. Clin. Med. 109:526-531.
Brewer et al. (1987) Proc. Soc. Exper. Biol. Med. 7:446-455.
Brewer et al. (1987) Sem. Neurol. 7:209-220.
Yuzbasiyan-Gurkan et al. (1989) J. Lab. Clin. Med. 114:520-526.
Brewer et al. (1989) J. Lab. Clin. Med. 114:633-638.
Lee et al. (1989) J. Lab. Clin. Med. 114:639-645.
Brewer et al. (1991) J. Lab. Clin. Med. 118:466-470.
G Yuzbasiyan-Gurkan et al., J. Lab. Clin. Med., 120:380-386 [1992].
GJ Brewer et al., J. Lab. Clin. Med., 123:849-858 [1993].

(Continued)

*Primary Examiner*—Alton Pryor
(74) *Attorney, Agent, or Firm*—Casimir Jones, S.C.

(57) ABSTRACT

The present invention relates generally to the field of prophylaxis and therapy for inflammatory and/or fibrotic diseases which include responses to injuries. In particular, the present invention is related to agents that can bind or complex copper such as thiomolybdate, and to the use of these agents in the prevention and treatment of inflammatory and/or fibrotic diseases. Exemplary thiomolybdates include mono-, di-, tri- and tetrathiomolybdate; these agents are administered to patients to prevent and/or treat inflammatory and/or fibrotic diseases, such as pulmonary disease including pulmonary fibrosis and acute respiratory distress syndrome, liver disease including liver cirrhosis and hepatitis C, kidney disease including renal interstitial fibrosis, scleroderma, cystic fibrosis, pancreatic fibrosis, keloid, secondary fibrosis in the gastrointestinal tract, hypertrophic burn scars, myocardial fibrosis, Alzheimer's disease, retinal detachment inflammation and/or fibrosis resulting after surgery, and graft versus host and host versus graft rejections.

13 Claims, 13 Drawing Sheets

OTHER PUBLICATIONS

Hoogenraad et al., Lancet, 2:1262-1263 [1978].
Hoogenraad et al., Eur. Neurol., 18:205-211 [1979].
Hoogenraad et al., J. Neurol. Sci., 77:137-146 [1987].
GJ Brewer et al., Arch. Neurol., 44:490-494 [1987].
Glass et al., Arch. Neurol., 47:595-596 [1990].
GJ Brewer et al., Arch. Neurol., 51:304-305 [1994].
Gooneratne et al., Br. J. Nutr., 46:469 [1981].
Gooneratne et al., Br. J. Nutr., 46:457 [1981].
GP Lim et al., J. Neurosci., 20:5709-5714 [2000].
SS Brem et al., Am. J. Path., 137:1121-1147 [1990].
SS Brem et al., Neurosurgery, 26:391-396 [1990].
Q Pan et al., Cancer Res., 62:4854-4859 [2002].
KR Bales et al., Nature Genet., 17:263-264 [1997].
DM Holtzman et al., Proc. Natl. Acad. Sci. USA, 97:2892-2897 [2000].
T Wyss-Coray et al., Nature, 389:603-606 [1997].
L Helmuth, Science, 1273-274 [2000].
KH Schosinsky et al., Clin. Chem., 20(12):1556-1563 [1974].
J Gau et al., Amer. J. Pathology, 160(2):731-738 [2002].
JQ Trojanowski, Amer. J. Pathology, 160(2):409-411 [2002].
GJ Brewer et al., Annals. Int. Med., 99:314-320 [1983].
Walshe, Lancet, 1:643-647 [1982].
Yoshida et al., Neurosurgery 37(2):287-292 (1995).
Bremner and Young, Br. J. Nutr., 39:325 [1978].
Harper and Walshe, Br. J. Hematol., 64:854-8 [1986].
Young et al., Neurol., 36:244-249 [1986]).
Walshe, Am. J. Med., 21:487 [1956].
Suzuki et al., Toxic, 83:149 [1993].
Wu et al., Nat. Genet., 7:541 [1994].
Mason et al., J. Inorg. Biochem., 19:153 [1983].
Hynes et al., Brit. J. Nutr., 52:149 [1984].
DJ Selkoe, Nature, 399 suppl:A23-31 [1999].
KS Raju et al., J. Natl. Cancer Inst., 69:1183-1188 [1982].
M Neuman et al., J. Gastro. and Hepat., 17:196-202 [2002].
Humphries et al., Vet. Record, 119:596-598 [1986].
Humphries et al., Vet. Record, 123:51-53 [1988].
Brem et al., Proceeding of the American Associationf or Cancer Research, 33:76 Abstract 455 (1992).
M. Khan et al., Neoplasia 4(2):1-7 [2002(.

* cited by examiner

COPPER LOWERING TREATMENT OF INFLAMMATORY AND FIBROTIC DISEASES

The present application is a continuation of patent application Ser. No. 10/444,204, filed May 23, 2003, now U.S. Pat. No. 6,855,340 which claims priority to U.S. provisional application Ser. No. 60/382,993, filed on May 24, 2002, the disclosures of which are herein incorporated by reference in their entireties.

FIELD OF THE INVENTION

The present invention relates generally to the field of prophylaxis and therapy for inflammatory and fibrotic diseases. In particular, the present invention is related to agents that can bind or complex copper, and to the use of these agents in the prevention and treatment of inflammatory and fibrotic diseases.

BACKGROUND

Many diseases begin with inflammation, which if excessive, may overwhelm and kill the patient, or if the patient survives, often leads to a disabling fibrosis, which ultimately may also kill the patient.

A classic example is ARDS (Acute Respiratory Distress Syndrome) which may be initiated by any one of several lung injuries (smoke inhalation, near drowning, some infections, etc.). About one third of these patients die, overwhelmed by inflammatory processes in the lung. In those patients that don't die, there is a high risk of developing interstitial pulmonary fibrosis, which is itself often a progressive and fatal disease. A similar pattern is seen in inflammatory diseases of the liver (such as hepatitis C) which lead to cirrhosis, in inflammatory diseases of the kidney, such as glomerulonephritis, which lead to glomerulosclerosis and renal interstitial fibrosis, and in diseases of the skin, leading to systemic sclerosis (scleroderma). Other diseases with similar patterns include pancreatic fibrosis, bowel inflammations leading to fibrosis and obstruction, and acute burn multiple organ damage.

Recently, evidence has been accumulating that the common condition of inflammation may also underlie many other chronic and debilitating diseases, such as Alzheimer's, heart disease, osteoporosis and diabetes, and that drugs that fight inflammation may have a role in preventing or delaying those diseases, or at least slowing them down. Typically, anti-inflammatory drugs belong to the class of drugs known as nonsteroidal anti-inflammatory drugs (NSAIDS), which include ibuprofen and naproxen, aspirin, and prescription drugs known as cox-2-inhibitors, including celecoxib (Celebrex) and rofecoxib (Vioxx) as well as diclofenac (Voltaren), indomethacin (Indocin), and other less commonly used drugs. However, patients at risk for these common and chronic diseases are not encouraged to take anti-inflammatory drugs, other than aspirin, at least in part because regular use of these drugs is not safe for everyone. Side effects can include stomachache or nausea in up to 20 percent of patients, and stomach or intestinal ulcers and bleeding in 2 percent to 4 percent of those who take the drugs for a year, especially for people over 60. The stomach bleeding can occur with little warning, and it can be fatal. Even low doses of aspirin can cause stomach bleeding in some people, and it can also cause a slight increase in the risk of a less common type of stroke, also brought on by cerebral hemorrhage. Anti-inflammatory drugs may make kidney disease worse, and cox-2 drugs have been suggested to cause an increase in the risk of heart attack.

Currently there is no effective therapy for these inflammatory and/or fibrotic diseases. Moreover, anti-inflammatory drugs possess high levels of risk, especially with prolonged use. Thus, what is needed is an effective therapy for inflammatory and/or fibrotic disease; preferably, such therapy is also safe, especially for long-term use.

SUMMARY OF THE INVENTION

The present invention provides an effective and safe therapy for inflammatory and fibrotic diseases, which include response to injury. This is accomplished by treating patients suffering from such diseases with agents which reduce the level of endogenous copper; in some embodiments, this is accomplished by treating patients with agents which complex or bind copper, which for some agents may result in the formation of a tripartite agent-copper-protein complex, thus decreasing endogenous copper levels. Effective agents include but are not limited to copper binding or complexing thiomolybdates. The compositions and methods of the present invention result in effective therapy without the side effects and risks associated with anti-inflammatory drugs, and without the side effects and risks associated with other copper reducing agents.

The present invention provides a method of treating inflammatory or fibrotic disease in a patient, comprising administering to the patient having an inflammatory or fibrotic disease a biologically effective amount of at least a first agent that binds or complexes copper. In some embodiments, the first agent is a thiomolybdate; in other embodiments, the thiomolybdate forms a thiomolybdate-copper-protein complex in a patient. In yet other embodiments, the thiomolybdate is tetrathiomolybdate. In some embodiments, the patient is a human; in other embodiments, the patient is a non-human animal. In some embodiments, the biologically effective amount of the first agent is between about 20 mg and about 200 mg per patient. In some embodiments, administering the first agent lowers endogenous copper levels; in other embodiments, administering the first agent lowers serum ceruloplasmin levels. In some embodiments, the first agent is administered orally. In other embodiments, the first agent is administered by injection; in further embodiments, the injection is chosen from intravascular, intramuscular, or subcutaneous injection.

The present invention also provides a method of treating inflammatory and/or fibrotic disease in a patient, comprising administering to the patient having an inflammatory and/or fibrotic disease a therapeutically effective amount of at least a first agent that binds or complexes copper. In some embodiments, the first agent is a thiomolybdate. In further embodiments, the thiomolybdate forms a thiomolybdate-copper-protein complex in a patient. In yet other embodiments, the thiomolybdate is tetrathiomolybdate. In some embodiments, the patient is a human; in other embodiments, the patient is a non-human animal. In some embodiments, the therapeutically effective amount of the first agent is between about 20 mg and 200 mg per patient administered over a therapeutically effective time or period. In other embodiments, the therapeutically effective amount of the first agent is between about 20 mg and 200 mg per patient per day. In some embodiments, administering the first agent lowers endogenous copper levels; in further embodiments, administering the first agent lowers serum ceruloplasmin levels. In some embodiments, the first agent is administered orally. In other embodiments, the first agent is administered by injection; in further embodiments, the injection is chosen from intravascular, intramuscular, or subcutaneous injection.

In any of the embodiments described above, the inflammatory or fibrotic disease can be chosen from pulmonary disease including pulmonary fibrosis and acute respiratory distress syndrome, liver disease including liver cirrhosis and hepatitis C, kidney disease including renal interstitial fibrosis, scleroderma, cystic fibrosis, pancreatic fibrosis, keloid, secondary fibrosis in the gastrointestinal tract, hypertrophic burn scars, myocardial fibrosis, Alzheimer's disease, retinal detachment inflammation and/or fibrosis resulting after surgery, and graft versus host and host versus graft rejections.

The present invention also provides any of the embodiments described above, where the method further comprises administering to the patient a therapeutically effective amount of at least a second agent, where the second agent is chosen from anti-inflammatory agents, anti-fibrotic agents, and anti-angiogenesis agents. In some of these embodiments, the second agent is chosen from a steroid, a NSAIDS (non-steroidal anti-inflammatory drugs), a chemotherapeutic agent as used in some auto-immune diseases, and an antibody or antisense agent directed to specific cytokines or to cytokine receptors or to other molecules which enhance inflammation and/or fibrosis.

The present invention also provides a method of prophylactic or therapeutic intervention in a patient at risk of developing an inflammatory and/or fibrotic disease, comprising administering to the patient at risk for developing an inflammatory and/or fibrotic disease a biologically effective amount of at least a first agent that binds or complexes copper. In some embodiments, the first agent is a thiomolybdate; in other embodiments, the thiomolybdate forms a thiomolybdate-copper-protein complex in a patient. In yet other embodiments, the thiomolybdate is tetrathiomolybdate. In some embodiments, the patient is a human; in other embodiments, the patient is a non-human animal. In some embodiments, the biologically effective amount of the first agent is between about 20 mg and about 200 mg per patient. In some embodiments, administering the first agent lowers endogenous copper levels; in other embodiments, administering the first agent lowers serum ceruloplasmin levels. In some embodiments, the first agent is administered orally. In other embodiments, the first agent is administered by injection; in further embodiments, the injection is chosen from intravascular, intramuscular, or subcutaneous injection. In yet other embodiments, the method further comprises administering to the patient a therapeutically effective amount of at least a second agent, where the second agent is chosen from anti-inflammatory agents, anti-fibrotic agents, and anti-angiogenesis agents. In some of these embodiments, the second agent is chosen from a steroid, a NSAIDS (non-steroidal anti-inflammatory drugs), a chemotherapeutic agent as used in some auto-immune diseases, and an antibody or antisense agent directed to specific cytokines or to cytokine receptors or to other molecules which enhance inflammation and/or fibrosis.

The present invention also provides a composition comprising a combined therapeutic amount of at least a first agent that binds or complexes copper and at least a second agent, where the second agent is chosen from anti-inflammatory agents, anti-fibrotic agents, and anti-angiogenesis agents. In some embodiments, the first agent is a thiomolybdate; in some further embodiments, the thiomolybdate is tetrathiomolybdate. In other embodiments, the second agent is chosen from a steroid, a NSAIDS (non-steroidal anti-inflammatory drugs), a chemotherapeutic agent as used in some auto-immune diseases, and an antibody or antisense agent directed to specific cytokines or to cytokine receptors or to other molecules which enhance inflammation and/or fibrosis.

The present invention also provides a therapeutic kit comprising, in at least a first suitable container, a therapeutically effective combined amount of at least a first agent that binds or complexes copper, and at least a second agent, where the second agent is chosen from anti-inflammatory agents, anti-fibrotic agents, and anti-angiogenesis agents. In some embodiments, the first agent is a thiomolybdate; in some further embodiments, the thiomolybdate is a tetrathiomolybdate. In other embodiments, the second agent is chosen from a steroid, a NSAIDS (non-steroidal anti-inflammatory drugs), a chemotherapeutic agent as used in some auto-immune diseases, and an antibody or antisense agent directed to specific cytokines or to cytokine receptors or to other molecules which enhance inflammation and/or fibrosis. In yet other embodiments, the kit further comprises appropriate instructions and labels for use of the agents.

The agents for use in the present invention, such as copper binding or complexing thiomolybdates, of which tetrathiomolybdate is an example, lower endogenous copper levels; although it is not necessary to understand the mechanism of these agents, and the invention is not intended to be limited to any particular mechanism, it is contemplated that in some embodiments, the agents lower endogenous copper levels by forming a "tripartite agent-copper-protein complex" that is subsequently cleared from the body. The copper bound in these "tripartite agent-copper-protein complex" is not reversibly released from these complexes, and are thus distinguished from reversible bipartite copper chelation.

The present invention further provides method and compositions for treating an inflammatory diseases in a patient, comprising administering to the patient having an inflammatory disease a biologically effective amount of at least a first agent that binds or complexes copper, under conditions such that the level of at least one inflammatory cytokine in the patient is reduced. In some of these embodiments, the inflammatory cytokine comprises TNFα; in other embodiments, the inflammatory cytokine comprises Il-1β. The present invention is not limited however to providing methods and compositions that lower the levels of the aforementioned cytokines.

DEFINITIONS

Figure 1:
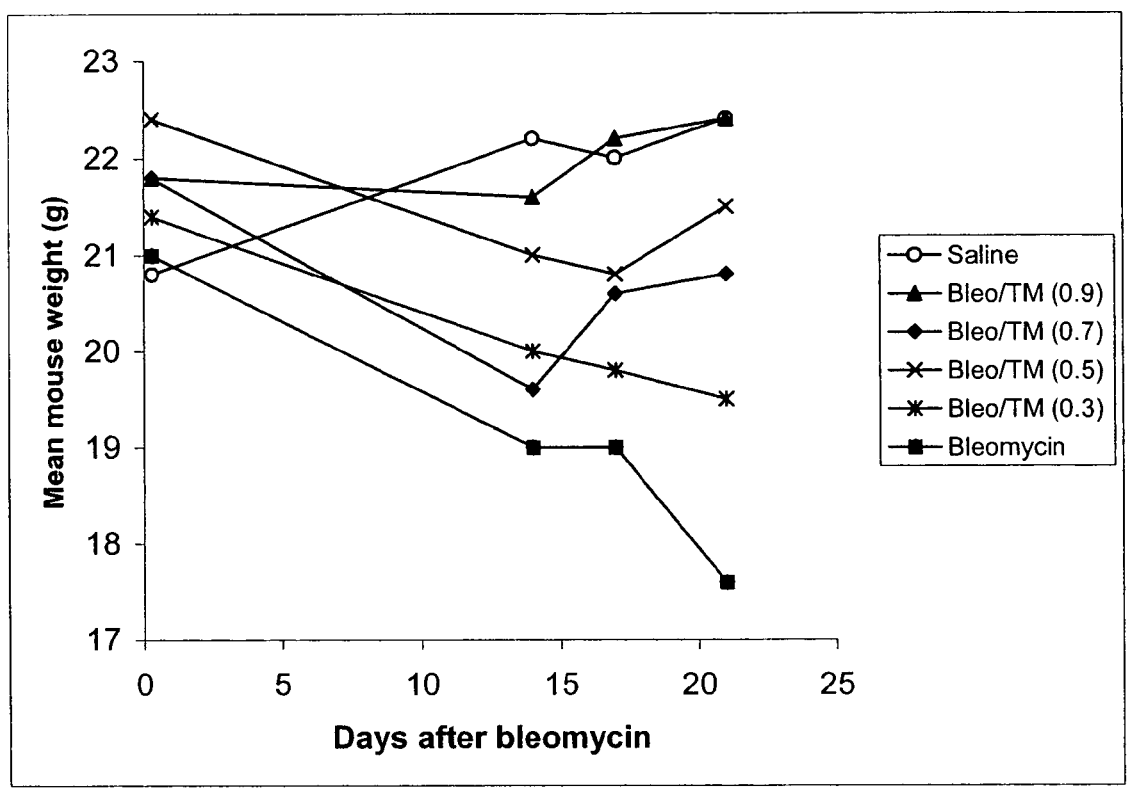
FIG. 1 shows the protective effect of tetrathiomolybdate (TM) therapy against bleomycin induced weight loss, as shown in the bottom panel. The data is shown as the mean weights for the mice in each group at several time points during experiment 2, and at the time of sacrifice at 21 days. The bleomycin group showed severe weight loss, and TM protected against weight loss in a dose-dependent manner, with the 0.9 mg dose being fully protective.

To facilitate an understanding of the present invention, a number of abbreviations, terms and phrases as used herein are defined below.

The term "inflammatory" is used to refer to pertaining, characterized by, causing, resulting from, or becoming affected by inflammation. An inflammation is a fundamental pathologic process consisting of a dynamic complex of cytologic and chemical reactions that occur in the affected blood vessels and adjacent tissues in response to an injury or abnormal stimulation caused by a physical, chemical, or biologic agent; these reactions include the local reactions and resulting morphologic changes, the destruction or removal of the injurious material, and the responses that lead to repair and healing.

The term "fibrotic" is used to refer to pertaining to or characterized by fibrosis. Fibrosis in disease or response to injury is the dysregulated excessive formation of fibrous tissue as a reactive process, as opposed to formation of fibrous tissue as a normal constituent of an organ or tissue, or as a part of normal repair of tissue.

The term "disease" refers to an interruption, cessation, or disorder of body function, systems, or organs. The term "disease" includes responses to injuries, especially if such responses are excessive. The term "condition" is used to refer to a disease or a response to injury. An "inflammatory disease" refers to a disease caused by or resulting from or resulting in inflammation. A "fibrotic disease" refers to a disease caused by or resulting from or resulting in fibrosis. A disease may include a response to injury, especially where the response is excessive, does not heal normally, and/or produces symptoms that excessively interfere with normal activities of an individual (where excessive is characterized as the degree of interference, or the length of the interference).

The term "injury" refers to damage or wound of trauma. A response to injury may be inflammation and/or fibrosis.

The term "anti-inflammatory" is used to refer to an effect or compound which has an effect of preventing, inhibiting, alleviating or decreasing inflammation or components of an inflammatory reaction, either completely or partially.

The term "anti-fibrotic" is used to refer to an effect or compound which has an effect of preventing, inhibiting, alleviating or decreasing fibrosis or components of the fibrotic reaction, either completely or partially.

The term "biocompatible" refers to compositions comprised of natural or synthetic materials, in any suitable combination, that remain substantially biologically unreactive in a subject or patient. The term "substantially unreactive" means that any response observed in a subject or patient is a subclinical response, i.e., a response that does not rise to a level necessary for therapy.

The term "biologically active agent" or "therapeutic agent" refers to an agent that possesses an activity or property capable of affecting or effecting a biochemical function, such as a structural (for example, binding ability) or regulatory activity or a reaction. Biochemical functions include but are not limited to physiological, genetic, cellular, tissue, and organismal activities. Moreover, as used herein, the term "agent" refers to biologically active agents and therapeutic agents, except where noted otherwise. Biological activities include activities associated with biological reactions or events in a subject or patient; preferably such activities can be detected, monitored, characterized, or measured.

The term "endogenous copper level" refers to the total amount of copper in the body of a patient; this amount includes both tissue and fluid amounts. The amount of copper in the body can also be divided into the amounts of available and amounts of unavailable copper. The "copper status" of a patient refers to the amount of available copper. Copper status is determined in the blood of a healthy individual, for example, by the concurrent measurement of plasma copper and ceruloplasmin. Normal plasma copper is present in two primary pools. Most plasma copper in normal individuals is part of the ceruloplasmin molecule. This copper is essentially unavailable for ready exchange with cells. Another pool of copper is more loosely bound to albumin and small molecules, such as amino acids. This latter pool of copper is readily available for cellular uptake. When TM enters the blood it complexes with the available copper, and renders it, like ceruloplasmin copper, unavailable for cellular uptake. In TM treated patients, copper status can be determined by measuring plasma ceruloplasmin alone. As the level of available copper decreases, the level of ceruloplasmin also decreases, as the amount of plasma ceruloplasmin is dependent upon copper availability.

The term "lowering endogenous copper level" refers to decreasing the copper level in the body of an animal, typically by administration of an agent which binds or complexes copper, from the level existing just before administration of the agent; copper-binding agents include but are not limited to thiomolybdates, of which tetrathiomolybdate is an example. Typically, more than one dose of a copper-binding agent is required to lower the endogenous copper level.

The term "therapeutically effective amount" is a functional term referring to an amount of material needed to make a qualitative or quantitative change in a clinically measured parameter for a particular subject. For example, prior to administration, the subject may exhibit at least one measurable symptom of disease or response to injury (for example, pulmonary congestion and/or difficulty breathing; evidence of hepatitis, or decrease in liver function; evidence or kidney inflammation or decrease in kidney function; etc), which upon administration of a therapeutically effective amount the measurable symptom is found to have changed. A therapeutically relevant effect relieves to some extent one or more symptoms of a disease or condition or returns to normal either partially or completely one or more physiological or biochemical parameters associated with or causative of the disease.

In particular, the term refers to an amount of an agent that binds or complexes copper such as thiomolybdate which amount is effective to treat an inflammatory and/or fibrotic disease and/or response to injury upon administration to a patient suffering from such a disease or response to injury. Treatment includes but is not limited to preventing the onset or shortening the course or severity of or reversing the effects of inflammatory and/or fibrotic disease or response to injury; thus, a therapeutically effective amount includes a prophylactically effective amount. In some embodiments, such effects are achieved while exhibiting negligible or manageable adverse side effects on normal, healthy tissues of the patient. Thus, the "therapeutically effective amount" can vary from patient to patient, depending upon a number of factors, including but not limited to the type of disease, the extent of the disease, and the size of the patient.

The term "biologically effective amount" is a functional term referring to an amount of material needed to make a qualitative or quantitative change in a biological activity of a particular subject; such activities include but are not limited to enzyme activities, production of antigen, and clearance of analyte from serum.

In particular, the term refers to an amount of an agent that binds or complexes copper such as thiomolybdate which amount is effective to decrease the level of endogenous copper levels upon administration to a patient.

The term "therapeutically effective time" refers to the period of time during which a therapeutically effective amount of a therapeutic agent or biologically active agent is administered sufficient to prevent the onset or to shorten the course or severity of or to reverse the effects of a disease. In particular, it is the period of time sufficient to both reduce the endogenous copper level to a target level and/or to maintain the target copper level to prevent the onset or to shorten the course or severity of or to reverse the effects of inflammatory and/or fibrotic disease.

The term "thiomolybdate" refers to molecules comprising molybdenum and sulfur, and include but are not limited to species such as $[MoS_4]^{2-}$ and $[MoO_2S2]^{2-}$. These molecules can act as bidentate ligands, and can complex copper. Examples of thiomolybdates include but are not limited to tetrathiomolybdate, trithiomolybdate, dithiomolybdate, and monothiomolybdate. Other examples include complex thiomolybdates, which include but are not limited to a zinc or an iron between two thiomolybdate groups, and which contain thiomolybdate capable of binding or complexing copper. In exemplary complex thiomolybdates, the molecule may have more than four thio groups related to more than one molybdenum.

The term "tetrathiomolybdate" (TM) refers to a compound made up of molybdenum atom surrounded by four sulfur groups, $[MoS_4]^{2-}$.

The terms "bind," "complex," and "chelate" and any grammatical equivalents (such as "binds," "binding," etc.) refer to any type of chemical or molecular interactions of copper with thiomolybdate which effectively sequester the copper with the thiomolybdate; when the copper is endogenous to a patient and thiomolybdate is administered to the patient, the terms refer to any type of chemical interactions of copper with thiomolybdate which effectively sequester the copper with the thiomolybdate rendering the copper unavailable and ultimately removing it from the patient's body.

A therapeutically effective amount of a range of values includes all values in this range. Thus, for example, a therapeutically effective amount of "between about 20 mg and about 200 mg includes all values in this range, and thus includes amounts of about 25 mg, about 30 mg, about 40 mg, about 50 mg, about 60 mg, about 70 mg, about 75 mg, about 80 mg, about 90 mg, about 100 mg, about 1100 mg, about 120 mg, about 125 mg, about 130 mg, about 140 mg, about 150 mg, about 160 mg, about 170 mg, about 180 mg, about 190 mg, or about 195 mg.

The terms "pharmaceutically acceptable," "physiologically tolerable," and grammatical variations thereof, as they refer to compositions, carriers, diluents and reagents, are used interchangeably and represent that the materials are capable of administration to or upon a subject or patient, preferably a mammal, most preferably a human, and that the materials do not substantially produce, for example, adverse or allergic reactions when administered to a subject or patient, or can be administered without the production of undesirable physiological effects such as nausea, dizziness, gastric upset, toxicity and the like. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The term "aqueous component" refers to the component of a composition that contains water (or is soluble in water). Where water is used, it may or may not contain salt(s) and may or may not be buffered. Thus, a variety of such components are contemplated including, but not limited to, distilled water, deionized water, normal saline, and phosphate buffered saline.

The term "carrier" refers to a diluent, adjuvant, excipient, or vehicle with which a compound is administered. Such pharmaceutical carriers can be sterile liquids, such as water and oils, including those of petroleum, animal, vegetable, or synthetic origin, such as peanut oil, soybean oil, mineral oil, sesame oil and the like. Water or aqueous solution saline solutions and aqueous dextrose and glycerol solutions are preferably employed as carriers, particularly for injectable solutions.

The term "patient" refers to any animal (for example, warm blooded mammal) comprising humans and non-human animals, where non-human animals include but are not limited to non-human primates, rodents, farm animals (for example, cattle, horses, pigs, goats, and sheep), pets (for example, dogs, cats, ferrets, and rodents) and the like, that is to be the recipient of a particular treatment. The terms "patient" and "subject" are used interchangeably. The term "individual" refers to any animal as described above who may or may not be a patient. A patient "having" a disease or condition is a patient "suffering" the disease or condition, and is "in need" of treatment of the disease or condition.

The term "test compound" refers to any chemical entity, pharmaceutical, drug, and the like that can be used to treat or prevent a disease, illness, sickness, or disorder of bodily function. Test compounds comprise both known and potential therapeutic compounds. A test compound can be determined to be therapeutic by using the screening methods of the present invention. A "known therapeutic compound" refers to a therapeutic compound that has been shown (for example, through animal trials or prior experience with administration to humans) to be effective in such treatment or prevention.

The terms "purify" or "to purify" refer to the removal of contaminants from a sample. The term "purified" refers to molecules, such as nucleic or amino acid sequences, that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated. As used herein, the term "purified" or "to purify" also refers to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "medical devices" includes any material or device that is used on, in, or through a patient's body in the course of medical treatment (for example, for a disease or injury). Medical devices include, but are not limited to, such items as syringes, catheters, intravenous administration assemblies including pumps and monitors, blood sampling equipment, nebulizers, small particle aerosol generators, inhalers with a propellant, and the like.

As used herein, the term "sample" is used in its broadest sense. In one sense, it is meant to include a specimen or culture obtained from any source, as well as biological and environmental samples. Biological samples may be obtained from an animal, including a human; a particular biological sample may be a fluid (for example, blood, plasma and serum), a solid (for example, stool), or a tissue; other biological samples may be obtained from other biological sources, such as food, and may be a liquid food (for example, milk), or a solid food (for example, vegetables). Environmental samples include environmental material such as surface matter, soil, water, crystals, and industrial samples. These examples are not to be construed as limiting the sample types applicable to the present invention.

DESCRIPTION OF THE INVENTION

The present invention provides methods to prevent and/or treat excessive inflammation that is part of the illness in many diseases, and/or part of the responses to injuries, by administering therapeutically effect amounts of a copper binding or complexing agent such as thiomolybdate, of which tetrathiomolybdate (TM) is an example, to a patient in need thereof. The present invention also provides methods to prevent and/or treat excessive fibrosis that is part of the illness, and/or part of the response to injury, in many diseases by administering therapeutically effect amounts of a copper binding or complexing agent such thiomolybdate, of which tetrathiomolybdate (TM) is an example, to a patient in need thereof.

Over the last several years, a common biochemical pathway has been elucidated for diseases which begin with inflammation, and which, if the patient survives, often lead to a disabling or potentially even lethal fibrosis. A partial list of such diseases or conditions includes but is not limited to liver cirrhosis, renal interstitial fibrosis (often a final common pathway for many types of renal damage), systemic sclerosis (frequently complicated by pulmonary fibrosis), keloid, hypertrophic burn scarring, and excessive fibrosis in various parts of the intestinal tract in some patients after disease or injury. The fibrosis may also be fatal, such as it is in ARDS and hepatitis C. A key player in all of these diseases is transforming growth factor beta ($TGF_\beta$). The presence, activation, or production of $TGF_\beta$ activates connective tissue growth factor (CTGF), which then stimulates collagen production as well as other molecules of fibrosis. The over-activity of this pathway is a common feature of fibrotic diseases in all organs of the body. The activation of this pathway thus activates a host of inflammatory and fibrosis-inducing cytokines. $TGF_\beta$ may also activate cytokines other than through CTGF. While all of these factors and cytokines are normal substances, and have important physiological functions, it has been discovered that their over-production and dysregulation play a central role in producing the aftermath diseases discussed above.

Treatment methods of the present invention lower endogenous copper levels and abrogate and treat diseases which begin with inflammation and which, upon patient survival, often lead to disabling or even lethal fibrosis. In some embodiments, such therapy involves administering a copper binding or complexing thiomolybdate, of which tetrathiomolybdate is an example. In the following description, it is understood that tetrathiomolybdate is simply an embodiment of the use of a copper binding or complexing thiomolybdates. While an understanding of the mechanism is not necessary to practice the present invention and the present invention is not limited to any particular mechanism, it is contemplated that reduction of endogenous copper levels alters the regulation of CTFG, $TGF_\beta$, SPARC and/or heparin. The contemplated altered regulation of these molecules is based upon observations that CTGF is a cysteine-rich protein and that cysteine-rich proteins are often involved in copper binding and copper dependence, that $TGF_\beta$ can be stimulated or activated by secreted protein acidic and rich in cysteine (SPARC), a known copper dependent cytokine, and that $TGF_\beta$ itself is dependent upon interaction with heparin molecules, many of which are known to bind copper and require copper for activity.

Tetrathiomolybdate (TM) is a unique anticopper drug which forms a stable tripartite complex with protein and copper. In the gut, if given with food, it prevents the absorption of copper from food and from endogenous secretions (saliva, gastric juice, etc). If given away from food, it is partially absorbed and inactivates copper in the blood by forming a three way complex with serum albumin. Since the free copper of the blood is in equilibrium with free copper in organs, it is possible to quickly titrate the body's free copper. TM is the most potent and rapidly acting anticopper drug available.

TM was developed for treating an inherited disease of copper toxicity, Wilson's disease, as described subsequently. The development of the treatment of Wilson's disease with TM has demonstrated that TM is safe and effective, and that it is particularly useful in the acutely ill, copper-toxic patient. The preparation of an NDA for the treatment of Wilson's disease with TM is underway.

The ability of copper reducing agents to be effective at abrogating and treating diseases and/or responses to injuries which begin with inflammation and which may lead to disabling fibrosis (or inflammatory and/or fibrotic diseases), was initially evaluated during the development of the present invention by studying the effects of TM treatment on pulmonary disease and liver disease in good animal models which exist for both diseases, as described further below.

The profibrotic pathway involving $TGF_\beta$ and CTGF is central to pathological fibrosis in many organs besides the lungs (W A Border and N A Noble, N. Engl. J. Med., 331(19): 1286-1292 [1994]; and D R Brigstock, Endocr. Rev., 20(2): 189-206 [1999]), as is described further below. The effectiveness of TM in treating pulmonary fibrosis, as described below, shows that TM therapy finds use in treating these other and similar diseases of excessive fibrosis and/or inflammation. Other diseases amenable to TM therapy include but are not limited to renal fibrosis and Alzheimer's disease, as described further below. It is therefore contemplated that in other embodiments of the present invention, the administration of therapeutically effective amounts of TM to patients susceptible to pathological fibrosis in other organs prevents and/or treats these diseases.

Other approaches to treatment of inflammatory and fibrotic diseases include other copper-lowering drugs, antibodies or antisense molecules to key cytokines, such as to $TGF_\beta$ or to CTGF, and other drugs which shut down the system. However, certain of these approaches may work better than others. Other copper lowering drugs include penicillamine, trientine, and zinc. Both penicillamine and trientine are relatively toxic, and trientine is also relatively slow acting; moreover, zinc is also slow acting. Other potential drugs include antibodies or antisense molecules to key cytokines, such as to $TGF_\beta$ or to CTGF. For example, it is known that antibody to $TGF_\beta$ is effective in treating the bleomycin mouse model. However, antibodies and antisense molecules are difficult to deliver and sustain at therapeutically effective levels in clinical situations. Other potential drugs shut down the $TGF_\beta$ system. For example, a drug called perfenidone is effective in the bleomycin mouse model, and may affect the transcription of $TGF_\beta$. However, at present, perfenidone does not appear to be in clinical use, and little is known about it.

In contrast to these other approaches, the therapeutic use of TM has been demonstrated to be safe and effective, as described further below, and studies conducted during the development of the present invention have demonstrated that therapeutically lowering endogenous copper with TM will beneficially affect a series of diseases dependent upon the $TGF_\beta$ pathway. Therefore, the present invention provides methods of treating inflammatory and/or fibrotic diseases and/or responses to injuries by therapeutically lowering endogenous copper levels in a patient in need thereof. Preferably, such conditions are dependent upon the $TGF_\beta$ pathway. In some embodiments, the therapy comprises administering therapeutically effective amounts of a copper binding or complexing agent for a therapeutically effective time. Exemplary agents include but are not limited to thiomolybdates, of which tetra-, tri-, di-, and monothiomolybdates are non-limiting examples.

I. Pulmonary Diseases

For examining pulmonary disease, the bleomycin mouse model was used. Pulmonary fibrosis, idiopathic or otherwise, is commonly progressive and essentially untreatable with a fatal outcome (R K Coker and G J Laurent, Thorax., 52(3): 294-296 [1997]; and K Zhang and S H Phan, Biol. Signals., 5:232-239 [1996]). It is clear from a rather wide body of work that the underlying mechanism involves dysregulation and overproduction of certain cytokines (R K Coker and G J Laurent, Thorax., 52(3):294-296 [1997]; K Zhang and S H Phan, Biol. Signals., 5:232-239 [1996]; S H Phan, Thorax., 50(4):415-421 [1995]; R E Smith et al., J. Leukoc. Biol., 57(5):782-787 [1995]; and C M Hogaboam et al., Proc. Assoc. Am. Physicians, 110(4):313-320 [1998]). A central mechanism is hypothesized to involve continued overproduction of transforming growth factor beta ($TGF_\beta$), which in turn increases the production and/or activity of connective tissue growth factor (CTGF) (N Khalil and A H Greenberg, Ciba Found. Symp. 157:194-211 [1991]; W A Border and N A Noble, N. Engl. J. Med., 331(19):1286-1292 [1994]; M Denis, Immunology, 82(4):584-590 [1994]; J A Lasky et al., The American Physiological Society, L365-L371 [1998]; D R Brigstock, Endocr. Rev., 20(2):189-206 [1999]; J T Allen et al., Cell Mol. Biol., 21:693-700 [1999]; and J F Pittet et al., J. Clin. Invest., 107:537-1544 [2001]).

Bleomycin when given to cancer patients produces pulmonary fibrosis in about 3% of the patients (M Ishizuka et al., J. Antibiot. (Tokyo), 20:15 [1967]). Based upon these observations, a mouse model of pulmonary fibrosis has been developed, in which intratracheal instillation of bleomycin uniformly produces pulmonary fibrosis (R E Smith, J. Leukoc. Biol., 57(5):782-787 [1995]; N Khalil and A H Greenberg, Ciba Found. Symp., 157:194-211 [1991]; J A Lasky, The American Physiological Society, L365-L371 [1998]; D R Brigstock, Endocr. Rev., 20(2):189-206 [1999]; J T Allen et al., Am. J. Respir. Cell Mol. Biol., 21:693-700 [1999]; S H Phan and S L Kunkel, Exp. Lung. Res., 18:29-43 [1992]; and J. Clin. Invest. 107:537-1544). Thus, the mice develop a severe lung inflammation followed by fibrosis in 2-3 weeks, at which time they are sacrificed. Fibrosis is quantified in lung tissue by measuring hydroxyproline, a key component of the collagen that is deposited in fibrotic lung. The mouse bleomycin model is believed to be a good model for human pulmonary fibrosis. The hypothesis that $TGF_\beta$ is central to pulmonary fibrosis has been validated by studies showing that inhibition of $TGF_\beta$ by pharmacological means or by antibodies greatly reduces the pulmonary fibrosis produced by bleomycin or other methods of lung injury in the mouse (M Denis, Immunology, 82(4):584-590 [1994]; and J F Pittet et al., J. Clin. Invest., 107:537-1544 [2001]).

Using the bleomycin mouse model to examine the effects of TM treatment in developing the present invention, it was observed that copper-lowering therapy with TM can dramatically prevent most of the lung damage and fibrosis from tracheal bleomycin instillation in mice (as described in Example 1 and as shown in Table 1). Moreover, there is a strong dose-response relationship between the amount of TM administered and the degree of pulmonary protection (as shown in Table 3 and FIG. 2). TM therapy also protects against bleomycin induced weight loss (as shown in FIG. 1). TM treatment can be initiated, for example, up to at least seven days after the bleomycin instillation, and still offer significant protection against pulmonary damage (as shown in FIG. 3). These results indicated that TM treatment completely abrogated fibrosis and markedly attenuated inflammation in an animal model that is directly relevant to ARDS and pulmonary fibrosis in humans.

Although it is not necessary to understand the mechanism in order to practice the invention, and it is not intended that the invention be limited to any particular mechanism, it is hypothesized that the mechanism of the protection effected by TM therapy is due to the inhibition of one or more steps in the profibrotic pathway which involves activation of $TGF_\beta$, which in turn activates CTGF, which then activates the formation of collagen and other profibrotic molecules, as described above.

It is also possible that the mechanism of this effect involves primarily suppression of inflammation, as for example by inhibiting proinflammatory cytokines. If the inflammatory reaction to bleomycin is mitigated by TM therapy, the signaling to the fibrotic pathway might be lessened, resulting in less fibrosis. However, the observation that TM therapy initiated significantly after bleomycin instillation (as, for example, at day 7) still has a significant effect in inhibiting fibrosis (as described in Example 1 and shown in FIG. 3) suggests that suppression of inflammation is not the sole effect of TM. That is because TM therapy initiated on day 7 would not reduce copper levels at the therapeutic area until about day 11, by which time all or most of the inflammation and inflammatory stimuli would have subsided. The positive results observed when the drug treatment is initiated significantly after bleomycin instillation thus suggests that TM can act by direct inhibition of the fibrotic pathway. Of course, TM therapy might result in inhibition of both inflammation and fibrosis.

Irrespective of the pathway involved, or of the underlying molecular mechanism, the fact that TM therapy can so markedly inhibit fibrosis in this model confirms the use of this approach to preventing and treating pulmonary fibrosis in human patients. The experimental results indicate that TM therapy is effective after injury (as, for example, as is shown in FIG. 3), which supports its efficacy in clinical use. The use of TM has previously been proven to be remarkably safe, as demonstrated by its considerable experimental use in humans for treatment of Wilson's disease (G J Brewer et al., Arch. Neur., 53:1017-1025 [1996]; and G J Brewer, PSEBM, 223 (1):39-49 [2000]) and for treatment of cancer (G J Brewer et al., Clin. Cancer., 6:1-10 [2000]; and G J Brewer, Soc. for Exp. Biol. and Med., 226:665-673 [2001]). The only side effect of lowering copper levels by TM therapy in cancer has been over-treatment, which leads to an easily reversible bone marrow depression. The use of serum ceruloplasmin as a surrogate to monitor copper status has proven to be effective, reliable, and easy to use (G J Brewer et al., Clin. Cancer, 6:1-10 [2000]).

Based upon these results, clinical use of TM therapy for ARDS and/or pulmonary fibrosis in human patients is contemplated. It is therefore contemplated that in other embodiments of the present invention, the administration of therapeutically effective amounts of TM to patients susceptible to pulmonary fibrosis prevents and/or treats this disease.

II. Liver Disease

Figure 4:
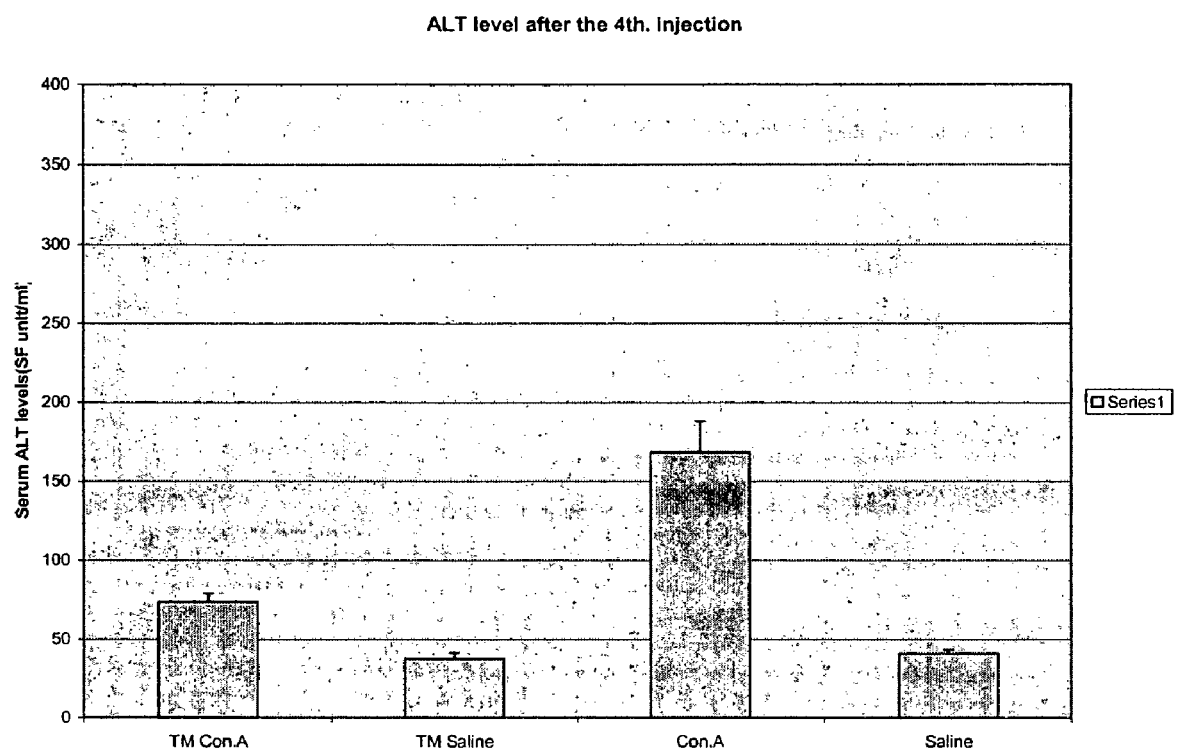
FIG. 4 shows the protective effect of administration of TM against concanavilin A induced cirrhosis of the liver. Abbreviations: ConA, indicates concanavilin A treated group; Saline, indicates saline treated control groups; ALT, represents alanine amino transferase, SF, represents Sigma-Frankel units (described further in the Examples).

For examining liver disease, studies of the mouse model of liver damage (hepatitis) followed by cirrhosis were undertaken. Two of four appropriate mouse models were involved. In one model, concanavilin A (ConA) treatment was utilized to produce cirrhosis. The Con A was injected intravenously once weekly into mice, and produced a hepatitis, which is manifested by an increasing level of transaminase enzymes in the blood. TM therapy almost completely inhibits this increase, indicating suppression of inflammation (as is described in Example 7 and as is shown in FIG. 4). The results indicated that TM treatment completely abrogated fibrosis and markedly attenuated inflammation in a model that is directly relevant to hepatitis in humans. It is therefore contemplated that in other embodiments of the present invention, the administration to patients in need thereof of therapeutically effective amounts of TM after liver damage due to hepatitis prevents or decreases subsequent cirrhosis.

III. Kidney Disease

After kidney injury of almost any type, a diffuse interstitial fibrosis (believed to be due to over-activity of the $TGF_\beta$ pathway) produces kidney failure. It is therefore contemplated that in other embodiments of the present invention, the administration to patients in need thereof of therapeutically effective amounts of TM after kidney injury prevents or decreases fibrosis, thereby preventing or abrogating kidney failure subsequent to kidney damage.

IV. Alzheimer's Disease $TGF_\beta$ has been implicated in Alzheimer's plaque formation. Moreover, copper has been implicated in the precipitation of the amyloid into the plaques in the course of the disease. It is therefore contemplated that in further embodiments of the present invention, the administration to patients in need thereof of TM results in lowering copper levels, thus preventing any further precipitation; this results in arresting the Alzheimer's disease, and in some cases allows some recovery from the disease.

According to R S Turner (Neurologic aspects of Alzheimer's disease, In: Interdisciplinary handbook of dementia: psychological, neurologic, and psychiatric perspectives. John Wiley & Sons. Lichtenberg Pa., Murman D L and Mellow A M), Alzheimer's disease (AD) currently affects about 2-3% of individuals at age 65, and the incidence approximately doubles for every 5 years of age afterward. The prevalence of AD approaches 50% of those over age 85 (as reported by D A Evans et al., JAMA, 262:2551-2556 [1989]). AD is not inevitable with aging, however, and "escapees" warrant further epidemiologic and genetic study. In 1990, there were an estimated 4 million people in the U.S. with AD. Because of an expanding population and increasing life expectancy, the number of affected individuals is projected to increase to 14 million in the U.S. in 2050. Women make up a larger proportion of patients who live and die with AD due to a higher relative risk and longer life expectancy than men. In 2001, the annual costs for care of a patient with AD were approximately $28,000 for formal care and $11,000-$35,000 for informal care (D P Rice et al., Am. J. Manag. Care, 7:809-818 [2001]). The high prevalence of AD results in an enormous economic impact. As the elderly population also increases in less affluent countries, large numbers of patients with AD will emerge and face intense competition from the younger populace for scarce health care resources. The slow progression of disease (with an average of 7 years, and a range of 2-18 years) engenders many years of health care costs. As dementia becomes severe and patients become progressively more dependent on caregivers for basic activities of daily living, expenditures increase. A major cost for many patients in the latter stages of AD is assisted living and nursing home care.

Genetically, AD is a multifactorial disease, with the possible involvement of several genetic components (E K Luedecking et al., Hum. Genet., 106:565-569 [2000]). Three causative genes at chromosomes 21, 14, and 1 have been identified in the early-onset form of AD. These three genes, amyloid precursor protein (APP), presenilin-1 (PS1), and presenilin-2 (PS2), account for most of the cases of autosomal dominant familial AD (C L Lendon et al., JAMA, 277:825-831 [1997]). Familial AD, however, accounts for <1% of all AD cases. Additionally, the apolipoprotein E4 allele is a risk factor for late-onset AD (W J Strittmatter et al., Proc. Natl. Acad. Sci. USA, 90:1977-1981 [1993]). However, mutations in these genes do not explain the occurrence of disease in all patients (E K Luedecking et al., Hum. Genet. 106:565-569 [2000]).

Biochemically, AD is characterized by the deposition of beta amyloid protein (A$\beta$) within the neocortex, associated with neuronal demise and oxidative stress (AI Bush, Bio-inorganic Chemistry, 184-191 [2000]). The deposition of A$\beta$ is considered to be closely related to the primary pathogenesis of AD. For example, familial AD-linked mutations of APP, PS1, and PS2, increase both cerebral A$\beta$ burden and A$\beta$1-42 production, underscoring the role that A$\beta$ metabolism plays in AD pathogenesis (CS Atwood et al., Met. Ions Biol. Syst., 36:309-364 [1999]). Moreover, the deposition of A$\beta$ in the neocortex of transgenic mice overexpressing A$\beta$ is accompanied by many of the other neuropathological features of AD, including intraneuronal tau abnormalities and neuronal loss (M E Calhoun et al., Nature, 395:755-756 [1998]), as well as signs of oxidative damage similar to those seen in AD-affected brain (MA Smith et al., J. Neurochem., 70:2212-2215 [1998]). The length of the A$\beta$ species is considered to be one important factor in AD pathogenesis as A$\beta$1-42, a minor free soluble species in biological fluids, is enriched in amyloid deposits. Many studies have now confirmed that A$\beta$ is neurotoxic in cell culture. Hence, there is a compelling argument to consider A$\beta$ deposition as a therapeutic target in AD (AI Bush, Metals and neuroscience. Bio-inorganic chemistry, 184-191 [2000]).

For examining the effects of TM on Alzheimer's disease, the transgenic mouse model Tg2576 is used. Transgenic (tg) mouse models have proven to be useful tools in testing hypotheses of AD pathogenesis as well as testing novel therapeutic strategies (Turner R S. Commentary). Tg human amyloid precursor protein (hAPP) mice recapitulate some but not all features of human AD, and may therefore be best described as developing a partial AD-like phenotype with aging. However, the distribution of amyloid pathology in tg hAPP mouse brain is remarkably similar to the human disease. One of the more widely studied hAPP tg mouse lines-Tg2576 mice developed by Hsiao et al. (K Hsiao, Exp. Gerontol., 33:883-889 [1998]; and K Hsiao et al., Science, 274: 99-102 [1996])-expresses the familial AD gene hAPP swe (Swedish mutation; $APP_{K670N/M671L}$ in the APP770 numbering system) in a C57B6/SJL genetic background. The neuron-specific prion protein promoter drives expression of the transgene. With aging, Tg2576 mice exhibit a phenotype that includes learning and memory deficits, an abnormal pattern of glucose metabolism in brain, and pathologic changes including amyloid plaque deposition, elevated A$\beta$40 and A$\beta$42 levels, neuritic changes, phosphorylated tau epitopes, $\alpha$-synuclein positive dystrophic neurites, gliosis, and inflammatory responses; however, aging mice develop neither neurofibrillary tangles nor significant neuronal loss (R S Turner, Commentary; K Hsiao, Exp. Gerontol., 33:883-889 [1998]; and K Hsiao et al., Science, 274:99-102 [1996]). Cholinergic abnormalities in the immediate vicinity of amyloid plaques are apparent in immunostained brain sections from older hAPP tg (C Sturchler-Pierrat et al., Proc. Natl. Acad. Sci. USA, 94:13287-13292 [1997]) and hPresenilin-1 (mutant)/ hAPP double tg mice (T P Wong et al., J. Neurosci., 19:2706-2716 [1999]).

Amyloid plaque deposition in aging hAPP tg mice may be modulated pharmacologically, immunologically, environmentally, and genetically. For example, amyloid pathology is accelerated in hPresenilin-1 (mutant)/hAPP double tg mice (L Holcomb et al., Nat. Med., 4:97-100 [1998]), and absent in murine ApoE null (−/−)/hAPP tg mice (K R Bales et al., Nature Genet., 17:263-264 [1997]). In the latter mice, hApoE4 transgene expression promotes more fibrillar amyloid deposition than hApoE3 (D M Holtzman et al., Proc. Natl. Acad. Sci. USA, 97:2892-2897 [2000]). Human transforming growth factor $\beta$1/hAPP double tg mice develop increased A$\beta$ deposition within plaques, with a greater proportion of meningeal and vascular deposition, reflecting a role of inflammation in amyloidogenesis (T Wyss-Coray et al., Nature, 389:603-606 [1997]). Amyloid pathology in hAPP tg mice may be prevented by pharmacologic treatment with the phosphatidylinositol kinase inhibitor wortmannin that inhibits A$\beta$ production in vitro (S J Haugabook et al., FASEB Journal, published online 9 Nov. 2000), by the $Cu^{++}$/ $Zn^{++}$-chelator/antibiotic clioquinol that blocks amyloid fibril formation in vitro (L Helmuth, Science, 1273-274 [2000] editorial), or by the nonsteroidal anti-inflammatory drug ibuprofen (G P Lim et al., J. Neurosci., 20:5709-5714 [2000]). The efficacy of this wide variety of pharmacologic treatments in preventing amyloid deposition in tg AD mice reveals multiple alternative and competing therapeutic strategies. Novel therapeutics targeting the recently-identified $\gamma$-secretase complex and $\beta$-secretases that generate A$\beta$40 and A$\beta$42 from APP and immune-based strategies are also under experimental investigation (D J Selkoe, Nature, 399 suppl:A23-31 [1999]). It is contemplated that administration of a copper binding or complexing agent such as thiomolybdate to Tg2576 mice results in a reduction of A$\beta$40 and A$\beta$42 levels in brain homogenates.

V. Cancer and Angiogenic Diseases

Research indicates that angiogenesis is required for cancer growth, and since adults have little requirement for angiogenesis, the present invention contemplates that antiangiogenic therapies might provide successful cancer treatments.

Copper has been shown to be a stimulus of angiogenesis in a rabbit cornea model in which copper sulfate, or a copper containing molecule, ceruloplasmin, were both angiogenic (A Parke et al., Am. J. Clin. Path., 137:1121-1142 [1988]; K S Raju et al., J. Natl. Cancer Inst., 69:1183-1188 [1982]). When rabbits were made partially copper deficient with penicillamine and a low copper diet, an angiogenic molecule, PGE1, placed in the cornea, showed markedly reduced angiogenesis. Brem and colleagues implanted brain tumors in the brains of copper deficient rabbits and rats, and showed markedly reduced growth and invasive properties of the tumors in the copper deficient animals compared to controls (S S Brem et al., Am. J. Path., 137:1121-1147 [1990]; S S Brem et al., Neurosurgery, 26:391-396 [1990]). Some embodiments of the present invention provide TM compositions that are more potent and much safer anticopper drugs then penicillamine and trientine and which are contemplated for use in treating cancer. Indeed, in five different rodent cancer models, TM has shown dramatic effects on inhibition of tumor growth, including; the HER2/neu transgenic mammary model (Q Pan et al., Cancer Res., 62:4854-4859 [2002]); a head and neck model (C Cox et al., Laryngoscope, 111:696-701 [2001]); a prostate model (K van Golen et al., Neoplasia, 4(5):373-379 [2002]); a lung model (M Khan et al., Neoplasia, 4(2): 1-7 [2002]); and an inflammatory breast model (Q Pan Q et al.). TM has also shown positive effects in spontaneous canine cancers. A clinical phase ½ study of a variety of metastatic and advanced cancers has shown positive results, with an average of 11 months freedom from progression in evaluable patients, and long term stabilization in three patients (G J Brewer et al., Clin. Cancer Res., 6:1-10 [2000]). A number of phase 2 studies of specific cancers are under way.

While not being limited to any mechanism, the present invention contemplates that the antiangiogenic mechanism of TM appears to involve the copper dependence of a large number of angiogenic promoters (G J Brewer, EBM, 226: 665-673 [2001]). In addition, lowering copper levels to a midrange inhibits nuclear factor kappa B (NFκb), a type of master switch for cytokine transcription. These mechanisms may make copper lowering therapy a more global inhibitor of angiogenesis than other approaches. In some embodiments, copper is maintained in the midrange by using ceruloplasmin (Cp) levels as a surrogate marker of copper status.

The present invention also contemplates the antiangiogenic therapeutic effects of TM in diseases of neovascularization besides cancer (e.g., animal models of retinopathy). In retinopathy of prematurity, newborn mice exposed to hyperoxia for five days develop a marked retinopathy after four days exposure to room air, with a peak of a major angiogenic stimulus, vascular endothelial growth factor (VEGF), at 24 hours. TM treatment has shown strong inhibition of the VEGF peak and a dramatic reduction in retinal neovascularization.

The invention's success with the antiangiogenic use of TM through its inhibition of angiogenic cytokines led to investigation of key cytokines of fibrosis and inflammation, which become dysregulated in a series of diseases of fibrosis and inflammation, that may be similarly copper dependent, and treatable with TM.

VI. Primary Biliary Cirrhosis

The specific cause of primary biliary cirrhosis (PBC) remains unknown, although it is though to be an autoimmune disorder (R T Chung and D K Podolsky, Cirrhosis and its complications: Primary biliary cirrhosis. In: Harrison's Principles of Internal Medicine 15th edition, E Braunwald et al., (Eds). McGraw-Hill Companies, Inc, New York, pp. 1757-1758 [2001]). A circulating IgG antimitochondrial antibody (AMA) is found in more than 90% of patients, and only rarely in other diseases. PBC is often associated with other autoimmune disorders such as autoimmune thyroiditis, type I diabetes mellitus, and other autoimmune syndromes.

The disease is divided into four stages. Stage I is a necrotizing inflammatory process of the portal triads, with destruction of smaller bile ducts, a heavy infiltrate of inflammatory cells, mild fibrosis, and part of the time, cholestasis. In stage II, the inflammatory reaction decreases, the number of bile ducts is reduced, and small bile ductules proliferate. In stage III, which results from progression over months to years, there is a decrease in interlobular ducts, loss of liver cells, and increase in periportal fibrosis leading to a fibrotic network. Stage IV is micronodular or macronodular cirrhosis.

Clinically the disease may begin with symptoms of itching or fatigue. Often it is picked up by an elevated serum alkaline phosphatase on routine screening. Ninety percent of PBC patients are women. Over a period of months to years the disease may progress and produce jaundice. Eventually signs of hepatic failure and of portal hypertension appear. Progression is somewhat variable, with some patients dying or requiring transplant in 5 years, while others have a more protracted course.

A presumptive diagnosis may be made on the basis of an elevated alkaline phosphatase usually in a woman, with or without jaundice, and a positive AMA test. However, since false positives do occur, diagnosis should always be confirmed by a liver biopsy showing typical findings of PBC.

Treatment with the bile acid ursodeoxycholic acid (ursodiol) is useful for symptomatic and sometimes biochemical improvement, but has not been shown to alter the progressive course of the disease. No other treatment, aside from liver transplantation, has been shown to be effective.

Neuman et al. (M Neuman et al., J. Gastro. and Hepat., 17:196-202 [2002]) report that an increase in serum levels of both TNFα and TGFβ in PBC (e.g., TNFα is 324 pg/ml in PBC versus 77 in normal controls). Second, they conclude that serum TNFα and TGFβ levels reflect disease severity. Third, they find that ursodiol therapy significantly decreases serum TNFα and TGFβ levels in PBC, but not to normal levels (for example, TNFα after 2 years of ursodiol therapy was 124 pg/ml, still significantly higher than control values). Since in animal model work both in the lung and the liver TM is able to essentially normalize TNFα and TGFβ levels in affected organs after injury, it is contemplated that TM therapy is beneficial in PBC.

The prevalence of PBC in the U.S. is 65.4 cases for women and 12.1 cases for men (40.2 overall) per 100,000 population. At 402 cases/1 million, and using a U.S. population of 288 million, this calculates out to about 116,000 case prevalence in the U.S., well below the 200,000 figure required to qualify as an orphan disease.

VII. Agents That Bind or Complex Copper

A. Thiomolybdates

The present invention provides methods to prevent and/or treat inflammation and/or fibrosis by administering a therapeutically effective amount of at least one copper binding or complexing agent that includes but is not limited to a thiomolybdate, to a patient in need thereof. Thiomolybdates are molecules comprising molybdenum and sulfur, and include but are not limited to species such as $[MoS_4]^{2-}$ and $[MoO_2S2]^{2-}$. These molecules can act as bidentate ligands, and can complex copper. Examples of thiomolybdates include but are not limited to tetrathiomolybdate, trithiomolybdate, dithiomolybdate, and monothiomolybdate. Other examples include complex thiomolybdates, that include but are not limited to a zinc or an iron between two thiomolybdate groups, and that contain thiomolybdate capable of binding or complexing copper. In exemplary complex thiomolybdates, the molecule may have more than four thio groups related to more than one molybdenum. In the following description, it is understood that tetrathiomolybdate is simply an embodiment of the use of a copper binding or complexing thiomolybdates. It is also understood that any thiomolybdate may be utilized as one or several of different salts, such as those described for TM below.

Tetrathiomolybdate (TM) is a compound made up of molybdenum atom surrounded by four sulfur molecules.

Various salts of TM are available; salts of TM include but are not limited inorganic cations such as ammonium, zinc, and iron ions, and organic cations such as tetraethyl, tetrapropyl and choline ions. Different salts have differing properties of solubility in water and ingestible solvents (such as alcohol), stability upon storage alone or in formulations, bioavailability to a patient, and toxicity to a patient. Thus, depending upon the use and formulation, any particular salt is selected to maximize solubility in water (or a solvent miscible with water and which can be tolerated by a patient, such as alcohol), to maximize stability upon storage, as for example as the compound or as part of a formulation, to minimize toxicity to a patient, and to maximize bioavailability after administration to a patient.

In some embodiments, the salt of TM is an ammonium salt. TM as the ammonium salt can be purchased from Aldrich Chemical Company (catalog number W 180-0; Milwaukee, Wis.; available in one kilogram bulk lots) as a black powder that is moderately water soluble, yielding a bright red solution; these preparations are also certified pure for human use. The ammonium salt of TM has one undesirable property, that of mild air instability. Thus, the bulk drug should be stored in the absence of oxygen, or the oxygen will gradually exchange with the sulfur, rendering the drug ineffective over time. The bulk drug is therefore stored under argon. Stability assays developed by the inventors indicate that this drug is stable for several years under argon (G J Brewer et al., Arch. Neurol., 48(1):42-47 [1991]). Capsules can be filled by hand, and the drug is stable in capsules for several months at room temperature.

Alternatively, TM, which is generally synthesized as the ammonium salt, may be more stable under air as a different salt. Thus, other salts have been prepared and evaluated for solubility, stability and anticopper activity. In other embodiments, the salt tetrapropyl tetrathiomolybdate (TPTM) has met all desired properties. In other embodiments, the salt choline TM has suitable desirable properties. In yet other embodiments, the salt tetraethyl TM has suitable properties. These exemplary salts of TM have suitable solubility in water, and behave similarly to ammonium salt of TM in in vitro copper complexing studies.

Other pharmaceutically acceptable salts include but are not limited to include salts formed with inorganic acids such as, for example, hydrochloric or phosphoric acids, or such organic acids as acetic, oxalic, tartaric, mandelic, and the like. Salts can also be derived from inorganic bases such as, for example, sodium, potassium, ammonium, calcium, or ferric hydroxides, and such organic bases as isopropylamine, trimethylamine, histidine, procaine and the like.

Although it is not necessary to understand the underlying mechanism to practice the invention, and the invention is not intended to be so limited, it is believed that TM acts by forming a tripartite complex with copper and protein (Mills et al., J. Inorg. Biochem., 14:189 [1981]; Mills et al., J. Inorg. Biochem., 14:163 [1981]; and Bremner et al., J. Inorg. Biochem., 16:109 [1982]). It is further believed that TM has two mechanisms of action. Given with meals, it complexes both copper in food and endogenously secreted copper with itself and food protein, and prevents the absorption of copper. Patients can be put into an immediate negative copper balance with TM by administering it with meals. Given between meals, the TM is absorbed into the bloodstream, and complexes serum copper with itself and albumin, rapidly rendering the copper unavailable for cellular uptake. Since free copper in organs is in equilibrium with free copper in blood, free copper in the organs will quickly be reduced to very low levels if the blood copper is bound. This complex is cleared through the kidney and the liver. No matter what its mechanism of action is, TM is a potent and rapidly acting anticopper agent. It is also contemplated that other thiomolybdates complex copper through similar though not necessarily identical mechanisms. In some hypotheses, some thiomolybdates directly bind copper. In yet other hypotheses, a tripartite copper-thiomolybdate-protein complex is degraded in the body, but the thiomolybdate still results in lowering endogenous copper levels. For example, trithiomolybdate, dithiomolybdate, and monothiomolybdate compounds, like tetrathiomolybdate, are believed to form a tripartite complex with copper and protein that renders the copper unavailable, and eventually leads to clearance of the copper-complex.

The only known toxicity of TM discovered in animal studies is through its anticopper effects. Animals given TM in sufficient quantity to produce severe copper deficiency suffer from a variety of copper deficiency-related problems, including anemia (Mills et al., J. Inorg. Biochem., 14:163 [1981]; and Bremner et al., J. Inorg. Biochem., 16:109 [1982]). However, none of these occur if the animal is copper supplemented (Mills et al., J. Inorg. Biochem., 14:189 [1981]), or maintained at a moderate copper level. Tetrathiomolybdate (TM) is a drug that the inventors have developed as an orphan therapy for Wilson's disease, as described further below. The drug does an excellent job of gaining quick control over copper toxicity and preventing the neurological worsening that occurs 50% of the time during initial treatment with a commonly used drug for Wilson's disease, penicillamine (Brewer et al., Arch. Neurol., 48(1):42-47 [1991]; Brewer et al., Arch. Neurol., 51(6):545-554 [1994]; and Arch. Neurol., 53:1017-1025 [1996]). So far, the inventors have treated 79 Wilson's disease patients with TM, generally for an eight-week period. TM thus fills a very important niche in the initial treatment of Wilson's disease. The Wilson's disease work has provided extensive experience with TM therapy in the human, and provides documentation of TM's extremely low level of toxicity in humans.

In the studies of treating human patients with Wilson's disease studies, one side effect occasionally observed is a reversible anemia, due to TM's anticopper effects. Given in too high a dose, TM renders the bone marrow severely or totally copper deficient. Since copper is required for erythropoiesis, an anemia develops. That anemia is rapidly reversible by simply stopping TM. In the Wilson's disease studies, this over-treatment effect of TM has been diminished by simply reducing the dose to 60 mg per day from the standard 120 mg per day. A second side effect seen during treatment with TM of Wilson's disease, but not in treatment of cancer, is a mild increase in serum transaminase levels (Wilson's patients already have liver disease). This mild increase is diminished or removed by reducing the dose of TM. In humans without Wilson's disease, such as patients with inflammatory and/or fibrotic diseases, a level of mild copper deficiency at a pre-anemia state can be established simply by carefully monitoring ceruloplasmin (Cp) levels during TM therapy. The level of ceruloplasmin is reduced to and maintained at a targeted level; in some embodiments, this targeted level is between about 5 and 15 mg/dl.

TM is eventually metabolized to elemental molybdenum (Mo), so the potential toxicity of Mo has to be considered. However, it turns out that Mo is quite innocuous at the levels produced from breakdown of TM used at the therapeutic regimes described herein. In one example, up to 50 mg of Mo/day is administered for two weeks, then no more than about 25 mg/day is administered for maintenance. High doses of 350 to 1400 mg/day of Mo were previously used for 4-11 months in patients with Wilson's disease, without toxicity (Bickel et al., Quart. J. Med., 50:527 [1957]). Thus, because about 37% of TM by weight is Mo, the dose range of 25-50 mg/day poses no predictable problems, and should be entirely safe.

B. Monitoring Copper Levels

The mechanism of action of TM is to lower systemic or endogenous copper levels. Copper status is evaluated by measuring the level of ceruloplasmin, a copper-containing serum protein secreted by the liver, as the amount of ceruloplasmin is dependent upon copper availability. Measuring total serum copper is not a good indicator for evaluating copper status, because the TM complex with copper accumulates in the blood before it is cleared from the body, thus elevating serum copper in spite of reduced copper availability. Thus, the serum ceruloplasmin, which is directly dependent upon liver copper status, is an accurate indicator of copper status or availability in preferred embodiments.

VIII. Combination Therapy

In the present invention, it is initially contemplated that a method to treat inflammation and/or fibrosis comprises administration of at least one copper binding or complexing agent, which include but are not limited to thiomolybdates of which TM is an example; in this method, treatment is accomplished by administering a single copper binding or complexing agent. It is also contemplated that a combination of more than one copper binding or complexing agent may be administered to a patient; the different agents are chosen from different thiomolybdates, different salts of different thiomolybdates, other copper binding or complexing agents, or any combination thereof. Thus, in some embodiments, the agents comprise a combination of at least two different thiomolybdates, such as a tetrathiomolybdate and a trithiomolybdate; in other embodiments, the agents comprise a combination of at least one thiomolybdate and at least one other copper binding or complexing agents. In yet other embodiments, the agents comprise a combination of at least two different salts of a single thiomolybdate, such as a tetraethyl—and a tetrapropyl—tetrathiomolybdate; in yet other embodiments, the agents comprise a combination of at least two different thiomolybdates, of which at least one thiomolybdate comprises at least two different salts; in yet other embodiments, the agents comprise a combination of at least one thiomolybdate, which comprises a combination of at least two different salts, and at least one other copper binding or complexing agent.

Moreover, it is also contemplated that the methods of the present invention may be combined with other methods generally employed in the treatment of the particular disease or disorder that the patient exhibits. This is particularly true for treatment of diseases for which decreasing copper levels ameliorates does not eradicate the disease; in those cases, it may be advantageous to use additional compounds which eradicate the disease. In other cases, it may be useful to administer drugs in addition to TM in order to obtain additive or synergistic effects. For example, in connection with inflammation, the methods of the present invention include classical or new approaches in treating and/or preventing inflammation. Thus, in some embodiments, the present invention provides a method of treating and/or preventing inflammation comprising administering at least one copper binding or complexing agent as described above to a patient in need thereof, and administering at least one other known or discovered antiflammatory drug; known antiflammatory drugs include but are not limited to steroids, NSAIDS (non-steroidal anti-inflammatory drugs), and chemotherapeutic agents as are used in some auto-immune diseases. In other examples, in connection with fibrosis, the methods of the present invention include classical or new approaches in treating and/or preventing fibrosis. Thus, in some embodiments, the present invention provides a method of treating and/or preventing fibrosis comprising administering at least one copper binding or complexing agent as described above to a patient in need thereof, and administering at least one other known or discovered anti-fibrotic drugs; anti-fibrotic drugs include but are not limited to antibodies or antisense agents directed to specific cytokines or to their receptors, as well as to other molecules which enhance fibrosis. In these embodiments, it is contemplated that the administration of other anti-inflammatory and/or anti-fibrotic drugs are not known to be detrimental in themselves, and that administration of other anti-inflammatory and/or anti-fibrotic drug do not substantially counteract the effectiveness of the endogenous copper lowering therapy by administering copper binding or complexing agents. By substantially counteracting the effectiveness of the endogenous copper lowering therapy, it is meant that the combined therapy lowers endogenous copper sufficiently to observe an amelioration of at least one symptom of a disease or condition. In the embodiments in which at least one additional anti-inflammatory and/or anti-fibrotic drug is administered in combination with the administration of a copper binding or complexing agent, there is no requirement for the combined results to be additive of the effects observed when each treatment is conducted separately, although this is evidently desirable, and there is no particular requirement for the combined treatment to exhibit synergistic effects, although this is certainly possible and advantageous. It is also contemplated that the administration of the different agents or drugs occurs simultaneously, as for example administering the combination of agents and drugs at the same times, and/or at different times during the course of therapy; any combination of administration is contemplated.

IX. Pharmaceutical Compositions and Kits

Pharmaceutical compositions of the present invention will generally comprise an effective amount of an agent for use in the present invention, such as copper binding or complexing thiomolybdates, of which tetrathiomolybdate is an example, dissolved or dispersed in a pharmaceutically acceptable carrier or aqueous medium.

A. Oral Formulations

In preferred embodiments of the present invention, TM is administered orally. Oral administration is effected by a number of means, such as by feeding tubes for administration into the gastrointestinal track, and preferably the duodenum, or by tablets or powders or solutions for administration by mouth. A feeding tube may be preferred for an acute disease, whereas administration by mouth may be preferred for chronic diseases and/or for maintenance, once an appropriate level of copper has been attained. Oral pharmaceutical formulations include but are not limited to tablets or other solids, time release capsules, liposomal forms and the like. Other pharmaceutical formulations may also be used, dependent on the condition to be treated.

As described in detail herein, it is contemplated that certain benefits will result from the manipulation of the agents for use in the present invention, such as copper binding or complexing thiomolybdates, to provide them with a longer in vivo half-life. Slow release formulations are generally designed to give a constant drug level over an extended period. Increasing the half-life of a drug, such as agents for use in the present invention, such as copper binding or complexing thiomolybdates, is intended to result in high plasma levels of TM upon administration, which levels are maintained for a longer time, but which levels generally decay depending on the pharmacokinetics of the construct. Slow release formulations of the instant compositions and combinations thereof are contemplated for some uses in the present invention.

Appropriate solutions of the agents for use in the present invention, such as copper binding or complexing thiomolybdates, of which tetrathiomolybdate is an example, pharmaceutical forms suitable for administration, compositions comprising the agents, formulations with the agents, and carriers may be similar to those described below.

B. Parenteral Formulations

In addition to the compounds formulated for parenteral administration, the agents for use in the present invention, such as copper binding or complexing thiomolybdates, may be formulated for parenteral administration, e.g., formulated for injection via the intravenous, intramuscular, sub-cutaneous or other such routes, including direct instillation into a disease site. The preparation of an aqueous composition that contains one or more agents for use in the present invention, such as copper binding or complexing thiomolybdates, as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as freebase or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form should be sterile and should be fluid to the extent that easy flow through a syringe exists. It should be stable under the conditions of manufacture and storage and must be preserved against the contaminating action of microorganisms, such as bacteria and fungi.

Compositions comprising the agents for use in the present invention, such as copper binding or complexing thiomolybdates, can be formulated into a composition in a neutral or salt form. Pharmaceutically acceptable salts have been described above.

The carrier can also be a solvent or dispersion medium containing, for example, water, ethanol, polyol (for example, glycerol, propylene glycol, and liquid polyethylene glycol, and the like), suitable mixtures thereof, and vegetable oils. Proper fluidity can be maintained, for example, by the use of a coating, such as lecithin, by the maintenance of the required particle size in the case of dispersion and by the use of surfactants. Prevention of the contamination with microorganisms can be obtained by various antibacterial and antifungal agents, for example, parabens, chlorobutanol, phenol, sorbic acid, thimerosal, and the like. In many cases, it may be desirable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. Formulations are easily administered in a variety of dosage forms, such as the type of injectable solutions described above, but drug release capsules and the like can also be employed.

Suitable pharmaceutical compositions in accordance with the invention will generally include an amount of one or more of the agents for use in the present invention, such as copper binding or complexing thiomolybdates, admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. It should be appreciated that endotoxin contamination should be kept minimally at a safe level, for example, less that 0.5 ng/mg protein. Moreover, for human administration, preparations should meet sterility, pyrogenicity, general safety and purity standards as required by FDA Office of Biological Standards.

The therapeutically effective doses are readily determinable using an animal model, as shown in the studies detailed herein. Experimental animals with induced inflammatory and/or fibrotic diseases are frequently used to optimize appropriate therapeutic doses prior to translating to a clinical environment. Such models are known to be very reliable in predicting effective anti-inflammatory or anti-fibrotic strategies. For example, bleomycin mice, such as described in Example 1, are appropriate models of pulmonary fibrosis in humans. One can use such art-accepted mouse models to determine working ranges of agents for use in the present invention, such as copper binding or complexing thiomolybdates, that give beneficial anti-inflammatory and/or anti-fibrotic effects with minimal toxicity.

C. Therapeutic Kits

The present invention also provides therapeutic kits comprising agents for use in the present invention which bind or complex copper, such as thiomolybdates, and of which tetrathiomolybdate is an example, as described herein. Such kits generally comprise, in suitable container means, a pharmaceutically acceptable formulation of at least one agent for use in the present invention, such as copper binding or complexing thiomolybdates, in accordance with the invention. The kits may also comprise other pharmaceutically acceptable formulations, such as any one or more of a range of anti-inflammatory and/or anti-fibrotic drugs.

The kits may have a single container means comprising an agent that binds or complexes copper, such as a thiomolybdate, with or without any additional components, or they may have distinct container means for each desired agent. In some embodiments, kits of the present invention comprise an agent for use in the present invention, such as copper binding or complexing thiomolybdates, packaged in a kit for use in combination with the co-administration of a second agent, such as an anti-inflammatory or anti-fibrotic agent as described above. In such kits, the components may be precomplexed, either in a molar equivalent combination, or with one component in excess of the other; or each of the components of the kit may be maintained separately within distinct containers prior to administration to a patient.

When the components of the kit are provided in one or more liquid solutions, the liquid solution is generally an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent may also be provided in another container means. One of the components of the kit may be provided in capsules for oral administration.

The container means of the kit will generally include at least one vial, test tube, flask, bottle, syringe or other container means, into which an agent for use in the present invention, such as copper binding or complexing thiomolybdates, and any other desired agent, may be placed and, preferably, suitably aliquoted. Where additional components are included, the kit will also generally include a second vial or other container into which these additional components are placed, enabling the administration of separated designed doses. The kits may also comprise a second and/or third container means for containing a sterile, pharmaceutically acceptable buffer or other diluent.

The kits may also comprise a means by which to administer an agent for use in the present invention, such as copper binding or complexing thiomolybdates, to an animal or human patient, e.g., one or more needles or syringes, or even an eye dropper, pipette, or other such like apparatus, from which the formulation may be injected into the animal or applied to a feeding tube or ingested orally. The kits of the present invention will also typically include a means for containing the vials, or such like, and other component, in close confinement for commercial sale, such as, e.g., injection or blow-molded plastic containers into which the desired vials and other apparatus are placed and retained.

For human use, in preferred embodiments, the kits further comprise appropriate instructions and labels (e.g., as required by the FDA) for use of copper binding or complexing agents as described herein.

X. Inflammatory Disease, Fibrotic Diseases, Injury Response, and Treatment Thereof The compositions and methods provided by this invention are broadly applicable to the treatment of any inflammatory and/or fibrotic disease, which includes response to injury. In some embodiments, the inflammatory and/or fibrotic disease is a result of the activation or over-activation of transforming growth factor beta ($TGF_\beta$). Exemplary fibrotic diseases that may be treated by a method of the present invention include, but are not limited to, pulmonary disease including pulmonary fibrosis and acute respiratory distress syndrome, liver disease including liver cirrhosis and hepatitis C, kidney disease including renal interstitial fibrosis, scleroderma, cystic fibrosis, pancreatic fibrosis, keloid, secondary fibrosis in the gastrointestinal tract, hypertrophic burn scars, myocardial fibrosis, Alzheimer's disease, retinal detachment inflammation and/or fibrosis resulting after surgery, and graft versus host and host versus graft rejections.

Currently, most of these diseases do not have an effective treatment. However, even if another treatment is perceived to exist in connection with a certain category of patients or for a certain type of disease, the perceived treatment does not in any way negate the basic utility of the methods of the present invention in connection with the treatments of all patients having an inflammatory and/or fibrotic disease.

It is contemplated that the methods of the present invention are widely or entirely applicable to the treatment of all inflammatory and/or fibrotic diseases, irrespective of the particular phenotype or localization of the inflammation or fibroses themselves. However, the particular type of disease may be relevant to the use of the methods of the present invention in combination with secondary therapeutic agents, as described above.

It is further contemplated that certain types of inflammatory and/or fibrotic diseases may be more amenable to treatment with a method of the present invention. Thus, some diseases may respond to treatment with less effect on inflammation and/or fibrosis. Although it is not necessary to understand the underlying mechanism, and the invention is not intended to be limited to any particular mechanism, it is contemplated that this might be due to slight differences in the cytokine and other pathogenic mechanisms from one disease to another. This phenomena is observed in experimental animals, and may occur in human treatments. Such considerations are taken into account in conducting both the pre-clinical studies in experimental animals and in optimizing the doses for use in treating any particular patient or groups of patients.

There are realistic objectives that may be used as a guideline in connection with pre-clinical testing before proceeding to clinical treatment. However, this is generally more a matter of cost-effectiveness than overall usefulness, and is a means for selecting the most advantageous compounds and doses. In regard to their basic utility, any composition or combination comprising a copper binding or complexing agent such as thiomolybdate that results in any consistent anti-inflammatory and/or anti-fibrotic effects defines a useful compound. Even in those circumstances where the anti-inflammatory and/or anti-fibrotic effects are towards the low end of the range, it may be that the therapy of the present invention is as or even more effective than other known therapies in the context of particular anti-inflammatory and/or anti-fibrotic targets, and especially where other factors (such as desirable or undesirable side effects, or quality of life) may be important. Even if it becomes evident to the clinician that particular anti-inflammatory and/or anti-fibrotic diseases cannot be effectively treated in the intermediate or long term, it does not negate the utility of the therapy of the present invention, particularly where it is about as effective as other known strategies, or where it is effective after other conventional therapies have failed. It is not predicted that resistance to therapy of the present invention can develop.

In the present invention, an agent that binds or complexes copper such as a thiomolybdate is administered in a therapeutically effective amount to a patient suffering from an inflammatory and/or fibrotic disease. The term "therapeutically effective amount" is a functional term referring to an amount of material needed to make a qualitative or quantitative change in a clinically measured parameter for a particular subject. For example, prior to administration, the subject may exhibit measurable symptoms of disease (for example, pulmonary congestion and/or difficulty breathing; evidence of hepatitis, or decrease in liver function; evidence or kidney inflammation or decrease in kidney function; etc), which upon administration of a therapeutically effective amount the measurable symptom is found to change over time. A therapeutically relevant effect relieves to some extent one or more symptoms of a disease or condition or returns to normal either partially or completely one or more physiological or biochemical parameters associated with or causative of the disease.

In particular, the term refers to an amount of an agent that binds or complexes copper such as thiomolybdate effective to treat an inflammatory and/or fibrotic disease upon administration to a patient suffering from such a disease. Treatment includes but is not limited to preventing the onset or shortening the course or severity of or reversing the effects of inflammatory and/or fibrotic disease; thus, a therapeutically effective amount includes a prophylactically effective amount. Such effects are achieved while exhibiting negligible or manageable adverse side effects on normal, healthy tissues of the patient. Thus, the "therapeutically effective amount" can vary from patient to patient, depending upon a number of factors, including but not limited to the type of disease, the extent of the disease, and the size of the patient.

An objective of the therapeutic regimes of the present invention is to reduce the endogenous copper level to a target level, and then to maintain that level for a period of time sufficient to prevent the onset or to shorten the course or severity of or to reverse the effects of inflammatory and/or fibrotic disease. The period of time sufficient to both reduce endogenous copper level and to maintain it to prevent the onset or to shorten the course or severity of or to reverse the effects of inflammatory and/or fibrotic disease is referred to as a "therapeutically effective time". As described earlier, the level of endogenous copper can be monitored by measuring blood ceruloplasmin (Cp) levels. In some embodiments, the levels of blood ceruloplasmin decrease by 10%; in other embodiments, these levels decrease by about 25%; in yet other embodiments, these levels decrease by about 50%; in still other embodiments, these levels decrease by about 90%. Alternatively, ceruloplasmin levels decrease to between about 5 to 15 mg/dl. The time period in which to reduce endogenous copper levels will vary, depending upon the disease and the patient's general health and condition; typically, this time depends upon the amount of copper-binding agent per dose, and frequency of dose administration per treatment period. Generally, for acute diseases, such as ARDS, it is desirable to decrease endogenous copper levels as rapidly as possible; this is because patients are at risk of dying quickly, and it is therefore desirable to initiate quick intervention. Under these circumstances, it is preferable to use initially a much higher loading dose of a copper-binding or complexing agent than might be used for a chronic disease or condition. For both acute and chronic diseases, initial doses of copper binding or complexing agents might be higher and administered more frequently in order to fairly rapidly decrease endogenous copper to the target levels; these doses are referred to as induction doses. Subsequent doses of copper binding or complexing agents to maintain endogenous copper at the target level may be lower, and administered less frequently; these doses are referred to as maintenance doses.

In designing appropriate doses of the agents that bind or complex copper such as thiomolybdate and combinations therewith, and/or that effectively lower endogenous copper, one may readily extrapolate from animal studies, as for example as described further below, in order to arrive at appropriate doses for clinical administration. To achieve this conversion, one would account for the mass of the agents administered per unit mass of the experimental animal, and yet account for the differences in the body surface area between the experimental animal and the human patient. All such calculations are well-known and routine to those of ordinary skill in the art. Accordingly, using the information provided herein, it is contemplated that useful daily doses of the agents that bind or complex copper such as thiomolybdate, and/or that effectively lower endogenous copper, for use in human administration would be between about 20 mg and about 200 mg per patient per day. Notwithstanding this stated range, it is contemplated that, given the parameters and guidance described above, further variations in the active or optimal ranges are encompassed within the present invention.

Induction doses contemplated are generally about 180 mg per day. Daily maintenance doses contemplated are generally between about 20 mg and about 180 mg; between about 25 and about 160 mg; between about 50 and about 150 mg; between about 30 and about 125 mg; between about 40 mg and about 100 mg; between about 35 and about 80 mg; between about 20 and about 65 mg; between about 30 mg and about 50 mg; about 40 mg; or in any particular range using any of the foregoing recited exemplary doses or any value intermediate between the particular stated ranges. Although daily doses in and around about 60 mg to about 120 mg, or in and around about 20 to about 180 mg, are typical, it is contemplated that lower doses may be more appropriate in combination with other agents, or under conditions of maintenance, and that high doses can still be tolerated, particularly given the fact that the agents that bind or complex copper such as a thiomolybdate and/or that effectively lower endogenous copper for use in the invention are not themselves cytotoxic. Even if certain adverse side effects do occur, this should not necessarily result in toxicity that cannot be counteracted by normal homeostatic mechanisms, which is believed to lessen the chances of significant toxicity to healthy tissues.

The values described above can also be expressed in terms of mg/kg of body weight. As described above, the biologically or therapeutically effective amount can vary, depending upon the size of the animal or human patient. However, taking the average weight of a human male as about 70 kg, the biologically or therapeutically effective amount of the agent that binds or complexes copper such as a thiomolybdate for an average human male would be between about 0.3 mg/kg and about 3 mg/kg.

Another objective of the therapeutic regimes of the present invention is generally to produce the maximum anti-inflammatory and/or anti-fibrotic effects while keeping the dose below the levels associated with unacceptable toxicity. However, as noted above, in acute diseases or conditions, it may be necessary to administer initial high doses to rapidly decrease endogenous copper levels. In addition to varying the dose itself, the administration regimen can also be adapted to optimize the treatment strategy. A currently preferred maintenance treatment strategy is to administer between about 20 mg and about 200 mg of the agents that bind or complex copper such as a thiomolybdate or combination thereof, or which effectively lower endogenous copper, from about 3 to about 6 or more times per day, approximately half of the doses with meals, and approximately half of the doses between meals. In administering the particular doses themselves, one would preferably provide a pharmaceutically acceptable composition to the patient systemically. Oral administration is generally preferred. An exemplary induction dosage regime for a patient suffering from a chronic inflammatory and/or fibrotic disease is about 40 mg three times daily with meals, and about 60 mg at bedtime. Exemplary maintenance dosage regimes for a patient suffering from a chronic inflammatory and/or fibrotic disease is about 20 to 180 mg total per day, taken approximately proportionately as indicated for the exemplary induction dosage regime, or taken at fewer times per day, for example, with breakfast and with dinner.

XI. Efficacy of Tetrathiomolybdate in Lowering Endogenous Copper

Prior Use to Treat Wilson's Disease

The efficacy and safety of tetrathiomolybdate to lower endogenous copper levels in both animal and human patients has been well documented in its use to treat Wilsons's disease, which is characterized by an increase in endogenous levels of copper, generally to toxic levels. A description of Wilson's disease, previous therapy regimes, the discovery of tetrathiomolybdate, it's toxicity and efficacy, both alone and in comparison to other anti-copper agents, and its utility in treating Wilson's disease, are provided below as part of the description of the methods of the present invention.

A. Wilson's Disease and its Existing Treatments

Wilson's disease is an autosomal recessive disorder of copper metabolism. In this disorder, the excretion of copper into the bile appears to be defective, and there is reduced hepatic incorporation of copper into ceruloplasmin, leading to an accumulation of toxic levels of copper in plasma and most body tissues. Wilson's disease usually leads to hepatic and/or neurologic dysfunction.

The therapy of Wilson's disease can be divided into two broad categories (G J Brewer and Yuzbasiyan-Gurkan, Medicine, 71(3):139-164 [1992]; and G J Brewer, Wilson's Disease: A Clinician's Guide to Recognition, Diagnosis, and Management (Kluwer Academic Publishers, Boston) [2001]). These two categories are initial therapy in acutely ill patients, and maintenance therapy. Initial therapy is that period of time during which a newly presenting patient is still suffering from acute copper toxicity, generally the first few weeks to months of therapy. Maintenance therapy is essentially the rest of the patient's life, or that period of time after the copper levels have been brought down to a subtoxic threshold, and the patient is on therapy simply to prevent the recurrence of copper accumulation and copper toxicity.

For the maintenance therapy of Wilson's disease, three drugs were previously used. These include the oldest available drug, penicillamine (Walshe, Am. J. Med., 21:487 [1956]), a drug called trien or trientine which was developed for patients who are intolerant of penicillamine (Walshe, Lancet, 1:643-647 [1982]), and zinc acetate (G J Brewer and Yuzbasiyan-Gurkan, Medicine, 71(3): 139-164 [1992]; Brewer and Yuzbasiyan-Gurkan, in Textbook of Clinical Neruopharmacology and Therapeutics, $2^{nd}$ Edition (Klawans, Goetz, Tanner, eds; Raven Press, New York; pp. 191-205 [1992]); G J Brewer et al., Annals. Int. Med., 99:314-320 [1983]; Hill et al., Hepatology, 7:522-528 [1987]; Hill et al., Am. J. Med. Sci., 12:344 [1986]; Brewer et al. (1987) J. Lab. Clin. Med. 109:526-531; Brewer et al. (1987) Proc. Soc. Exper. Biol. Med. 7:446-455; Brewer et al. (1987) Sem. Neurol. 7:209-220; Yuzbasiyan-Gurkan et al. (1989) J. Lab. Clin. Med. 114:520-526; Brewer et al. (1989) J. Lab. Clin. Med. 114:633-638; Lee et al. (1989) J. Lab. Clin. Med. 114:639-645; Brewer et al. (1990) J. Trace Elem. Exp. Med. 3:227-234; Brewer et al. (1991) J. Lab. Clin. Med. 118:466-470; Brewer and Yuzbasiyan-Gurkan (1989) Dig. Dis. 7(4): 178-1923; Brewer et al. (1992) JAVMA 201:564-568; G J Brewer et al., J. Vet. Int. Med., 6:41-43 [1992]; Yuzbasiyan-Gurkan et al., J. Lab. Clin. Med., 120:380-386 [1992]; Brewer et al., J. Amer. Coll. Nut., 12(1):26-30 [1993]; G J Brewer et al., Amer. J. Med. Sci., 305(4):199-202 [1993]; In Essential and Toxic Trace Elements in Human Health and Disease: An Update (Prasad, ed; Allan R. Liss, New York; PCBR 380:129-145), G J Brewer et al., J. Lab. Clin. Med., 123:849-858 [1993]; G J Brewer, Nutrition and the MD, 19(12) [1993]; Hoogenraad et al., Lancet, 2:1262-1263 [1978]; Hoogenraad et al., Eur. Neurol., 18:205-211 [1979]; Hoogenraad et al., J. Neurol. Sci., 77:137-146 [1987]). In the past, it was generally believed that zinc provided an effective maintenance therapy with a very low level of toxicity.

About two thirds of patients who present with Wilson's disease present with symptoms referable to the brain (G J Brewer et al., JAMA, 201:564-568 [1992]; Scheinberg and Sternlieb, In: Major Problems in Internal Medicine, Vol. XXIII (W.B. Saunders Company, Philadelphia) [1984]; and Danks, In: Metabolic Basis of Inherited Diseased, Vol. 1, Sixth Ed. (Scriver, Beaudet. Sly, Valle, eds; McGraw Hill, New York; pp. 1411-1431 [1989]; and G J Brewer, Wilson's Disease: A Clinician's Guide to Recognition, Diagnosis, and Management (Kluwer Academic Publishers, Boston [2001]). These can be neurologic symptoms or symptoms of psychiatric nature in the beginning, with neurologic symptoms later. Therapy for these patients was not nearly as straightforward as it was for maintenance phase patients. It was found that approximately 50% of these patients who were treated with penicillamine became worse rather than better (G J Brewer et al., Arch. Neurol., 44:490-494 [1987]). Half of these patients who worsen, or about 25% of the original sample, never recovered to their pre-penicillamine baseline. In other words, penicillamine induced additional irreversible damage.

The mechanisms underlying this worsening are not known with certainty, although it is likely that the mobilization of hepatic copper by the drug further elevates brain copper. The inventors have shown that this mechanism can occur in a rat model. Regardless of the mechanism, neurologically presenting patients very often ended up much worse after being treated initially with penicillamine. In fact, even presymptomatic patients could develop neurologic disease after being initiated on penicillamine (Glass et al., Arch. Neurol., 47:595-596 [1990]; and G J Brewer et al., Arch. Neurol., 51:304-305 [1994]). It was not known whether trientine exhibits the phenomenon of neurological worsening when used as initial therapy, because it has not been used very much in this kind of situation. It would not be surprising if trientine exhibited this problem to some degree, because its mechanism of action is believed to be similar to that of penicillamine; however, it is anticipated that the problematic effects of trientine would be less serious, as its effects on copper seem to be somewhat gentler.

Zinc is not an ideal agent for the initial treatment for this type of patient. Zinc has a relatively slow onset of action, and produces only a modest negative copper balance. Thus, during the several months required for zinc to bring copper down to a subtoxic threshold, patients may be at risk for further copper toxicity and worsening of their disease.

B. Tetrathiomolybdate

The discovery of TM began with observations of cattle and sheep which developed copper deficiency when grazing on pasturages with high molybdenum (Mo) content (Ferguson et al., J. Agr. Sci., 33:44 [1943]; Dick and Bull, Aust. Vet. J., 21:70 [1945]; Miller and Engel, Fed. Proc., 19:666 [1960]). It was established that administration of supplementary Mo impaired copper metabolism in ruminants (Macilese Ammerman et al., J. Nutr., 99:177 [1969]); however, Mo had little effect on non-ruminant animals such as rats (Mills et al., J. Nutr., 65:129 [1958]; Cox et al., J. Nutr., 70:63 [1960]). The answer to the different effects of Mo came from observations which suggested that the administered Mo was converted to thiomolybdates in the rumen as a result of the high sulfide metabolism there, and that thiomolybdates were the active anti-copper agents (Dick et al., J. Agri. Sci., 85:567 [1975]). This theory was confirmed when thiomolybdate compounds were given to rats and produced anti-copper effects (Mills et al., J. Inorg. Biochem., 14:189 [1981]; Mills et al., J. Inorg.

Biochem., 14:163 [1981]; and Bremner et al., J. Inorg. Biochem., 16:109 [1982]). The tetra-substituted compound, tetrathiomolybdate or TM, appeared to be the most potent of the thiomolybdates initially tested.

The anti-copper effects TM are believed to be based upon two modes of action of TM (Mills et al., J. Inorg. Biochem., 14:189 [1981]; and Mills et al., J. Inorg. Biochem., 14:163 [1981]; Bremner et al., J. Inorg. Biochem., 16:109 [1982]; and Gooneratne et al., Br. J. Nutr., 46:469 [1981]). One mechanism operates in the gastrointestinal or GI tract, and the other in the blood. In the GI tract, TM forms complexes with copper and food proteins (or other proteins) that are not absorbed. This absorption block involves not only food copper, but also the rather considerable amount of endogenously secreted copper in saliva, gastric juice and other GI tract secretions (Allen and Solomons, In: Absorption And Malabsorption Of Mineral Nutrients, Solomons and Rosenberg (Eds.) Alan R. Liss, Inc., New York, 12:206 [1984]). Although both TM and zinc are apparently effective in the GI tract, TM offers several advantages over zinc. One advantage is that TM is a more effective blocker of copper absorption than zinc, because zinc acts only in those areas of the small intestine where metallothionein can be induced (Yuzbasiyan-Gurkan et al., J. Lab. Clin. Med., 120:380-386 [1992]), where in contrast, TM is effective the entire length of the GI tract. Another advantage of TM over zinc is that TM acts immediately; therefore, it does not have a lag period required for the induction of metallothionein.

The second mode of action of TM is in the blood. TM given at times away from meals is relatively well absorbed into the blood. There it forms complexes with copper and albumin, rendering the complexed copper unavailable for cellular uptake (Gooneratne et al., Br. J. Nutr., 46:469 [1981]). The normal plasma copper is in two primary pools. Most of the plasma copper in normal persons is part of the ceruloplasmin molecule. This copper is essentially unavailable for ready exchange with cells and is considered non-toxic. The other pool of copper is more loosely bound to albumin and small molecules, such as amino acids. This pool of copper is greatly expanded during acute copper toxicity in Wilson's disease, and is readily available for cellular uptake and is, therefore, potentially toxic (Scheinberg and Sternlieb (1984) In: Major Problems In Internal Medicine, Vol. XXIII, Saunders Company, Philadelphia). When TM enters the blood, it complexes with this latter copper and renders it, like the ceruloplasmin copper, unavailable for cellular uptake and for further toxicity.

Very good evidence exists that TM-complexed copper is unavailable for cellular uptake. The most direct evidence is that in sheep levels of copper in the plasma which would normally be high enough to produce hemolytic anemia do not do so in the presence of TM (Gooneratne et al., Br. J. Nutr., 46:469 [1.981]). It was shown that the TM bound copper does not permeate the erythrocyte. This is direct evidence that TM-complexed copper does not permeate cells.

C. Tetrathiomolybdate Toxicity and Efficacy

Considerable work on the potential toxicity of TM has been carried out in rats (Mills et al., J. Inorg. Biochem., 14:189 [1981]; and Bremner et al., J. Inorg. Biochem., 16:109 [1982]). Approximately 6 mg of TM per kilogram of diet shows substantial effects on copper levels in rats, including a reduction of plasma ceruloplasmin and a reduction in liver and kidney copper. At approximately 12 mg of TM, all of these changes were increased and, in addition, liver Mo was increased. Mild anemia was present, and skeletal lesions were present in one of six animals. At approximately 18 mg of TM, the anemia was severe. Melanogenesis of hair was impaired, diarrhea was present, growth rate was markedly impaired, and all animals had skeletal lesions characterized by dysplasia in the epiphyseal cartilage cells of long bones, resorption of trabecular bone, and structural changes in ligaments.

It was later shown that all of the toxic effects of TM, up to 36 mg of TM per kilogram of diet, could be prevented by oral supplementation with copper, or with intraperitoneal injection of copper (Mills et al., J. Inorg. Biochem., 14:163 [1981]). Thus, it appears that all the toxic lesions induced by TM are due to copper deficiency induced by the TM. In support of this hypothesis, almost all of the above lesions are induced by dietary copper deficiency, the two exceptions being the skeletal lesions and the enterocyte mitochondrial damage which leads to diarrhea. The reason that these last two lesions are seen with TM administration, but may not be seen in dietary copper deficiency, could be related to the severity and the rapidity of the copper deficiency induced by TM. With dietary copper deficiency, there is always some contaminating copper available, and rapidly dividing cells such as the enterocyte and epiphyseal cells may obtain enough copper to prevent the lesions. The prevention of these two lesions as well as all of the other TM induced lesions by copper supplementation indicates that the lesions are probably due to copper deficiency.

Other publications reported the results of examining gut pathology in rats receiving approximately 18 mg of TM per kilogram of diet (Fell et al., J. Com. Pathol., 89:496 [1979]). These rats also received approximately 3 mg of copper per kilogram of diet. In these rats, observed gut pathology involving cell apoptosis, edema, and necrosis was attributed to hypocuprosis, although this was not proven. It is probable that a higher copper supplement was required for protection, in view of the observations that all such problems were prevented by adequate copper supplementation (Mills et al. J. Inorg. Biochem., 14:163 [1981]).

Wilson's disease patients have a huge store of excess copper, so none of the TM toxicities due to copper deficiency are a risk in these patients. Even in the case of the skeletal and enterocyte lesions, since copper administration is protected, the Wilson's disease patient with excessive stores of copper should also be protected.

The effect of TM on copper loaded sheep has also been studied (Gooneratne et al., Br. J. Nutr., 46:457 [1981]). It is well known that sheep are quite susceptible to copper toxicity, usually developing hepatic failure and hemolytic anemia. The studies involved loading sheep dietarily with copper to the point of initiation of hepatic damage, then giving TM intravenously in doses of 50 or 100 mg 2×weekly for up to 11 weeks. Five of the 26 sheep died during the study. All deaths were attributed to copper toxicosis based on autopsy results. Three of the five deaths occurred in control animals who received copper but not TM. One death occurred after an animal had received only one dose of TM, and another in an animal who had received only 4 doses of TM. It is clear that these two animals died from copper toxicity prior to the ability of TM to rescue them. If animals survived the initial onset of copper toxicosis, they were protected from further copper toxicity by TM, even though in some cases copper administration was continued. These animals tolerated up to 22 injections of TM without clinical problems.

Support for the beneficial effect of administering TM by either intravenous injection (Humphries et al., Vet. Record, 119:596-598 [1986]) or by subcutaneous injection (Humphries et al., Vet. Record, 123:51-53 [1988]) in protecting sheep against severe hepatic copper toxicity has also been shown. TM not only reduced the amount of hepatic copper, but the actual liver damage. TM was also used prophylactically to prevent copper toxicity in commercial sheep flocks. Over 400 animals have been treated with TM with no adverse side effects (Humphries et al., Vet. Record, 123:51-53 [1988]).

Preliminary work also indicated that TM may be dramatically effective against copper toxicity in the LEC rat model (Suzuki et al., TOXIC, 83:149 [1993]). The genetic defect in these rats has been recently shown to be due to a defect in the Wilson's disease gene (Wu et al., Nat. Genet., 7:541 [1994]). These rats develop severe liver disease and usually die. TM has been very effective in treating these animals in the late stages of their liver disease.

Molybdenum metabolism in sheep has been studied after the intravenous injection of $^{99}$Mo labeled TM (Mason et al., J. Inorg. Biochem., 19:153 [1983]). There was a rapid disappearance from plasma during the initial 15 minutes, and then a slow disappearance with a half-time of about 40 h. The TM was transformed step wise to molybdate, and over 90% was excreted in urine compared to 5% in feces. The same group published subsequently on $^{99}$Mo and $^{35}$S metabolism after intravenous injection of double labeled TM in sheep (Hynes et al., Brit. J. Nutr., 52:149 [1984]). Most of the $^{99}$Mo and $^{35}$S were associated initially with albumin. Displaced or unbound TM was rapidly hydrolyzed to molybdate and sulfate. There was no evidence of an irreversible interaction of either $^{35}$S or $^{99}$Mo with copper and plasma despite the appearance of a TCA insoluble copper fraction.

It is clear that in the presence of high levels of copper, TM administration results in the accumulation of copper complexed with TM in both the liver and kidneys (Jones et al., Res. Vet. Sci., 37:273 [1984]; and Bremner and Young, Br. J. Nutr., 39:325 [1978]). However, there is no evidence of a storage disease associated with this complex. Current theory holds that the complex is disassociated and that the TM is metabolized to oxymolybdates and excreted (Mason et al., J. Inorg. Biochem., 19:153 [1983]). The copper then enters other pathways in the liver. In the presence of high levels of metallothionein, the copper would most likely be taken up by metallothionein. In the kidneys, the evidence is that the copper is simply excreted.

Two cases of reversible bone marrow depression have been reported in patients receiving TM for maintenance therapy (Harper and Walshe, Br. J. Hematol., 64:851-8 [1986]). The inventors have observed reversible anemia in seven patients. These patients had a strong response to therapy, and likely ended up with localized, bone marrow copper deficiency. Since copper is required for heme synthesis, this appears to be a manifestation of over-treatment, at least as far as the bone marrow is concerned. Since TM is such an effective anticopper agent, it would not be unexpected for over-treatment to occur during maintenance therapy with TM, as was previously observed (Harper and Walshe, Br. J. Hematol., 64:851-853 [1986]).

D. Molybdenum (Mo) Toxicity

About 37% of TM is Mo. The normal intake of Mo is about 350 μg/day (Seelig, Am. J. Clin. Nutr., 25:1022 [1972]), or the equivalent amount of Mo that would be in about 1.0 mg of TM. Molybdenum seems to be quite well tolerated by the human. Relatively high doses of 5-20 mg/kg/day of Mo (equivalent to the Mo in 1-4 g of TM) were used for 4-11 months in patients with Wilson's disease in a 1957 study, without known toxicity (Bickel et al, Quart. J. Med., 50:527 [1957]). However, it was not effective, because as pointed out earlier, TM is the active metabolite, and that is formed efficiently from Mo only in ruminants.

E. Additional Anti-Copper Drugs

1. Penicillamine

Penicillamine is the drug that has been used the most, and is the best known. However, it should be the last choice for initial treatment of patients suffering from neurological symptoms because of the very high risk of worsening their neurologically symptoms (G J Brewer et al., Arch. Neurol., 44:490-494 [1987]; and G J Brewer et al., Arch. Neurol., 51:304-305 [1994]). Another problem with penicillamine is that about a quarter to a third of patients develop an initial hypersensitivity syndrome which requires significant interventions, such as temporarily stopping the drug and restarting it at a lower dose, usually with concurrent corticosteroid administration. This is a somewhat frightening experience for patients who are already ill, and prevents the attending physician in the inventors' study from being blinded. Finally, there is a long list of other side effects that can occur with penicillamine during the first few weeks of therapy. These include bone marrow depression, proteinuria, and auto-immune disorders.

2. Zinc

Zinc was used for the comprehensive treatment of Wilson's disease including initial treatment (Hoogenraad et al., Lancet, 2:1262-1263 [1978]; Hoogenraad et al., Eur. Neurol., 18:205-211 [1979]; and Hoogenraad et al., J. Neurol. Sci., 77:137-146 [1987]). However, zinc was not ideal for initial therapy (by itself) because it is rather slow acting. Thus, it takes approximately two weeks to achieve intestinal metallothionein induction and a negative copper balance in Wilson's patients (Yuzbasiyan-Gurkan et al., J. Lab. Clin. Med., 120:380-386 [1992]). At the two week point, zinc immediately reverses the +0.54 mg daily (positive) copper balance these patients average, but the negative copper balance induced is rather modest, averaging -0.35 mg daily (negative) copper balance (G J Brewer et al., J. Trace Elem. Exp. Med., 3:227-234 [1990]; G J Brewer et al., Amer. J. Med. Sci., 305:(4)199-202 [1993]Due to this low rate of copper removal, it takes as long as six months of zinc therapy to bring urine copper and nonceruloplasmin plasma copper (the potentially toxic copper measured in the blood), down to subtoxic levels.

TM is a more effective blocker of copper absorption than zinc, since zinc acts only in those areas of the small intestine where metallothionein can be induced. In contrast, TM works all up and down the gastrointestinal track. The other advantage of TM over zinc in this setting is that TM acts immediately. It does not have a lag period required for the induction of metallothionein.

3. Trientine

Trientine acts by chelation and urinary excretion of copper (Walshe, Lancet, 1:643-647 [1982]). A therapeutic dose (1,000-2,000 mg/day) usually produces only about half as much cupruresis as a similar dose of penicillamine. Nonetheless, trientine is capable of an initial production of a several mg negative copper balance, much greater than zinc. Typically, this 4-5 mg cupruresis decreases during the first few weeks of therapy to a more modest, but still substantial, 2-3 mg. Ingestion of copper is about 1 mg/day, with obligatory, non-urine losses of about 0.5 mg. Thus a cupruresis of 2-3 mg produces a negative copper balance of 1.5 to 2.5 mg/day.

Trientine is officially approved for use in patients intolerant of penicillamine therapy. Because of this, and because it was introduced much later than penicillamine, it has not been used and reported on very extensively. It has not had a formal toxicity study. It appears to have substantially less risk of side effects then penicillamine. An initial hypersensitivity problem has not been reported. It does cause proteinuria, after several weeks of use in about 20% of patients. It can also occasionally produce bone marrow depression and autoimmune abnormalities, although the latter is usually after prolonged use.

So far, trientine has not been reported to cause initial worsening in neurological patients, but its sole use in this type of patient is probably very limited. Anecdotally, the inventors have received patients in transfer who worsened on penicillamine, were switched briefly to trientine, and when they became worse (or failed to improve) were transferred to the inventors for TM therapy. In patients with this history, it is impossible to know if trientine played any role in worsening. Theoretically, it could, because as with penicillamine, trientine mobilizes copper, producing a higher blood level to achieve urinary excretion. But whether this increased level of blood copper translates into increased brain levels, and increased neurotoxicity, is unknown.

XII. Results of Tetrathiomolybdate Therapy for Wilson's Disease

Over a period of several years, the inventors carried out an open label study of the use of TM for initial treatment of neurologically presenting Wilson's disease patients. The inventors also developed both a spectrophotometric and bioassay for the activity of the drug, to evaluate its stability and to assure its potency when administered (G J Brewer et al., Arch. Neurol., 48(1):42-47 [1991]; and G J Brewer et al, Arch. Neurol., 51(6):545-554 [1994]). As noted above, TM is unstable in air, and slowly loses potency when exposed to air. This is apparently due to the exchange of oxygen molecules with the sulfur molecules, rendering TM inactive.

The results in the first patient studied can be used to illustrate several points. For the first seven days, the patient received TM only with meals (tid with meals). This produced the immediate negative copper balance one would expect from the first mechanism of action (blockade of copper absorption when given with meals). After the first seven days, TM was given between meals as well (tid with meals, and tid between meals). This led to the immediate rise in plasma copper expected from absorption of TM into the blood, and formation of a complex of copper, TM, and albumin. The copper complexed with TM and albumin is unavailable for cellular uptake, and this copper is therefore non-toxic. There is a 1:1 stochiometric relationship between molybdenum and copper in this complex. Knowing the molybdenum level in the blood, and the ceruloplasmin level (ceruloplasmin also contains copper that is non-toxic), one can calculate how much of the plasma copper is not bound to one or the other. This so-called "free copper" (non-ceruloplasmin plasma copper) is the potentially toxic copper. When reduced to zero, the plasma copper-molybdenum "gap" is closed. This took 16 days in the first patient (9 days after adding the between meal doses). Since in the brain (and in other organs), free copper is in equilibrium with the blood, decreasing the blood free copper to a low level begins the process of lowering the brain level of free (toxic) copper.

The inventors have treated initially 56 Wilson's disease patients with TM, all of whom presented with neurological or psychiatric disease, in an open label study. These patients were all diagnosed by standard criteria. These patients had a diagnostically elevated hepatic or urine copper, usually both. Some of them were treated briefly with other agents prior to this trial. Two patients had psychiatric but not neurological symptoms.

With three exceptions in the earliest part of the study, all patients received a dose of 20 mg tid with meals, or qid with three meals and a snack. Thus, the only difference between a patient receiving 120 mg and 140 mg total dose is that the former was receiving 20 mg tid, or 60 mg, with meals, and the latter was receiving 20 mg qid, or 80 mg with meals plus a snack. The rest of the total daily dose was divided up into three equal doses and given between meals.

The total daily dose was varied considerably among the patients, from a high of 410 mg to a low of 120 mg. In the end, the inventors could discern no dose-related correlation with copper variables, nor with functional variables measured either during the study or at the one and two year time point.

Zinc administration was also used in these patients. The starting time of zinc administration was varied widely and did not correlate with copper variables, outcome variables or toxicity. Early zinc therapy should theoretically help preserve liver function. In these patients, liver function returned to normal by year 1, but since these tests don't measure the extent of tissue preservation, it seems likely zinc was somewhat beneficial.

Measuring trichloracetic acid (TCA) soluble copper of the plasma is somewhat useful in assessing the impact of TM therapy on copper metabolism in Wilson's disease. Generally, a high proportion of plasma copper in these patients is TCA soluble (it averaged 56% in patients which is 27 p.g/dl). All of the non-ceruloplasmin plasma copper is TCA soluble, and a somewhat variable portion of the ceruloplasmin copper is also TCA soluble. Because the ceruloplasmin levels are usually rather low in Wilson's disease, most of the plasma copper is TCA soluble. The copper in the TM/albumin/copper complex in the blood is TCA insoluble. Thus, as therapy proceeds, the fraction of the plasma copper that is TCA soluble becomes smaller. During the late stages of TM therapy, the TCA soluble fraction of plasma copper of the patients averaged 15 pg/dl, a significant reduction from the starting value of 27. The TCA soluble fraction cannot be used as an absolute endpoint, for example attempting to reduce it to zero, because a small and somewhat variable soluble fraction is usually present due to plasma ceruloplasmin. However, the significant mean reduction from 27 to 15 p.g/dl illustrates the beneficial effect that TM therapy has on the status of the potentially toxic plasma copper in these patients. Further evidence of the desirable impact of TM therapy on copper metabolism is shown by reduction of mean urine copper values during the latter part of TM therapy, compared to baseline values.

TM has a quick and favorable impact on copper metabolism, reducing the levels of potentially toxic copper of the blood and as contemplated the rest of the body as well. The primary clinical objective in treatment of Wilson's disease is to gain control over copper toxicity while not allowing worsening of the disease or symptoms. In other words, the prime objective is to protect all neurological function that is present at the time therapy is started. This was evaluated weekly by quantitative neurological and speech exams. Methodology and the neurology rating scale system have been published (Young et al., Neurol., 36:244-249 [1986]). During the weeks of TM administration, during which copper metabolism is being controlled, neurological function, as evaluated by quantitative neurological exam is protected. Only two patients (4% of the sample) showed a change of more than 5 units, the criterion for significant worsening.

During the years following induction doses which act to initially lower endogenous copper levers, while the patients are on maintenance therapy, the brain damage previously induced by copper is at least partially repaired. This is exemplified by the partial recovery in neurological scores seen at yearly time-points in follow-up. It is clear that with the initial TM approach, long-term recovery is excellent, with most patients showing substantial neurological recovery. These excellent results are to be contrasted with results observed with penicillamine therapy. As pointed out earlier, about 50% of patients initially deteriorate on penicillamine, and that half of these, or 25% of the original sample, never recover to their pre-penicillamine baseline.

The results of TM therapy on speech during the initial 8 weeks of TM therapy were evaluated by quantitative speech exams performed as described (Brewer et al., Arch. Neurol., 53:1017-1025 [1996]). During the weeks of TM administration, during which copper metabolism is controlled, neurological function as measured by quantitative speech exams is also controlled. No patient shows significant (more than 2.0 units) reduction in scores. During the following years, while the patients are on maintenance therapy, the brain damage previously induced by copper is partially repaired. This is exemplified by the partial recovery in speech scores over years of follow-up. Long-term recovery is excellent. No patient shows significantly (more than 2.0 units) less long-term function than at the time of initiation of therapy, and most show marked improvement.

Two undesirable effects from TM therapy were observed in these patients. One is a reversible anemia/bone marrow depression, which was exhibited by seven patients. The fall in hemoglobin in all of these patients was significant, averaging 3.4%. Three of the patients showed a reduction in platelet count and four of the patients showed a reduction in white blood cell count that may have been significant. TM administration was stopped in all seven cases. Except for two of the patients, stopping TM therapy occurred late in the 56-day course of TM administration.

At the time of the anemia, these patients all had zero non-ceruloplasmin plasma copper and an extremely low TCA soluble copper. The latter averaged 2.7 in these patients, and the average value for this variable in the entire group of patients was 27 at the beginning and 15 at the height of therapy. The cause of the anemia/bone marrow depression was concluded to be bone marrow depletion of copper. Since copper is required for heme synthesis and other steps in cell proliferation, it could be expected that anemia and bone marrow effect would be the first signs of copper depletion. This result from copper depletion is a well-known phenomenon.

Thus, this undesirable response to TM is not a side effect but is, rather, due to overtreatment. It is perhaps surprising that it is possible to produce even localized bone marrow copper depletion within such a short period of time in Wilson's disease, a disease in which the body is overloaded with copper. This response to TM is unique. None of the other anticopper drugs are able to produce this effect in early therapy. Thus, this speaks to the potency of TM and the rapidity with which it can control copper levels. Its also likely that the bone marrow is especially dependent on plasma copper, and that it is the first pool that it is reduced to very low levels. At a dose of 180 mg/day or over, overtreatment occurred in 6 of 37 patients. At a dose of 150 or lower, only 1 of 13 patients exhibited overtreatment, and that occurred very late (53 days in the 56 day program).

The second undesirable effect of TM therapy in these patients is an elevation of transaminase values in four of the patients. The serum AST and ALT values were elevated. TM therapy was discontinued in one patient because of these elevations. During the period of elevated serum AST and ALT values, the urine copper increases, contrary to the general trend in other patients, where it is decreasing. These data support the concept that a hepatitis is occurring, with release of copper from damaged hepatocytes. It is not clear why this hepatitis is occurring. However, untreated Wilson's disease patients have an episodic hepatitis as part of their history. Since there is little in the way of observation of untreated patients after diagnosis, no good information exists on how often episodes of transaminase elevations occur as part of the natural history of the disease.

Alternatively, the TM in some cases may be mobilizing hepatic copper at a faster rate than it can be disposed of, in which case these patients would be classified as showing a side effect of treatment. However, the observation in copper-poisoned sheep, in which the acute hepatitis, liver necrosis, and hemolytic anemia are rapidly corrected with high doses of TM, argue against this explanation. All four of these patients were treated with 150 mg TM/day or higher. None of the patients treated with 150 mg or lower exhibited this response. No other negative effects of TM have been observed.

EXAMPLES

The following examples are provided in order to demonstrate and further illustrate certain preferred embodiments and aspects of the present invention and are not to be construed as limiting the scope thereof.

In the experimental disclosures which follow, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nm (nanometers); °C. (degrees Centigrade); TM (tetrathiomolybdate); $TGF_\beta$ (transforming growth factor beta); CTGF (connective tissue growth factor); Cp (ceruloplasmin); H&E (hematoxylin and eosin); ANOVA (analysis of variance); SPARC (secreted protein, acidic and rich in cysteine); IU (international units) ; ConA (concanavlin A); ALT (alanine amino transferase) ; SF (Sigma-Frankel units)

Example 1

Treatment of Pulmonary Fibrosis in the Bleomycin Mouse Model

Several experiments were carried out in the bleomycin mouse model of pulmonary fibrosis (Experiment 1: Prophylaxis of TM Experiment; Experiment 2: Dose Response; and Experiment 3: Effect of TM as prophylaxis and treatment).

In the bleomycin mouse model, which is known to be dependent upon the $TGF_\beta$ pathway, the intratracheal administration of bleomycin leads to the development of severe lung inflammation followed by fibrosis in 2-3 weeks, at which time the mice are sacrificed. Fibrosis is quantified in lung tissue by measuring hydroxyproline, a key component of the collagen that is deposited in fibrotic lung.

The bleomycin control animals showed high levels of hydroxyproline, and severe histological inflammatory and fibrotic changes involving whole lobes, while the TM treated bleomycin mice showed no increase in hydroxyproline, and only small patches of inflammatory foci. These results are highly significant statistically.

A. Methods

Mice. Female CBA/J mice at 8-10 weeks of age were from the Jackson Laboratories (Bar Harbor, Me.). These mice weighed an average of 21.4 g at the start of experiments, with a standard deviation of 1.7 g.

Bleomycin treatment. This was undertaken on day 0 by endotracheal instillation through the oral cavity after exposure of the airway by pulling the tongue. Each mouse received 0.001 units of bleomycin (Bristol-Myers, Evansville, Ind.)/gm body weight in 30 μl of sterile saline, while control mice received an equal volume of sterile saline only.

TM treatment experiments. TM was given in 0.25 ml of water by intragastric gavage once daily, in the doses and times indicated in the various studies as described below.

Three experiments were carried out. In experiment 1, the effect of TM administered before the administration of bleomycin was examined; thus, the efficacy of TM as a prophylactic was evaluated. In experiment 2, the effect of TM at different doses after bleomycin administration was examined. In experiment 3, the effect of starting the administration of TM at various times before and after the administration of bleomycin was examined.

Copper status. In the presence of TM therapy, copper status is difficult to assess by measuring serum copper directly, since a slowly turning over tripartite complex of TM, copper, and albumin accumulates, causing the serum copper to be elevated even though availability of copper is decreasing. However, the inventors have previously determined that serum ceruloplasmin (Cp) is a good surrogate marker of copper status (G J Brewer et al., Clin. Cancer, 6: 1-10 [2000]), because the liver secretes this copper containing protein into the blood at a rate dependent upon copper availability. Copper status was followed by assaying serum ceruloplasmin (Cp), by measuring its oxidase activity (K H Schosinsky et al., Clin. Chem., 20(12)1556-1563 [1974]). Blood was obtained from the tail vein of the mice. To avoid excessive bleeding, only one mouse from each group was bled at any time point during the study, and mice were rotated so that different mice were bled at the different time points. A Cp assay in all mice was done at time of sacrifice.

Hydroxyproline assay. The extent of fibrosis was assessed by assaying hydroxyproline content of whole lung homogenates at the time of sacrifice as previously described (M Gharaee-Kermani et al., J. Leukoc. Biol., 64:657-666 [1998]). Results are expressed as μg hydroxyproline/lung (the lung tissue included both lungs).

Microscopic evaluation of the lungs. For morphological evaluation of fibrosis, lungs were inflated with formalin at the time of sacrifice, and after overnight fixation were embedded in paraffin and sections prepared for H&E staining as well as for Masson-trichrome staining for evaluation of collagen deposition as previously described (M Gharaee-Kermani et al., J. Leukoc. Biol., 64:657-666 [1998]).

Statistics. For comparisons of means, ANOVA was used followed by Scheffe's test for multiple comparisons when appropriate. For the dose-response study, regression analysis was used to evaluate statistical significance. For the third study, varying time of TM initiation, the standard error was calculated for each group and a 95% confidence interval for the mean of each group was determined.

B. Results

Experiment 1

In this experiment, the effect of TM administered before the administration of bleomycin was examined; thus, the efficacy of TM as a prophylactic was evaluated.

There were four experimental groups of five to seven mice each. Group 1 received bleomycin, group 2 was a saline control, group 3 received bleomycin and TM therapy, and group 4 was a TM therapy control. The TM was given in a dose of 0.7 mg/mouse/day beginning 7 days prior to bleomycin treatment. During days 9 to 11 after bleomycin, the TM-treated mice received 1.2 mg of TM daily, to ensure adequate lowering of copper levels, and then received 0.7 mg daily for the duration of the study. The mice were sacrificed 21 days after bleomycin treatment.

The results from Experiment 1 are shown in Table 1. At the time of sacrifice, the mean body weight of bleomycin treated animals (group 1) was significantly less than that of saline controls (group 2). TM treatment protected against some of the bleomycin induced weight loss (Table 1), as shown by the lack of a significant difference in weight between the bleomycin/TM (group 3) and the saline (group 2) means. TM alone (group 4) tended to produce some weight loss in experiment 1 (Table 1).

The mean hematocrit of bleomycin treated animals (group 1 of Table 1) was significantly increased compared to the other three groups, probably due to hemoconcentration from not drinking adequate water near the end of the 21 days.

The mean ceruloplasmin level of bleomycin/TM mice (group 3 of Table 1) was about 55% that of bleomycin animals (group 1), and the two were significantly different. TM alone (group 4) resulted in a mean ceruloplasmin about 80% of saline controls, but this difference didn't reach statistical significance.

The hydroxyproline results of experiment 1 are also shown in Table 1. Therapy with TM almost completely abrogated fibrosis as measured by this assay. Bleomycin treatment (group 1) produced a highly significant increase in hydroxyproline compared to saline controls (group 2), but there was no significant difference between the TM-treated bleomycin (group 3) and the saline group 2, and the means were very close to one another. There was a highly significant difference in the mean values between bleomycin treated (group 1) and bleomycin/TM treated (group 3) animals. In this experiment, TM alone seemed to have some effect on increasing hydroxyproline levels, an effect which wasn't borne out in experiments 2 and 3.

TABLE 1

Data from Experiment 1 at the Time of Sacrifice

| | Treatment | | | |
|---|---|---|---|---|
| | 1. Bleomycin | 2. Saline | 3. Bleomycin/TM | 4. TM |
| N | 5 | 7 | 6 | 6 |
| Weight (g) | 18.6 ± 1.4 | 24.0 ± 0.04 | 21.2 ± 0.8 | 20.4 ± 1.0 |
| Hematocrit | 55.0 ± 2.7 | 44.8 ± 0.2 | 39.7 ± 2.6 | 44.1 ± 1.0 |
| Ceruloplasmin (I.U) | 25.3 ± 2.8 | 22.7 ± 1.1 | 13.9 ± 3.3 | 18.1 ± 3.4 |
| Hydroxyproline (μg/lung) | 252 ± 16 | 156 ± 9 | 162 ± 12 | 193 ± 5 |

TABLE 1-continued

Data from Experiment 1 at the Time of Sacrifice

| | Statistical Analysis | | | | | | | |
|---|---|---|---|---|---|---|---|---|
| | Weight | | Hematocrit | | Ceruloplasmin | | Hydroxyproline | |
| | p | p* | p | p* | p | p* | p | p* |
| 1. Bleomycin versus 2. Saline | 0.001 | 0.004 | 0.001 | 0.005 | 0.183 | 0.90 | 0.001 | 0.001 |
| 1. Bleomycin versus 3 Bleomycin/TM | 0.06 | 0.32 | 0.001 | 0.001 | 0.01 | 0.06 | 0.001 | 0.001 |
| 3. Bleomycin/TM versus 2. Saline | 0.16 | 0.62 | 0.001 | 0.004 | 0.06 | 0.38 | 0.674 | 0.980 |
| 4. TM versus 2. Saline | 0.002 | 0.07 | 0.24 | 0.99 | 0.1 | 0.70 | 0.018 | 0.119 |

*p value with Scheffe's correction for multiple comparisons.

The lung histopathology results from experiment 1 bear out the hydroxyproline results. Lung sections from bleomycin-treated and bleomycin plus TM treated mice were examined by staining with H&E, and photographing at 40×, 400×, or 1000× magnification. The results indicate that while scattered patches of fibrosis and inflammatory cells could still be found in the TM-treated bleomycin animals, these were substantially smaller with lesser degrees of cellular infiltration compared to the animals treated with bleomycin alone. Sections stained with Masson-trichrome (which is a stain for collagen) revealed much less collagen deposition in the TM treated group relative to mice receiving bleomycin only.

Experiment 2

In this experiment, the effect of TM at different doses after bleomycin administration was examined. Experimental groups of four bleomycin-treated and two to four control (non-bleomycin treated) mice were given varying doses of TM. Initially, All TM-treated mice received identical loading doses of 1.2 mg/mouse/day for 3 days (minus 5 to minus 3 days) prior to bleomycin administration. From that point on, groups of mice were given 0.3, 0.5, 0.7, or 0.9 mg of TM/mouse/day until sacrifice at day 21 after bleomycin treatment. A group of four bleomycin treated and a group of four non-bleomycin treated mice received no TM.

A significant protection against the weight loss caused by bleomycin was provided by TM treatment (as shown in FIG. 1). Protection against weight loss from bleomycin by TM is generally related to the dose of TM. The 0.9 mg TM dose is fully protective, with a weight curve similar to saline controls, whereas 0.3 mg TM is only slightly protective. Doses of 0.5 mg and 0.7 mg TM are intermediately protective.

Table 2 shows the effect of varying TM dose on ceruloplasmin levels (data at 8 and 14 days are from single mice; data from 21 days are at the time of sacrifice, and represent the mean and standard error of four mice in each group). At the end of the experiment, all four TM treatment groups show relatively low ceruloplasmin levels. However, at intermediate time points, the 0.9 mg dose shows low levels, the 0.3 mg dose relatively normal levels, and the 0.5 mg and 0.7 mg doses intermediate levels.

Figure 2:
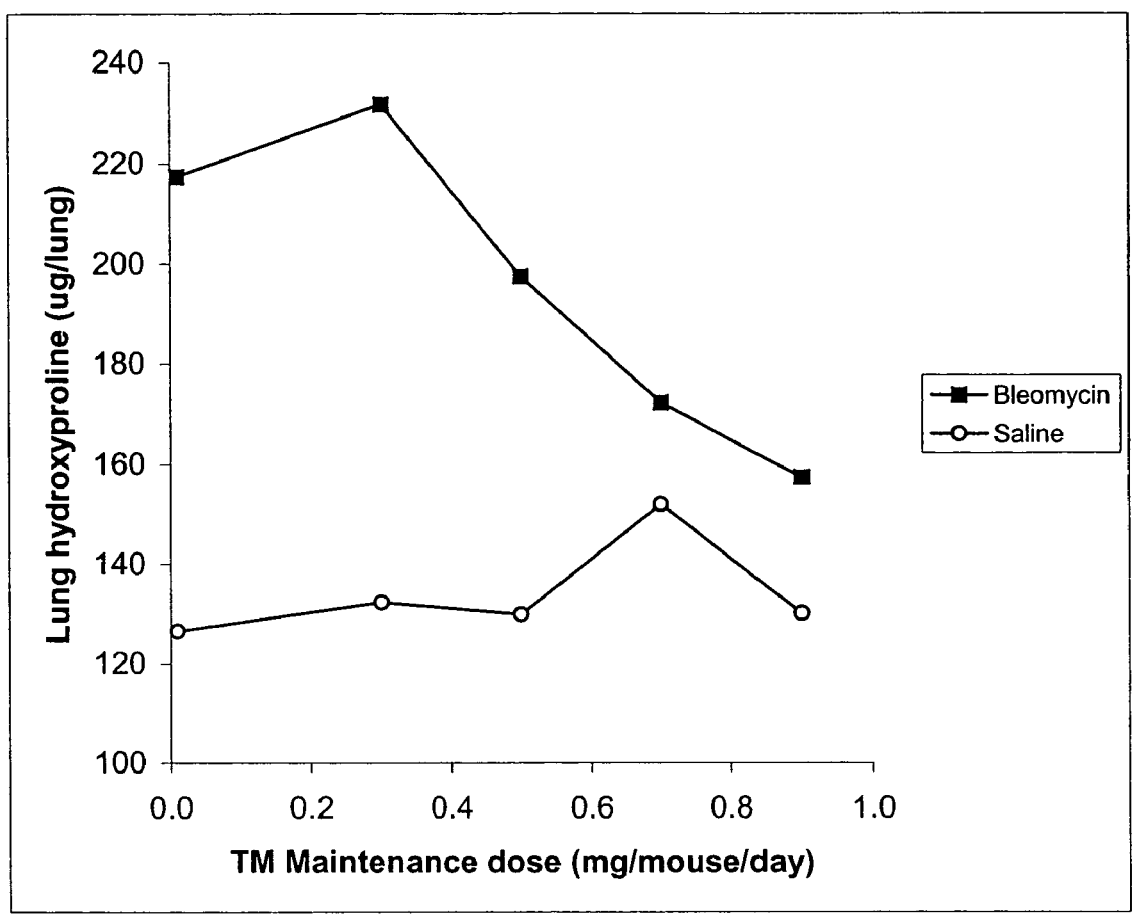
FIG. 2 shows the relationship of excess hydroxyproline (a measure of fibrosis) to TM maintenance dose in experiment 2. The solid squares represent the mean values of 4 mice which received bleomycin and were treated with varying doses of TM, ranging from 0 to 0.9 mg/mouse/day during the maintenance phase of therapy. The open circles represent mice which did not receive bleomycin but received the maintenance doses of TM indicated. Regression of the hydroxyproline data shown in the solid squares in TM doses from 0.3 to 0.9 provided an F statistic of 14.8, with a p value of <0.002.
Figure 3:
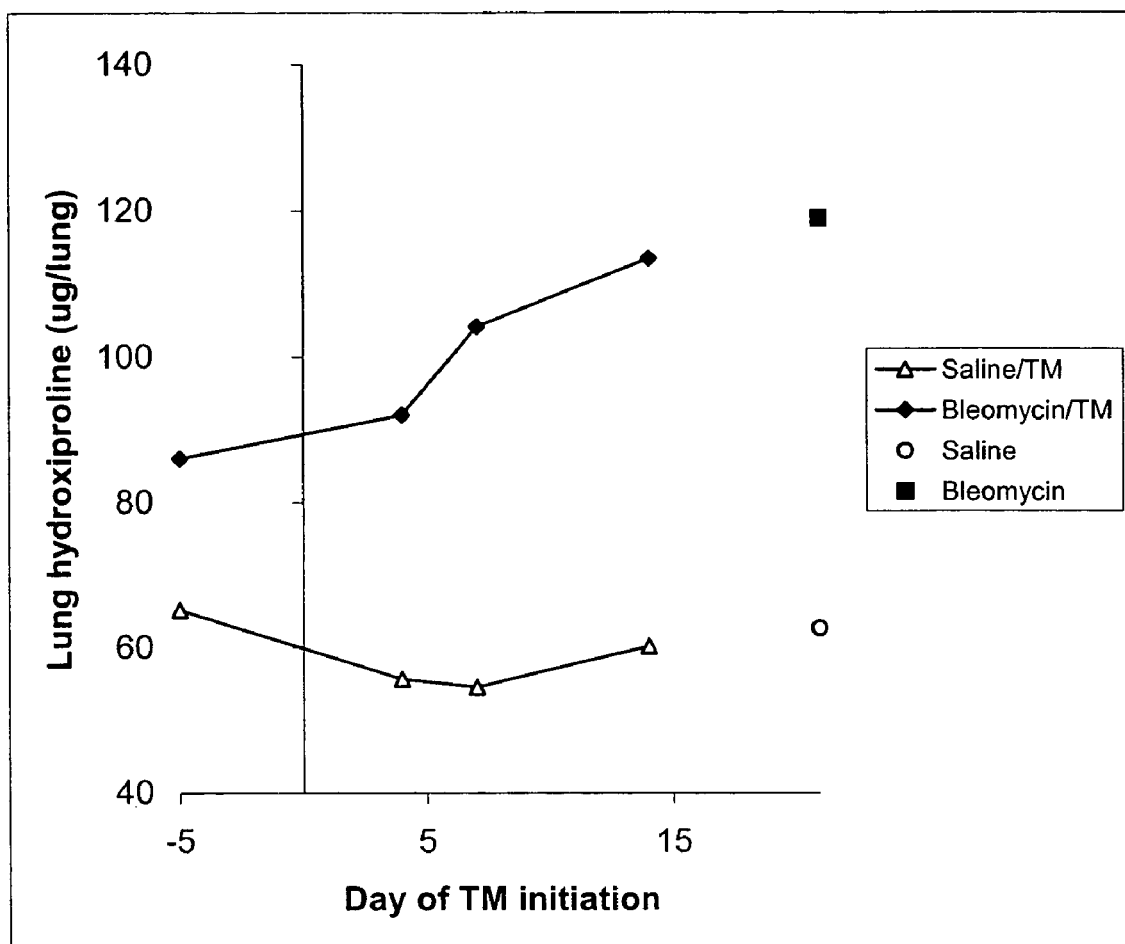
FIG. 3 shows the hydroxyproline results from experiment 3, according to the different starting times of TM therapy. The solid diamonds show the mean hydroxyproline data at sacrifice (day 21) of four mice in each group, except for +day 7, which had five mice, all treated with bleomycin, and all treated with TM at varying starting times as shown in the figure. The solid square represents the mean value of four mice which received bleomycin only, and the open circle the mean of four mice who received saline only. The open triangles represent the means of three to four mice which received no bleomycin but received TM at varying starting times as controls for the bleomycin/TM mice. Regression of the four data points shown by the solid diamonds yielded a significant F statistic (p<0.05). The data from the bleomycin/TM groups at days +4 and +7 were pooled and the mean compared to the bleomycin mean by t test and found to be significantly different (p=0.05).

Finally, the protection against bleomycin-induced fibrosis as measured by hydroxyproline accumulation is dose dependent, as shown in Table 3 and FIG. 2. Regression of the hydroxyproline mean values against TM doses from 0.3 mg to 0.9 mg TM give a highly significant F statistic (<0.002). Comparison of the individual 0.7 mg and 0.9 mg TM dose means against the bleomycin mean by t test showed both to be significantly different, whereas the 0.5 mg dose was not. In this experiment there was no effect of TM treatment alone on hydroxyproline levels (open circles of FIG. 2). The histopathological evaluation generally reflects the biochemical analysis, with diminution of fibrotic lesion size with increasing dose of TM.

TABLE 2

Ceruloplasmin Values (International Units) of TM-Treated Animals During Experiment 2

| | Days | | |
|---|---|---|---|
| TM Maintenance Dose (mg/day/mouse) | 8* | 14* | 21* |
| | | Ceruloplasmin Values | |
| 0.0 | 20.8 | 30.2 | 22.8 ± 2.8 |
| 0.3 | 20.3 | 23.6 | 5.4 ± 2.7 |
| 0.5 | 14.4 | 10.6 | 4.5 ± 2.7 |
| 0.7 | 12.6 | 15.5 | 4.7 ± 2.2 |
| 0.9 | 0.6 | 3.7 | 1.8 ± 0.7 |

TABLE 3

Lung Hydroxyproline Results of Experiment 2

| | Bleomycin Group | | | | |
|---|---|---|---|---|---|
| | 0 TM | 0.3 TM | 0.5 TM | 0.7 TM | 0.9 TM |
| N | 4 | 4 | 4 | 4 | 4 |
| Hydroxyproline (Mean ± SE) | 217 ± 8 | 232 ± 4 | 197 ± 15 | 172 ± 22 | 157 ± 14 |

| | Control Group (Saline only) | | | | |
|---|---|---|---|---|---|
| | 0 TM | 0.3 TM | 0.5 TM | 0.7 TM | 0.9 TM |
| N | 4 | 2 | 3 | 3 | 2 |
| Hydroxyproline (Mean ± SE) | 126 ± 14 | 132 ± 3 | 130 ± 5 | 152 ± 10 | 130 ± 8 |

Statistical Analysis (t Tests)
(Regression of hydroxy-proline values on TM Dose from 0.3 to 0.9)

F Statistic = 14.8; P < 0.002

| Comparison | t value | p value | p value * |
|---|---|---|---|
| Bleo/0 TM versus Bleo/0.3 TM | 0.71 | 0.485 | 0.970 |
| Bleo/0 TM versus Bleo/0.5 TM | 1.00 | 0.333 | 0.905 |
| Bleo/0 TM versus Bleo/0.7 TM | 2.26 | 0.039 | 0.323 |
| Bleo/0 TM versus Bleo/0.9 TM | 3.01 | 0.009 | 0.110 |
| Saline/0 TM versus Bleo/0.9 TM | 1.72 | 0.098 | |

* p value with Scheffe's correction for multiple comparisons.

Experiment 3

In this experiment, the effect of starting the administration of TM at various times before and after the administration of bleomycin was examined.

All experimental groups of mice treated with TM received a four day loading dose of 1.2 mg/mouse/day, and then 0.9 mg/mouse/day until sacrifice at day 21 after bleomycin 10 treatment. However, the starting time of TM treatment was varied beginning with 5 days prior to bleomycin in the first experimental group, then 4, 7 and 14 days after bleomycin in experimental groups two, three, and four, respectively. All experimental groups contained five mice at the beginning. A control group of five mice received neither bleomycin nor TM.

A significant suppression of hydroxyproline production was observed if the TM was given before bleomycin, or started at day 4 or 7 after bleomycin. Regression of mean hydroxyproline levels on the day therapy was started gave an F statistic of 21, $p<0.05$. Since the number of animals in each group was relatively small, the groups +day 4 and +day 7 were combined, and the mean compared to the bleomycin control group, which yielded a significant t test ($p=0.05$). As in experiment 2, there was no effect of TM alone on hydroxyproline levels (open triangles of FIG. 3). These results show that the sooner TM was started, the more effective it was in protecting against hydroxyproline accumulation.

The levels of cytokines, which are believed to be involved in pulmonary fibrosis, are also measured.

In summary, TM treatment completely abrogated fibrosis and markedly attenuated inflammation in a model that is directly relevant to ARDS and pulmonary fibrosis patients.

Example 2

Inhibition of TGFβ, and TNFα by Tetrathiomolybdate in the Bleomycin Model of Pulmonary Fibrosis This example examines the mechanisms by which TM inhibits fibrosis in the bleomycin mouse model. This example, and the experiments described herein, focus on evaluating the possible inhibition by TM of the action of TGFβ, and TNFα, which have been shown to be important in the pathogenesis of fibrosis in the bleomycin model

A. Methods

Mice. Female CBA/J mice at 8-10 weeks old, were from the Jackson Laboratories (Bar Harbor, Me.). At the start of the experiments, the mice weighed between 20-25 g.

Bleomycin treatment. Briefly, bleomycin was administrated on day 0 by means of endotracheal instillation through the oral cavity after exposing the mouse's airway by pulling the tongue. Each mouse received 0.001 units/gm body wt of bleomycin (Bristol-Myers, Evansville, Ind.) in 30 µl sterile saline solution. Control mice were administrated an equal volume of sterile saline solution.

TM treatment experiments. TM was given in 0.25 ml of water once daily by means of intragastric gavage in the doses and times indicated in the various studies.

Three experiments were carried out. Experiment 1 comprised four groups of three mice each. Group 1 received bleomycin only, group 2 received bleomycin and TM therapy, group 3 received saline in the trachea rather than bleomycin, and group 4 received TM therapy only. The mice in groups 2 and 4 each received 1.2 mg of TM per day for four days prior to bleomycin, and then were given 0.9 mg TM per day until sacrifice at seven days after bleomycin.

Experiment 2 comprised four groups of five mice each. The four groups were assigned as in experiment 1 to bleomycin, bleomycin and TM, saline rather than bleomycin, and TM only. Groups 2 and 4 were started on TM five days after bleomycin treatment at a dose of 1.2 mg per day for four days, and then 0.9 mg per day until sacrifice at day 21.

Experiment 3 involved variable starting times of TM and comprised five groups of mice. All of the mice received bleomycin. Group 1 (4 mice) received no TM. Mice in groups 2 through 5 received a 4 day loading dose of 1.2 mg TM/day, then 0.9 mg/day until sacrifice at day 21. However, starting times of TM treatment were varied, beginning 5 days before bleomycin in Group 2 (TM−5, 4 mice), then beginning coincident with bleomycin in group 3 (TM+0, 2 mice), beginning 4 days after bleomycin in group 4 (TM+4, 4 mice), and beginning 7 days after bleomycin in group 5 (TM+7, 5 mice).

Copper status. In the presence of TM therapy, copper status cannot be assessed by direct measurement of serum copper because of the accumulation of a tripartite complex of TM, copper, and albumin that turns over slowly, causing the serum copper to be increased even though availability of copper is decreasing. However, it was found that serum ceruloplasmin is a good surrogate marker of copper status because the liver secretes this copper-containing protein into the blood at a rate dependent on copper availability. Copper status was monitored by assaying serum ceruloplasmin on the basis of its oxidase activity in blood from the tail vein. To avoid excessive bleeding, one mouse from each group was bled at each time point; mice were rotated so that different mice were bled. A ceruloplasmin assay was conducted in each mouse when it was killed.

Hydroxyproline assay. The extent of fibrosis was assessed by assaying hydroxyproline content of whole-lung homogenates at the time of sacrifice as described in Gharaee-Kermani, et al., J. Leukoc. Biol., 64:657-666 (1998). Hydroxyproline was expressed as micrograms of hydroxyproline per mouse lung (the lung tissue included both lungs).

Cytokine assays. Expression of TNFα and TGFβ was determined in lung tissues from the various experiments. TNFα mRNA was measured in total RNA isolated from lung tissue homogenates. Primer Express 2.0 software (Applied Biosystems, Foster City, Calif.) was used to design Taqman primers and MGB probes (6-FAM conjugated) for TNFα, which were then purchased from Applied Biosystems (PE/ABI, Foster City, Calif.). Primers and probes for GAPDH were purchased from PE/ABI. GAPDH mRNA was used as internal control to normalize the amount of input RNA. One-step real time RT-PCR was undertaken with Taqman One Step RT-PCR Master Mix (PE/ABI) using a GeneAmp 5700 Sequence Detection System (PE/ABI). Results were expressed as the threshold cycle (CT) at which an increase of reporter fluorescence (ΔRn) can first be detected. The levels of TNFα mRNA were normalized to the internal control GAPDH signals and expressed as $2^{-\Delta\Delta CT}$.

Lung TGFβ levels were measured using either ELISA with a kit from R&D Systems (Minneapolis, Minn.), or using a cell line stably transfected with a plasminogen activator inhibitor-1 (PAI-1) promoter-luciferase construct (M Abe et al., Analytical Biochemistry, 216:276-284 [1994]). Briefly for the latter assay, mink lung epithelial cells transfected with the PAI-1 promoter construct were incubated with the indicated activated (by pre-acidification) test samples diluted (1:2 dilution) in fresh media. After a 24 hr incubation, the cells were lysed with reporter lysis buffer (Promega, Madison, Wis.). Luciferase activity was measured by the luciferase assay system (Promega) and read using a Reporter microplate luminometer (Turner Designs, Sunnyvale, Calif.). Human TGFβ1 (R&D Systems) was used as a standard.

α-Smooth muscle actin assay. De novo appearance of myofibroblasts is a hallmark of active fibrosis, and these cells are known as the primary source of interstitial collagen in pulmonary fibrosis (See e.g., K Zhang et al., Am. J. Pathol, 145:114-125 [1994]). Since α-smooth muscle actin is a marker of myofibroblast differentiation, the level of this protein in lung tissue homogenates was measured by ELISA as before (use same reference above for TGFβ assay by ELISA).

Statistical analysis. For comparisons of means, Fisher's t test was used and analysis of variance, followed by Scheffe's test for multiple comparisons when appropriate. For varying starting times for TM (Experiment 3), regression analysis was also used to evaluate statistical significance.

B. Results

Experiment 1

In this experiment, TM was started in TM treated animals four days prior to bleomycin and continued until the animals were sacrificed at day 7, the point at which TNFα levels and the inflammatory response is at its peak.

At the time of sacrifice, mean Cp levels in TM treated groups were approximately half of the means in the non-TM treated groups, and using Scheffe's corrections for multiple comparisons were significantly lower in the TM treated groups ($p<0.001$). This indicates that the copper status in TM treated animals was lowered appropriately. The mean hematocrit levels in the four groups at the time of sacrifice were generally similar, with the value in the bleomycin group slightly higher than the others, generally attributable to the bleomycin group drinking less as they begin to get ill. In keeping with this, the mean weight of the bleomycin group was 2-3 g less than the means of the other three groups, and was significantly less in all three cases, using Scheffe's correction ($p=0.001$ to $0.04$). The mean weight in the bleomycin/TM group was almost exactly the same as the saline control group demonstrating that TM protected against this aspect of the bleomycin-induced illness.

Figure 5:
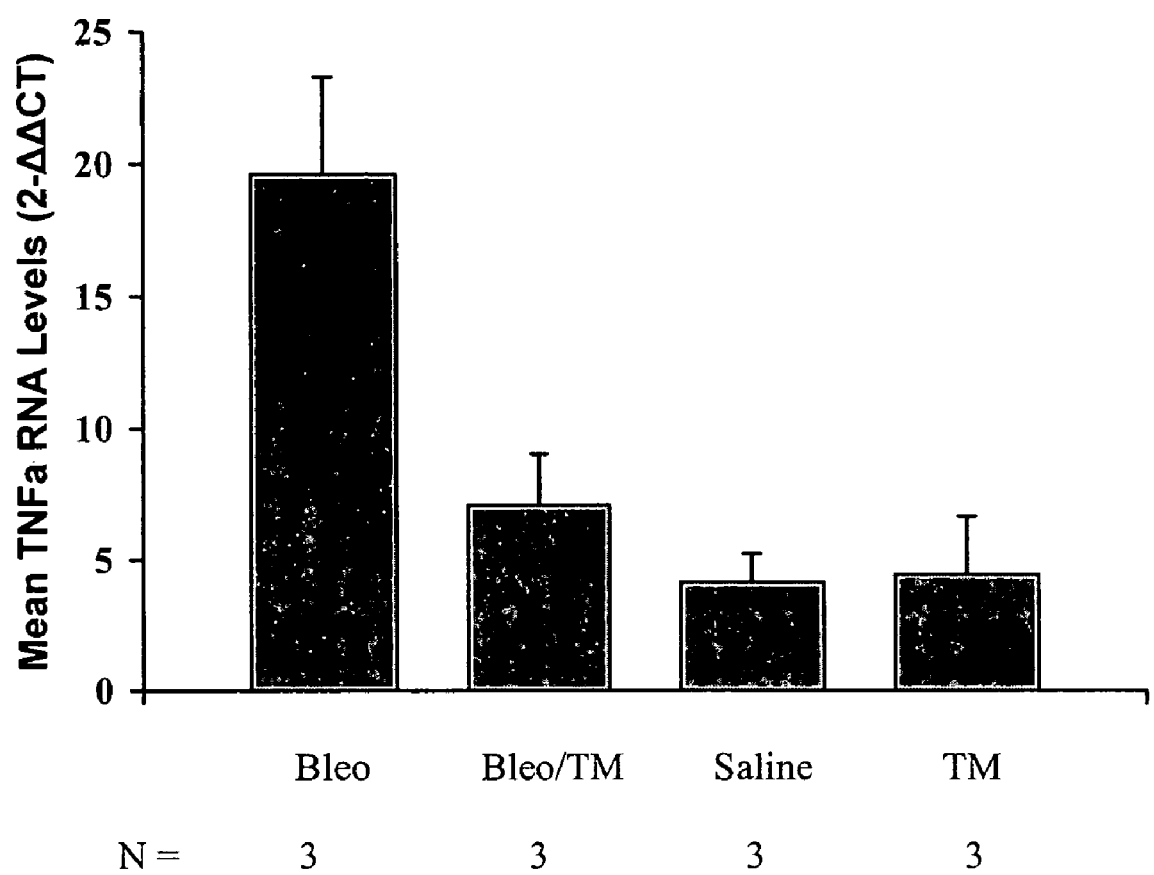
FIG. 5 shows mean TNFα RNA levels in the lungs of the four groups of mice of Experiment 1. Results are shown as the threshold cycle (CT) at which an increase of reporter fluorescence (ΔRn) can first be detected. Amounts of TNFα mRNA were normalized to GAPDH signals and expressed as $2^{-\Delta\Delta CT}$. Statistical evaluation using Scheffé's correction for multiple comparisons reveal that bleomycin versus bleomycin/TM (p<0.04), bleomycin versus saline (p<0.02) and bleomycin versus TM (p<0.02) are all significantly different. Bleomycin/TM versus saline is not significantly different.

TNFα mRNA levels in the lungs from the four groups of animals of Experiment 1 are shown in FIG. 5. The mean lung TNFα mRNA levels were markedly and significantly elevated in bleomycin treated animals versus controls. TM therapy in bleomycin treated animals almost completely, and significantly, inhibited this increase in levels. TNFα protein levels were not detectable in any of the samples by ELISA using commercially available kits.

Figure 6:
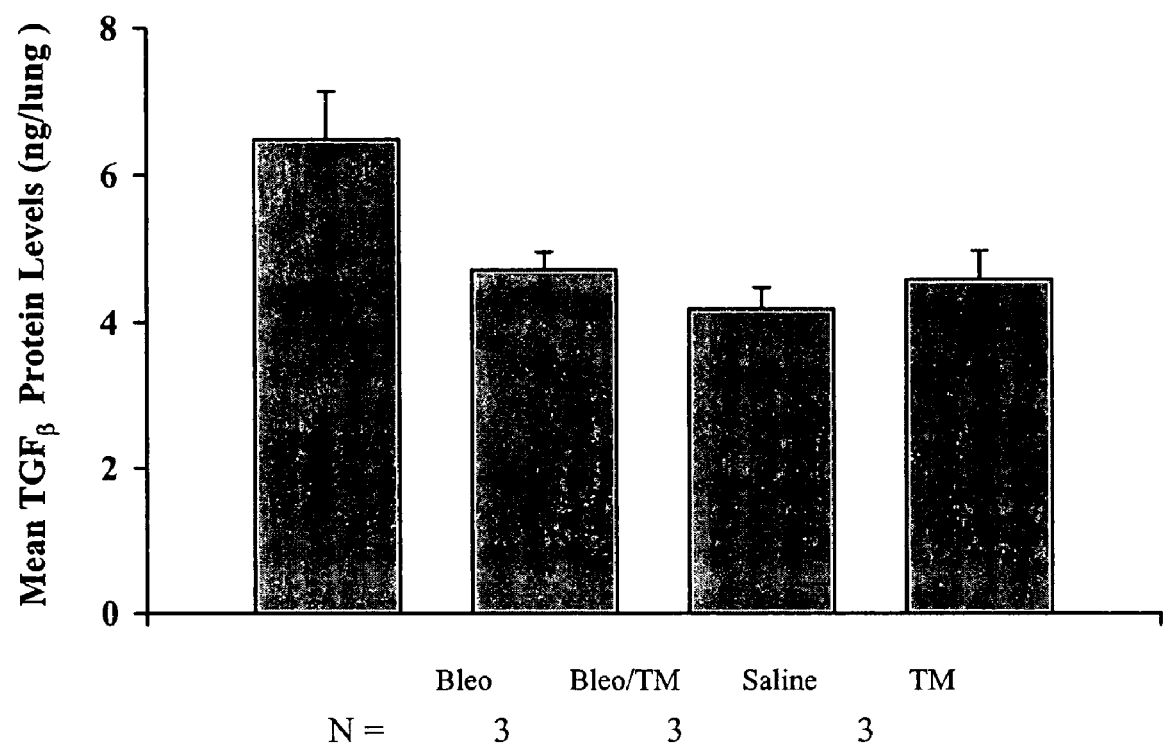
FIG. 6 shows mean $TGF_\beta$ protein levels in the lungs of four groups of mice from Experiment 1. Lung TGFβ protein levels were assayed by ELISA, and the results were expressed as ng/lung.

TGFβ protein levels in the lungs of the four groups of animals of Experiment 1 are shown in FIG. 6. The mean lung $TGF_\beta$ level was elevated in bleomycin treated animals compared to controls. TM therapy in bleomycin treated animals inhibited this increase in response to bleomycin, and the mean levels in bleomycin versus bleomycin/TM were very close to statistical significance ($p=0.06$).

Lysyl oxidase in the lungs of the four groups of animals was also measured. There were no significant differences in the means of the four groups. Specifically, activity was not inhibited in the TM treated animals compared to non-TM treated animals.

Experiment 2

In this experiment TM was started in TM treated animals five days after bleomycin and continued until day 21, when all animals were sacrificed. The objective was to allow the inflammatory reaction to peak, which occurs at about day seven, prior to copper levels dropping into the target range, which is about four days after TM is started, or day nine of this experiment. Then, at the time of sacrifice, TGFβ was to be measured to test whether it is inhibited by TM therapy when the inflammatory reaction is allowed to occur.

At the time of sacrifice, mean Cp levels in the bleomycin/TM group was 38% of the mean of the bleomycin group and the two means were significantly different using Scheffe's correction ($p<0.0001$). Similarly, the mean Cp of the TM control group was 50% of the mean of the saline control group, and the two means were significantly different using Scheffe's correction ($p<0.0001$). Thus, the copper status of the TM treated animal was appropriately lowered by TM therapy. The mean hematocrit of the bleomycin group was 51% versus 44.3 in the bleomycin/TM, 44.2 in the saline, and 43.8 in the TM groups. The mean of the bleomycin group was significantly different than the means of the other three groups using Scheffe's correction ($p=0.0001$ to $0.0002$). The higher hematocrit in the bleomycin group is generally attributable to the bleomycin group drinking less as they become ill, and TM completely protected against this effect of bleomycin. In keeping with this, the mean weight of the bleomycin group at the time of sacrifice was 19.1 g, significantly less than the mean of the saline control which was 24.5 ($p<0.0002$). However, in contrast to earlier experiments where TM completely protected against this weight loss (e.g. Experiment 1 and studies in reference 20), in this experiment TM only slightly protected against weight loss, the mean in the bleomycin/TM group being 19.6, significantly lower than either the saline or the TM control groups ($p=0.0003$ to $0.006$).

Figure 7:
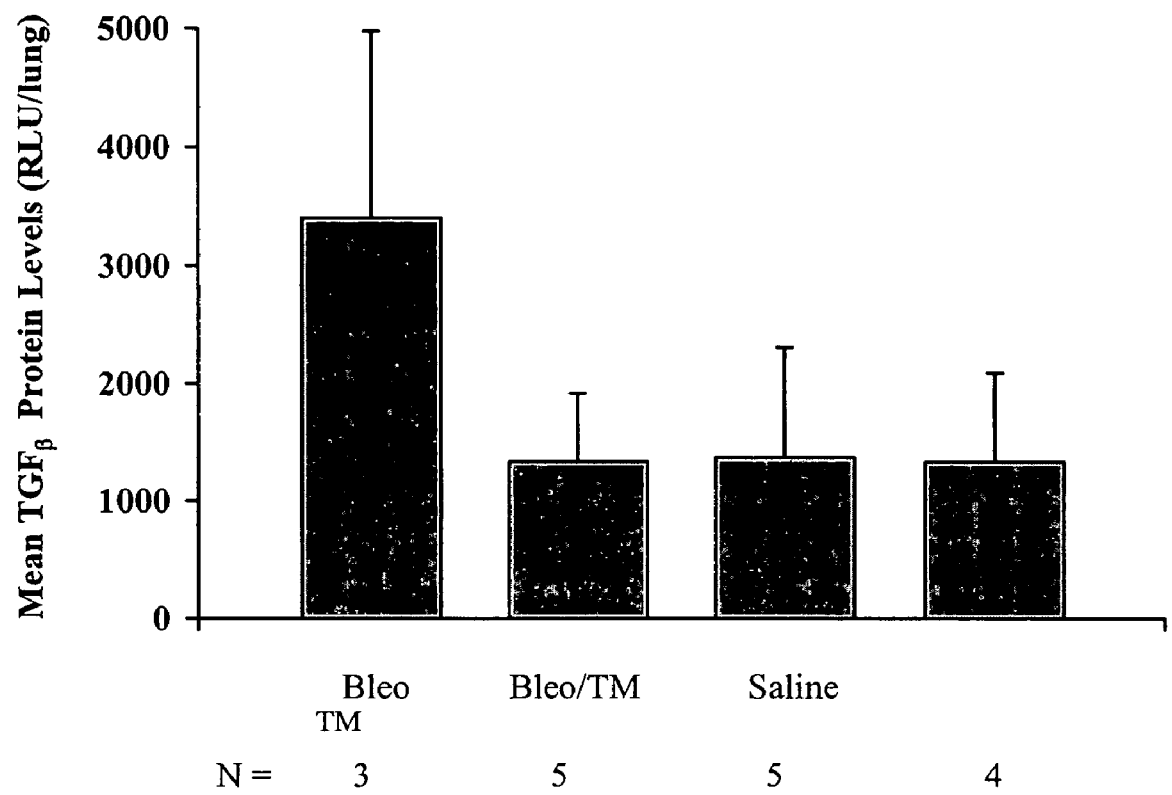
FIG. 7 shows mean $TGF_{62}$ protein levels in the lungs of the four groups of mice of Experiment 2. Lung TGFβ protein levels were measured using the cell line transfected with the PAI-1 promoter-luciferase construct. Results were expressed as relative light units ("RLU")/lung.

TGFβ protein levels in the lungs from the four groups of animals of Experiment 2 are shown in FIG. 7. The mean $TGF_\beta$ levels were almost three times as high in bleomycin treated animals compared to controls. TM therapy in bleomycin-treated animals completely inhibited this increase in $TGF_\beta$ levels, but because of relatively high variances and small sample sizes, the results were not statistically significant.

Figure 8:
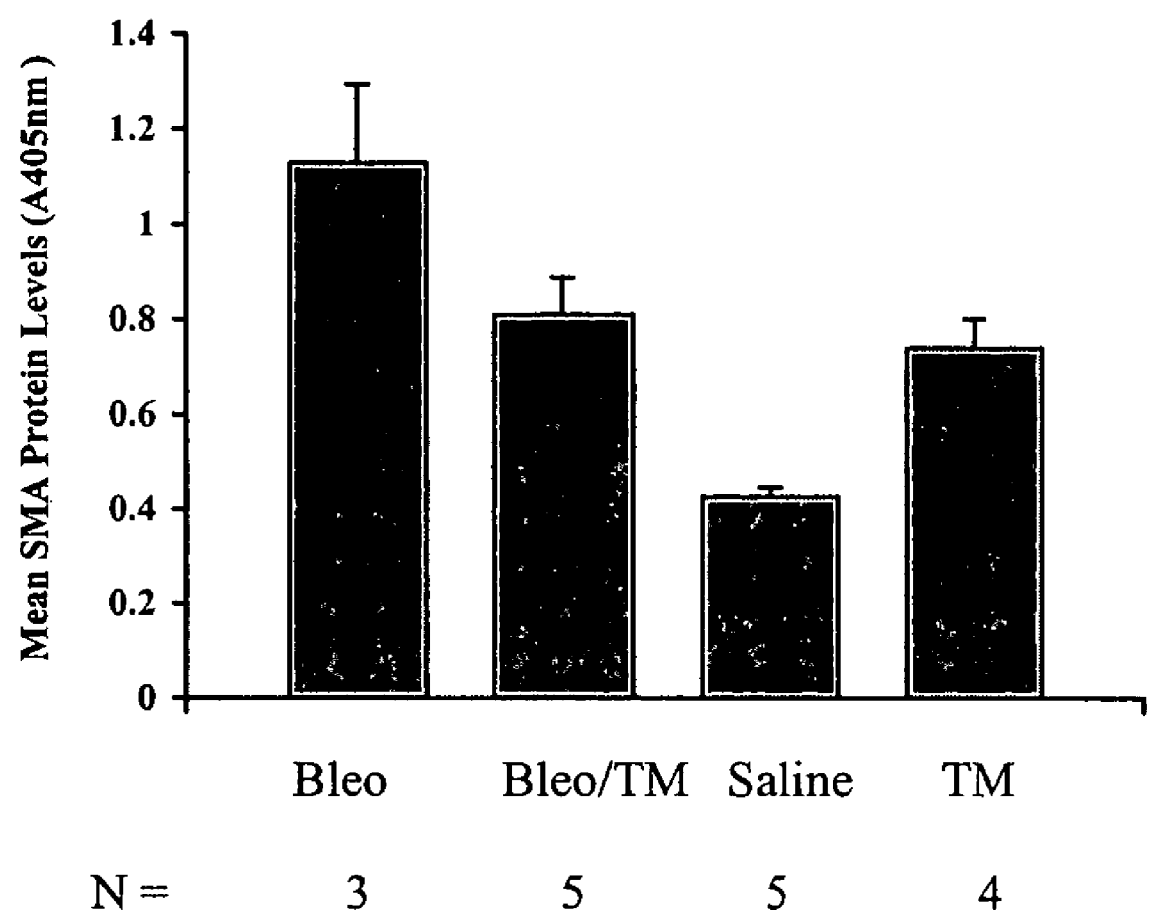
FIG. 8 shows mean SMA levels in the lungs of the four groups of mice of Experiment 2. Lung α-smooth muscle actin protein levels were measured by ELISA, and the results were expressed as the absorbance at 405 nm.

SMA (α-smooth muscle actin) protein levels in the lungs from the four groups of animals of Experiment 2 are shown in FIG. 8. The mean SMA levels were significantly increased in bleomycin treated animals compared to saline-treated controls. TM therapy in bleomycin-treated animals inhibited most of the increase in SMA levels brought about by bleomycin, and was close to statistical significance ($p=0.09$).

Figure 9:
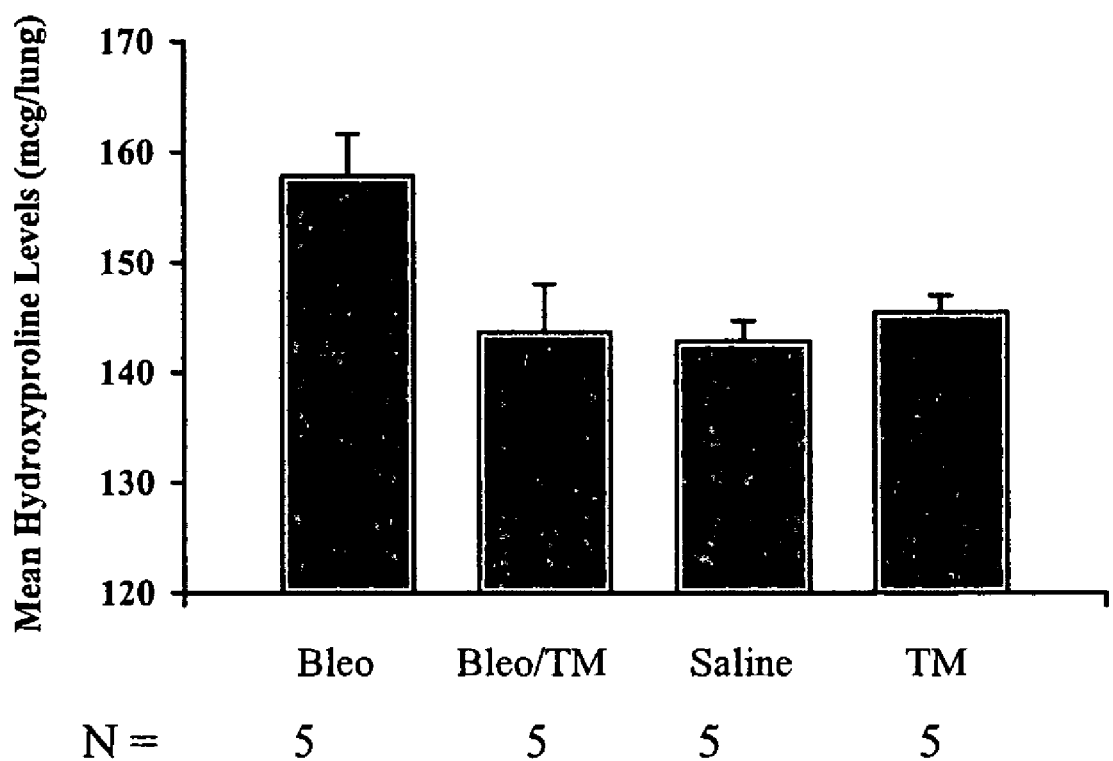
FIG. 9 shows mean hydroxyproline levels in the lungs of the four groups of mice of Experiment 2. Results are expressed as μg/lung. Statistical evaluation using Scheffé's correction for multiple comparisons reveal that bleomycin versus bleomycin/TM (p<0.04), bleomycin versus saline (p<0.02) and bleomycin versus TM (p<0.02) are all significantly different. Bleomycin/TM versus saline is not significantly different.

Hydroxyproline levels in the lungs from the four groups of animals of Experiment 2 are shown in FIG. 9. The mean hydroxyproline levels were significantly elevated in bleomycin-treated animals compared to controls. TM therapy in bleomycin-treated animals completely and significantly inhibited the increase in hydroxyproline levels brought about by bleomycin.

Experiment 3

Figure 10:
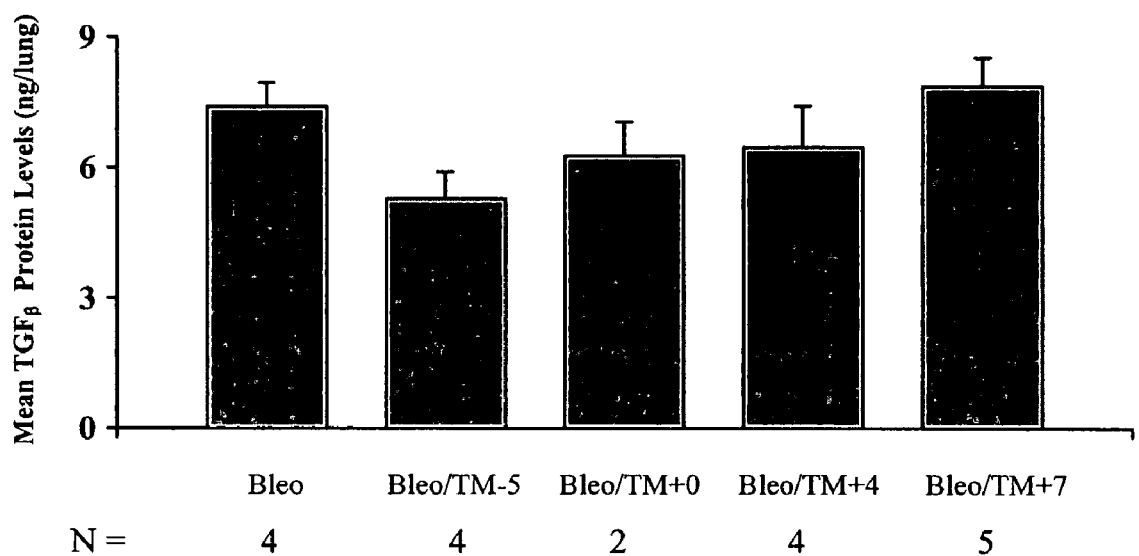
FIG. 10 shows mean $TGF_{62}$ protein levels in the lungs of the five groups of mice of Experiment 3. Lung homogenates were analyzed for TGFβ protein using an ELISA kit, and the results were expressed as ng/lung. The bleomycin mean was significantly different from the mean of the bleomycin/TM-5 group by t test (p=0.04). Regression of the $TGF_\beta$ protein levels on starting time of TM in the four TM treated groups revealed a significant F value (p=0.05).

In this experiment the starting time of TM therapy was varied. The mean TGFβ protein levels in the lungs of the animals from this experiment are shown in FIG. 10. TM started prior to bleomycin (Bleo/TM-5) significantly inhibited TGFβ levels when the means were compared (Bleo/TM-5 versus Bleo, $p=0.04$). This effect lessened as the starting time of TM therapy was made later and later, producing a significant regression for Bleo/TM-5, Bleo/TM+0, Bleo/TM+4, and Bleo/TM+7 data points ($p=0.05$).

Example 3

Treatment of Chronic Pulmonary Fibrosis Clinical Trial (Treatment Protocol)

A protocol is designed to treat patients with chronic pulmonary fibrosis. The initial protocol is a phase I/II trial of TM treatment in patients with usual interstitial pneumonia refractory to previous therapy.

Idiopathic interstitial pneumonias (IIP) are part of a group a diffuse parenchymal diseases including usual interstitial pneumonia (UIP/IPF), respiratory bronchiolitis interstitial lung disease, cryptogenic organizing pneumonia, alveolar macrophage pneumonia, acute interstitial pneumonia, lymphocytic interstitial pneumonia and nonspecific interstitial pneumonia. Usual interstitial pneumonia (also referred to as idiopathic pulmonary fibrosis, IPF) is the most common type of IIP and is associated with the worst prognosis. The median survival for patients with (UIP) is 2-4 years from the time of diagnosis. UIP typically affects people 40 and 70 years of age with over two-thirds being over the age of 60 at the time of diagnosis. There does not appear to be a specific predilection for a particular ethnicity or race although IPF may be more common in males.

Recent studies in the bleomycin mouse model have shown an antifibrotic and antiinflammatory effect of TM therapy (as described in Example 1). As described above, TM is an anticopper drug developed for the treatment of Wilson's disease. TM has also been shown to produce an antiangiogenic effect in non-Wilson's disease patients with cancer, and in animal tumor models, by virtue of lowering systemic copper levels. Angiogenesis, the ability to grow new blood vessels, is believed to be one component required for the progression of the fibrotic response that is typical of IPF. Thus, the rationale for a trial of TM in this disease is based upon its successful use in the bleomycin mouse model, and its antifibrotic and anti-inflammatory properties, as well as its antiangiogenic properties.

Up to twenty patients with UIP that have demonstrated disease progression with standard therapy are enrolled in the study during the first year. The patients initially receive TM as an induction dose to induce a reduction of ceruloplasmin (Cp) levels; after induction of ceruloplasmin (Cp) to the target range of 5-15 mg/dl of serum, the patients then receive maintenance TM doses to maintain that Cp target. Continued treatment of the patients occurs until one of several events occurs: serious further progression of the pulmonary disease; recovery; or disease stabilization for an extended period of time.

A. Protocol for Patient Selection

Only patients with UIP/IPF not associated with any known precipitating cause are eligible for this study. Patients with suspected unsual interstitial pneumonia (UIP) are eligible for initial entry into the study. The criteria for diagnosis are illustrated in FIG. 1 and Tables 4-6. In general, the diagnosis will be considered in the setting of one of the following: 1) an appropriate clinical picture plus a typical histologic picture on surgical lung biopsy as described in Table 4; or 2) an appropriate clinical and radiographic picture with bronchoscopic exclusion of an alternative process as described in Table 5.

In addition to fulfilling either criteria 1 or 2 above, patients should meet the inclusion/exclusion requirements listed in Table 6. Table 7 provides Criteria for disease progression after at least six months of standard therapy considered in some embodiments of the present invention.

TABLE 4

Histologic features of UIP

Pertinent positive features:

Remodeling of lung architecture with dense fibrosis and frequent 'honeycomb' fibrosis
Fibroblastic foci typically at the edges of dense scars
Patchy involvement and temporal heterogeneity
Distribution which is frequently subpleural, paraseptal and/or bronchovascular Pertinent negative features:

Absence of active lesions typical of other interstitial diseases
Absence of marked interstitial, chronic inflammation
Inconspicuous or absent granulomas
Absence of substantial inorganic dust deposits (except carbon black pigment)
Absence of marked tissue eosinophilia

TABLE 5

Adapted ATS criteria for the diagnosis of UIP in the absence of a surgical lung biopsy Major criteria:
Clinical:

Exclusion of other known cause of ILD including collagen vascular illness, environmental or drug exposure
Roentgenographic:

Diffuse reticulonodular pattern on chest x-ray without adenopathy
HRCT features including:

Bibasilar interstitial and intralobular reticular opacities
Irregular interlobular septal thickening with or without traction bronchiectasis
Subpleural honeycombing in the lower lobes
Limited ground-glass opacity and no pleural abnormalities
Absence of micronodules, peribronchial nodules, consolidation, isolated non-honeycomb cysts(5, 6)
Physiologic:

Reduced total lung capacity and/or diffusion capacity
INCREASED P(A—A)$O_2$ AT REST OR WITH EXERCISE
Morphological:

Transbronchial biopsy or bronchoalveolar lavage excluding alternate diagnosis
Minor criteria:

Age > 50 years
Insidious onset of unexplained dyspnea
Duration of illness for ≧ 3 months
Bibasilar, inspiratory rales The presence of all major criteria and three of the four minor criteria increases the likelihood of an accurate diagnosis of UIP.

TABLE 6

Additional inclusion and exclusion criteria for UIP patients

| Inclusion criteria | Exclusion criteria |
| --- | --- |
| Clinical criteria: | Clinical criteria: |
| Disease progression after at least six months of standard therapy (Table 4) | Significant environmental exposure |
| | Diagnosis of collagen vascular disease |
| Taking < 15 mg prednisone for at least 30 days prior to screening | Evidence of active infection |
| Age 35-80, inclusive | Clinically significant cardiac disease |
| Able to understand a written informed consent and comply with the study protocol | Myocardial infarction, coronary artery bypass or angioplasty within 6 months |
| | Unstable angina pectoris |
| | Congestive heart failure requiring hospitalization within 6 months |
| | Uncontrolled arrhythmia |
| | Poorly controlled or severe diabetes mellitus |
| | Pregnancy or lactation |
| | Women of childbearing potential not using a medically approved means of contraception (i.e. oral contraceptives, intrauterine devices, diaphragm, Norplant ®) |
| | Prior treatment with cytotoxic drugs within 6 weeks |
| | Investigational therapy within 6 months of screening |
| | Therapy with zileuton within 6 months of screening |
| | Physiologic criteria: |
| | $FEV_1/FVC < 0.60$ |
| | Laboratory criteria: |
| | Total bilirubin > 1.5 × upper limit normal |
| | AST or ALT > 3 × upper limit normal |
| | Alkaline phosphatase > 3 × upper limit normal |
| | White blood cell count < 2,500/mm$^3$ |
| | Hematocrit < 30% |
| | Platelets < 100,000/mm$^3$ |
| | PROTHROMBIN TIME INR > 1.5 |

TABLE 7

Criteria for disease progression after at least six months of standard therapy

| Standard Therapy: | Disease Progression (any one of the following): |
| --- | --- |
| prednisone: ≧1800 mg administered within a six-month period | Worsening dyspnea at rest or with exertion |
| azathioprine: six month course of therapy | ≧10% decrease in percent predicted FVC |
| cyclophosphamide: six month course of therapy | ≧20% decrease in percent predicted DLCO |
| | Worsening CXR or HRCT |

B. Baseline Studies

All patients undergo a screening history and physical examination. The physician discusses therapeutic options with the patient including standard therapy, experimental protocols, and the potential for consideration of lung transplantation. During this visit the inclusion/exclusion criteria are reviewed.

Flexible fiberoptic bronchoscopy (FFB) is performed in those patients with suspected UIP using standard technique. Bronchoalveolar lavage (BAL) is performed using standard technique (described below) and transbronchial biopsy (TBBx) is performed using fluoroscopic guidance. Tissue is obtained from a radiologically affected region of lung parenchyma. Patients are not asked to undergo a second bronchoscopy if their first bronchoscopy was performed at an outside institution. The purpose of this bronchoscopy is to rule out diseases other than UIP (Table 5) as the tissue samples obtained by bronchoscopy are usually too small to demonstrate the histopathologic features of UIP (Table 4). BAL involves the instillation of small volumes of saline solution through the bronchoscope after it is wedged into a segmental bronchus. The fluid is immediately aspirated back through the bronchoscope by suction and collected in a vacuum trap. The effluent contains cells that are extracted by centrifugation. TBBx involves the passage of a flexible biopsy forceps through the bronchoscope and into the pulmonary parenchyma. The location of the biopsy forceps is noted under fluoroscopy and the biopsy forceps are positioned appropriately in involved areas as determined by chest x-ray and HRCT. Five to eight TBBxs are normally obtained during the course of a diagnostic evaluation for these diseases. Each biopsy specimen is approximately three millimeters in diameter. Only those patients who, in the judgment of the pulmonary physician performing the bronchoscopy, are in stable medical condition following the procurement of the necessary diagnostic biopsies undergo additional transbronchial biopsies.

Surgical lung biopsy specimens are obtained from patients undergoing surgical lung biopsy as part of the diagnostic work up for IIP. Lung biopsies are obtained from sites which demonstrate the following radiographic characteristics: 1) normal appearance, 2) ground glass opacity, and 3) fibrotic disease. When technically feasible, biopsies are obtained from all lobes in the biopsied lung. Patients are not required to undergo a surgical lung biopsy if they can meet the diagnostic criteria (outlined above) for UIP/IPF without a surgical lung biopsy. For patients that have undergone a surgical lung biopsy at another institution, their slides are reviewed to confirm the diagnosis of UIP prior to entry into this trial.

A baseline dyspnea index (BDI) is collected using the techniques described by Mahler et al at the time of initial evaluation. The transitional dyspnea index (TDI) is administered at times of follow-up.

A general measure of the patient's perceived health and daily activities is assessed using Short form 36 question (SF-36) instrument. Multiple dimensions are assessed, including physical function, role limitation caused by physical impairment, bodily pain, general health, vitality, social function, role limitation caused by emotional impairment, and mental health. The use of this instrument has been validated in patients with interstitial lung disease.

The St. George's Respiratory Questionnaire (SGRQ) disease specific instrument was designed to assess the impact of respiratory disease on overall health, daily life and perceived well-being of the patient. It has been validated in patients with interstitial lung disease. Three components are measured including respiratory symptoms, impairment of mobility or physical activity, and the psychosocial impact of disease.

Pulmonary function testing is performed according to the guidelines of the American Thoracic Society. The forced vital capacity (FVC) and the forced expiratory volume in one second are measured with a recording spirometer and pneumotachograph. The maximal values from three maneuvers are reported. Thoracic gas volume ($V_{TG}$) is measured with a body plethysmograph. Diffusing capacity for carbon monoxide is determined by the single breath method.

A baseline high resolution computed tomography (HRCT scan is performed within six months of beginning the study. A semiquantitative score is generated by two blinded radiologists who interpret the HRCT using the scoring system enumerated in Table 8. The score is reported with an alveolar component which describes the extent of 'ground glass opacity' (ranging from 0 to 5) and an interstitial component which describes reticular densities (ranging from 0 to 5). The sum is the total score (ranging from 0 to 10).

TABLE 8

Components of the HRCT Score

| Alveolar Score | |
|---|---|
| 0 | no alveolar disease |
| 1 | ground glass opacity involving < 5% of the lobe (minimal, but not normal) |
| 2 | ground glass opacity involving up to 25% of the lobe |
| 3 | ground glass opacity involving 25-49% of the lobe |
| 4 | ground glass opacity involving 50-75% of the lobe |
| 5 | ground glass opacity involving > 75% of the lobe |
| Interstitial Score | |
| 0 | no interstitial disease |
| 1 | thick interlobular septal thickening; no discrete honeycombing |
| 2 | honeycombing (+/− septal thickening) involving up to 25% of the lobe |
| 3 | honeycombing (+/− septal thickening) involving 25-49% of the lobe |
| 4 | honeycombing (+/− septal thickening) involving 50-75% of the lobe |
| 5 | honeycombing (+/− septal thickening) involving > 75% of the lobe |

*In addition to the scores above, each lobe will be scored for the presence/absence of bronchietasis. The number of lymph nodes >1 cm and <1 cm will be recorded.

C. Administration of Study Drug

The current cancer therapy induction dose for TM is 40 mg 3×daily with meals and 60 mg at bedtime separated from food (180 mg/day). At this dose, it takes 15-25 days to induce cancer patients into the Cp target range. This same induction dose is used for IPF patients. All patients remain on their induction doses until they reach target Cp levels, then are switched to maintenance therapy.

1. Maintenance

As soon as patients reach target Cp levels, their TM dose is be dropped to that dose estimated to be required for maintaining Cp in the target range. Generally, this dose is 20 mg×2 with meals and 20 mg HS, but the dose for any particular patient is customized up or down if necessary. In the absence of unacceptable toxicity, patients are kept on maintenance TM until it is obvious that the disease is seriously progressing, or while improving until recovery is complete, or if the disease persists in a chronic but stable form (see study endpoints below).

2. Monitoring TM Dose

There are two important types of measurements in terms of monitoring and adjusting TM dose. The first is measurement of serum ceruloplasmin (Cp). The Cp level is a surrogate measure of body copper status and has worked well in all kinds of applications of TM therapy, including treating patients with cancer. During induction, Cp is measured weekly. Once a stable maintenance dose of TM is underway, the frequency of Cp measurements are decreased to once every two weeks, then once every four weeks if appropriate.

The other type of measurement necessary to monitor TM therapy is blood counts. The first indication of overtreatment is a mild anemia and/or leukopenia, which is easily correctable by lowering the dose, or if more severe, by temporarily stopping the drug. This is rarely seen at Cp levels over 10, but is more frequently seen between Cp levels of 5 and 10, and is much more common at Cp levels below 5. Thus, the target range is Cp levels between 5 and 15 (to give copper-lowering therapy an optimal chance to suppress fibrosis and inflammation). Weekly blood counts are done during induction and the early part of maintenance to help guide the proper therapeutic dose. During the latter part of maintenance, blood counts are done at the same frequency as Cp assays. If there is a mild, replicable, but less than 20% drop of hemoglobin, WBC, or platelets, the TM dose is decreased based on clinical judgment. If there is a 20% or more drop in hemoglobin, WBC, or platelets, the drug is temporarily stopped until count recovery, and then resumed at 75% (or less) of the previous dose. If there is a recurrence, the drug holiday is repeated and resumed at 75% of that previous dose. Dosage adjustments are continued until a dose is reached at which blood counts are not affected.

3. Studies Performed at Visit wo (Three Months)

At this visit, a history and physical are performed. Patients are asked to complete the transitional dyspnea index, the SF-36, and the St. George's respiratory questionnaire. Pulmonary function studies, including a spirometry and diffusing capacity for carbon monoxide, are performed. Follow-up pulmonary function testing is standard clinical practice in patients with UIP.

4. Studies Performed at Visit Three (Six Months)

At this visit, a history and physical are performed. Patients are asked to complete the transitional dyspnea index, the SF-36, and the St. George's respiratory questionnaire. Pulmonary function studies including a spirometry, diffusing capacity for carbon monoxide, and a six minute hall walk, are performed. Follow-up pulmonary function testing is standard clinical practice in patients with UIP.

5. Studies Performed at Visit Four (Nine Months)

At this visit, a history and physical are performed. Patients are asked to complete the transitional dyspnea index, the SF-36, and the St. George's respiratory questionnaire. Pulmonary function studies, including a spirometry and diffusing capacity for carbon monoxide, are performed. Follow-up pulmonary function testing is standard clinical practice in patients with UIP.

6. Studies Performed at Visit Five (Twelve Months)

At this visit, a history and physical are performed. Patients are asked to complete the transitional dyspnea index, the SF-36, and the St. George's respiratory questionnaire. Pulmonary function studies, including a spirometry and diffusing capacity for carbon monoxide, are performed. Follow-up pulmonary function testing is standard clinical practice in patients with UIP. A follow up HRCT is also performed to evaluate for changes in the amount of ground glass and/or fibrosis.

7. Study Endpoints

The primary endpoint of the study is a change in pulmonary function, where a change in pulmonary function is defined as either: 1) improvement: defined as a 10% or greater increase in FVC or a 20% or greater increase in DLCO; or 2) worsening: defined as a 10% or greater decrease in FVC or a 20% or greater decrease in DLCO; or 3) stable: defined as the lack of a 10% change in FVC or a 20% change in DLCO.

Pulmonary function is monitored at three month intervals. For patients with improvement, TM treatment is continued until pulmonary function stabilizes (lack of improvement in FVC or DLCO of 5% over a 3 month period). Once these improved patients stabilize, TM is discontinued for a 3 month period to determine that stopping the drug does not jeopardize recovery. If these improved patients decline, then TM treatment is restarted. Patients remaining stable are treated for 12 months, and then the drug is stopped and pulmonary function is reassessed at three months. If these stable patients remain stable off drug, the drug is permanently discontinued. If these stable patients decline, then TM treatment is reinstituted. Patients worsening on two consecutive visits with at least 3 months of having Cp in a therapeutic range are taken off TM.

Secondary endpoints of the study include: 1) overall mortality; 2) changes in quality of life (as assessed by the St. George's respiratory questionnaire and the SF-36); 3) change in dyspnea as assessed by the baseline and transitional dyspnea indexes; 4) change in six-minute walk distance; 5) change in oxygen requirements at rest and with exercise as determined via a six-minute walk test; and 6) change in the amount of ground glass and/or fibrosis as measured by HRCT. Criteria for stopping administration of the study drug include but are not limited to: 1) patients mortality or reaching a primary end-point as outlined above; and 2) any unexpected toxicity potentially attributable to the study drug (i.e., TM).

Example 4

Treatment of Liver Cirrhosis: Animal Model

A study was carried out in a mouse model of concanavilin A (Con A) production of liver cirrhosis. There were four experimental groups of several mice each. Two groups received ConA, of which one group also received TM therapy (4 mice) and while the other group received saline therapy (6 mice), and two other groups did not receive ConA, of which one group also received TM therapy (3 mice), while the other group received saline therapy (6 mice). The Con A was injected intravenously once weekly into mice (0.3 mg/mouse/week), and produced a hepatitis, which is manifested by an increasing level of alanine transaminase (ALT) enzymes in the blood. The TM was given once daily by oral lavage in a dose of 0.7 mg/mouse/day beginning 7 days prior to ConA treatment. During days 9 to 11 after Con A, the TM-treated mice received 1.2 mg of TM daily, to ensure adequate lowering of copper levels, and then received 0.7 mg daily for the duration of the study. A blood sample was obtained 28 days after ConA treatment, and the mice were sacrificed on the same day. Serum alanine transaminase (ALT) was measured in Sigma-Frankel (SF) units, where one unit is the formation of 0.000482 umoles of glutamate/minute at pH 7.5 and 25 °C.

TM therapy almost completely inhibits the ConA induced increase of serum alanine transaminase (ALT) enzymes (as shown in FIG. 4). The ALT results indicated that TM treatment completely abrogated inflammation in a model that is directly relevant to hepatitis. Histological examination showed inflammation and early bridging fibrosis in the controls, but not in the TM treated animals.

Example 5

Treatment of Liver Cirrhosis: Animal Model

This example describes additional TM treatment experiments in the model Concanavalin (Con A) mouse model of liver damage. As described previously, in the Con A mouse model, intravenously administered Con A produces an inflammatory reaction and cell damage in the animal's liver that is marked by the release hepatic transaminase enzymes, such as amino leucine amino transferase (ALT), into the blood. Several different experiments are reported in this example Experiment 1

Four serial injections of Con A at weekly intervals were given to the four groups of mice shown in the Table 9. Twenty-four hours after each of the first three injections, one mouse from each group was bled, and serum ALT measured. In this experiment, TM was started in the TM treated mice before the first Con A injection. After the fourth injection of Con A, all the mice were bled for ALT and Cp measurements and the experiment terminated. The Cp levels in TM treated mice were 25-50% of non-TM treated animals. The ALT results (Table 9) show that after each injection, there is a marked increase 24 hours later in serum ALT due to Con A, and that this effect is almost completely blocked by TM therapy. (Statistical evaluation (t test with Scheffe's correction); means marked "1" are significantly different (p=0.0001); means marked "2" are significantly different (p=0.001); means marked "3" are not significantly different (p=0.4); ALT levels are expressed in Sigma-Frankel units; each Sigma-Frankel unit equal 0.48 of an International Unit).

TABLE 9

Serum ALT Results in Mice 24 Hours After Each of Four Weekly Serial Injections of Con A

| | Injection Number | | | | | |
| --- | --- | --- | --- | --- | --- | --- |
| | | | | | 4th | |
| Animal Type | 1st | 2nd | 3rd | n | Mean | S.D. |
| Saline Control | 35 | 44 | 57 | 6 | $41^{1,3}$ | 5.2 |
| TM only control | 85 | 39 | 49 | 3 | 38 | 6.2 |
| Con A only | 179 | 265 | 361 | 6 | $168^{1,2}$ | 47.9 |
| Con A + TM | 52 | 50 | 63 | 4 | $74^{2,3}$ | 10.6 |

Experiment 2

Figure 11:
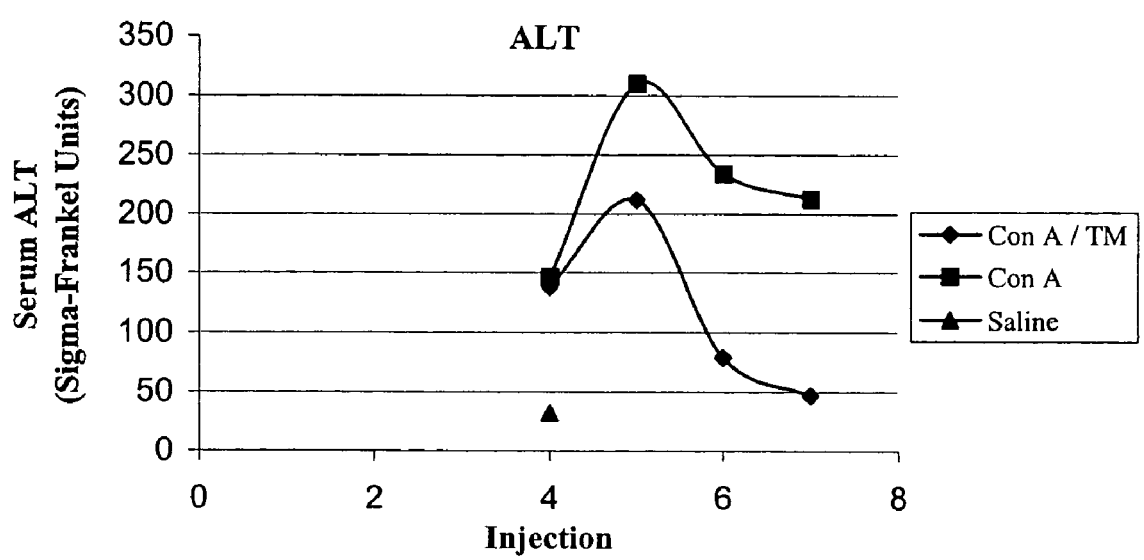
FIG. 11 shows the results of an experiment wherein Con A given for four weeks prior to initiation of TM in an animal model.

In a second experiment, Con A was given in weekly injections for four weeks, prior to any treatment with TM. The objective was to see if TM treatment would be useful after considerable organ damage had been allowed to occur. Then, one group of Con A treated animals were initiated on TM therapy. The results are shown in FIG. 11. With TM treatment, the ALT values returned to normal, in spite of continued Con A injections.

Experiment 3

In a third experiment, two Con A injections one week apart were given to 10 mice. Five of the mice had begun TM treatment 5 days prior to the first injection. All the mice were sacrificed 2 hrs after the last Con A injection. Plasma levels of TNFα were significantly lower (p=0.03) in the TM treated animals, and plasma levels of IL-1β (interleukin-1β, another inflammatory cytokine) were close to being significantly lower (p=0.15) in the TM treated group.

Example 6

TM in the Carbon Tetrachloride (CT) Animal Model of Liver Damage

The carbon tetrachloride (CT) mouse model produces much more liver fibrosis (cirrhosis) than the Con A model. In this model carbon tetrachloride is injected intraperitoneally twice weekly, and after 12 weeks, a well-established cirrhosis should be present. This can be evaluated histologically, and can be quantitated by measuring liver hydroxyproline, a major amino acid in collagen. The TM was started in TM treated animals at the beginning of week 5 and the animals were sacrificed at week 12.

Figure 12:
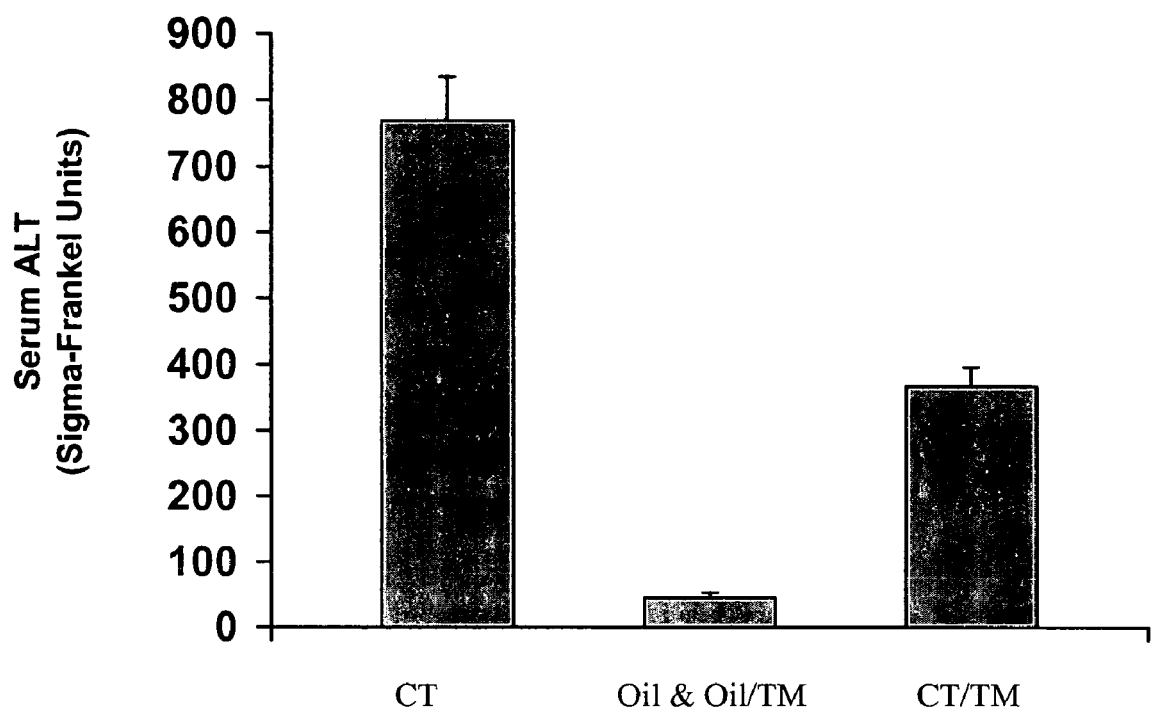
FIG. 12 shows serum ALT data at week 12 in the CT mouse model of liver damage.

The serum ALT data from this experiment at the time of sacrifice at 12 weeks are shown in FIG. 12. There were 4 animals in the CT group, 4 in the CT/TM group, 2 in the olive oil/TM group, and 1 in the TM group. Since there were so few animals in the last two groups, and since their data were generally similar, they were combined. The mean of the CT/TM group was significantly lower (p<0.0008) than that of the CT group showing significant protection against liver injury by TM. However, the CT/TM group mean was significantly higher than the control mean (p<0.004) showing that the protection was only partial.

Figure 13:
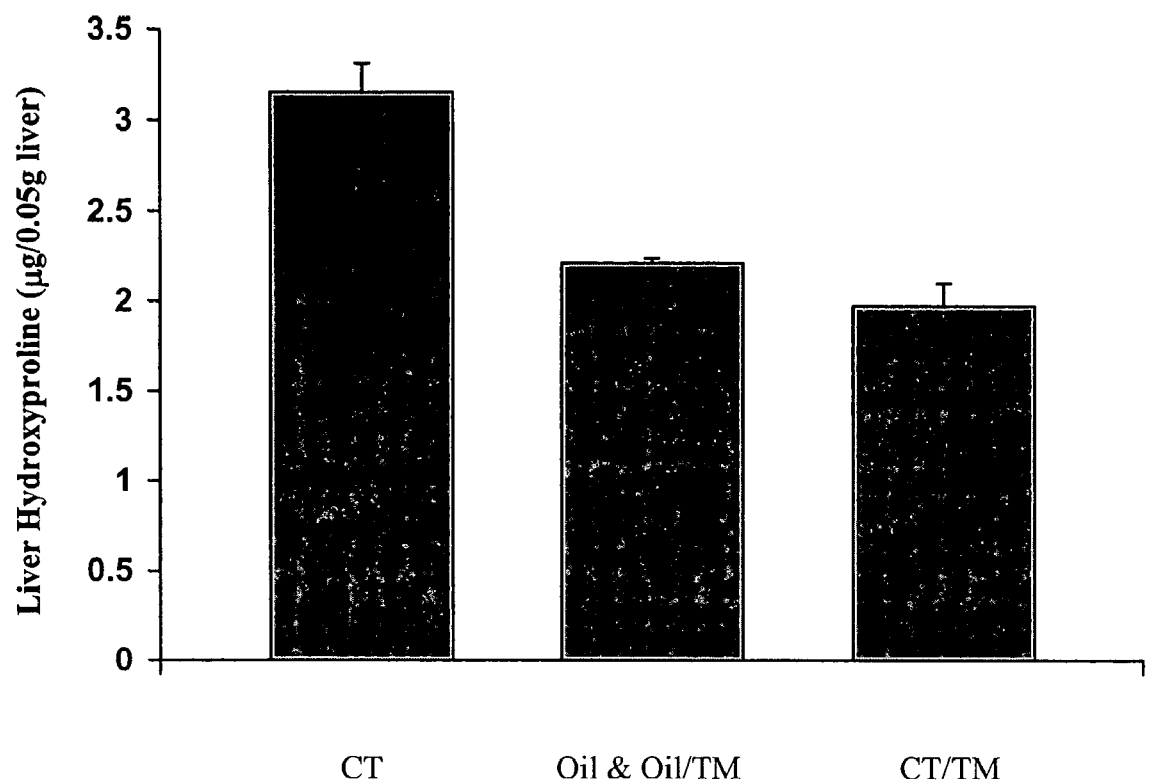
FIG. 13 shows the hydroxyproline content of 0.05g of liver. Column 2 shows the hydroxyproline level in control liver, column 1 shows the effect of CT, and column 3 shows the protection of TM against fibrosis from CT.

The liver hydroxyproline data from this experiment after week 12 are shown in FIG. 13. TM clearly blocks all fibrosis, as evaluated by hydroxyproline. The CT/TM mean was significantly (p=0.001) lower than the CT mean, and there was no difference between the CT/TM and control means. This is corroborated by the histological data. The CT control has a well established cirrhosis whereas the CT/TM treated liver is essentially normal.

Example 7

Treatment of Renal Fibrosis: Animal Model

A study is carried out in an animal model of renal fibrosis. After kidney injury of almost any type, a diffuse interstitial fibrosis (believed to be due to over-activity of the $TGF_\beta$ pathway) produces kidney failure.

Rats are made diabetic by administering streptozotocin; renal fibrosis is typically well developed by 60 days after initiation of streptozotocin administration. TM therapy is initiated at varying times relative to streptozotocin administration in several groups of rats, and the results compared to control groups not receiving TM. Typically, at least three mice are present in each experimental group. In one group, TM therapy is initiated prior to streptozotocin administration, to determine whether TM therapy mitigates the pancreatic damage, as it mitigates hepatitis/cirrhosis in the concanavilin A mouse model described above. In other groups, TM is started after streptozotocin administration, at various times, to determine if it can mitigate the renal fibrosis that develops after streptozotocin administration.

The presence and extent of renal fibrosis is determined. The results show that TM therapy mitigates pancreatic damage if administered before diabetes is induced, and that TM therapy after diabetes is induced mitigates the renal fibrosis that develops as a result of the diabetes.

Example 8

Treatment of Alzheimer's Disease: Animal Model

A study is carried out in an mouse model of Alzheimer's disease. The mouse model is the Tg2576 mouse model, as described above in the Description of the Invention and in further detail in Gau et al., 2002 (J Gau et al., Amer. J. Pathology, 160(2):731-738 [2002]; J Q Trojanowski, Amer. J. Pathology, 160(2):409-411 [2002]). These mice begin developing amyloid plaques at about 9 months of age and plaques are well developed by 15 months. The transgenic mice also develop progressive age-dependent cognitive and behavioral abnormalities described in the background.

A. Overview of Study Design

Forty female Tg2576 mice, aged 3 months, are purchased from Tagonic Inc, and grown until 9 months of age, at which time they are divided into two groups of 20. One group begins treatment with TM at 9 months of age, and are treated until sacrifice at age 15 months. TM treatment consists of daily gavage of 0.7 mg TM/mouse in 0.25 ml of sterile water. This dose has been shown to reduce the serum Cp levels (surrogate marker of copper status) into the target range of 25-50% of baseline levels. Once weekly, one mouse from the treatment group and one from the control group are bled from the tail vein, to determine Cp levels, and blood counts. Mice will be rotated so that different mice are bled each week. Cp is determined by an oxidase method. If the Cp levels begin to move out of the target range, TM dose is adjusted accordingly. Control mice receive a daily gavage of 0.25 ml of sterile water only. The weight of the mice is determined weekly. It is contemplated, based upon past experience, that the weight in mice in the Cp target range will match the weight of control mice.

B. Studies at Autopsy

After 6 months of treatment with water or TM, all mice in both groups are sacrificed painlessly, and the brains removed and divided sagitally. The left half is utilized for physiological assays, and is homogenized for measurements of Aβ40 and Aβ42 by ELISA (see below). The right half is utilized for anatomical assays, and is fixed in 4% paraformaldehyde in phosphate buffered saline (PBS), pH 7.4, at 4° C. and processed for paraffin-embedding. Fixed hemi-brains are sectioned coronally at 5-8 μm thickness, and sections processed for hematoxylin and eosin, Bielschowky silver, and Congo Red staining. Analysis of amyloid plaque load in mouse brains is determined by light-microscopic semi-quantitative analysis of brain sections. Subtle effects of treatment are measured by a more rigorous quantitative analysis of amyloid plaques in brain sections to detect a significant difference.

Brain homogenates of left hemi-brains are used for detection of human Aβ40 and Aβ42 by ELISA, as previously described (J Gau J et al., Amer. J. Pathology, 160 2:731-738 [2001]). Homogenates are centrifuged at 7840×g for 5 minutes at 4 ° C. to remove insoluble material. A sandwich ELISA is performed on the supernatants using BAN50 as the capture antibody and either horseradish peroxidase-coupled BA-27 or BC-05 as the detection antibody for Aβ40 or Aβ42, respectively. BAN-50 is a monoclonal antibody specific for Aβ1-10. All samples are measured in triplicate. Standard curves for the ELISA are constructed using pure human Aβ40 and Aβ42 (Bachem). In addition to measurements of Aβ, a commercially available ELISA is used to detect $TGF_\beta$ levels in brain homogenates of the two groups.

C. Statistical Analysis

The results show that a mean reduction in Aβ40 and Aβ42 levels of up to about 50% in brain homogenates of treated compared to untreated Tg2576 mice is observed at about 15 months of age. Assuming equal variation in treated and untreated animals, 20 animals per group are adequate to readily detect a mean reduction of about 50%. The results also show that semi-quantitative analysis of amyloid load in brain sections correlate with reduction of Aβ levels measured by ELISA. Subtle effects of TM treatment on amyloid plaque deposits in brain are measured by a more rigorous quantitative study; this study utilizes equipment available at the University of Michigan imaging core facility. The results also show that a significant reduction in levels of $TGF_\beta$ as measured by ELISA in TM-treated mouse brain homogenates is observed.

Example 9

Treatment of Alzheimer's Disease Clinical Trial (Treatment Protocol)

A protocol is designed to treat patients with Alzheimer's disease. Briefly, 40 patients with mild to moderate dementia (MMSE 10-23) due to probable AD are recruited, where patients have been enrolled and followed for some time in other programs, so that the clinical diagnosis and baseline studies, including neuropsychometric tests, are well established. Patients are randomized to receive placebo or TM, but the pilot study is single-blinded. The results show that TM treatment arrests or retards decline over 12 months compared to the expected cognitive and functional decline in the placebo group. Before and during the clinical trial, currently approved (FDA) cholinesterase inhibitors are withheld, but other medications are typically continued. Inclusion and exclusion criteria routinely used in clinical trials of patients with AD are also utilized in this trial.

An induction dose of 20 mg TM 3×daily will be administered with meals and 60 mg HS (HS means at bedtime) will be administered away from food. When Cp reaches the target range of 10-15 mg/dl (usually in 2-3 weeks), a typical maintenance dose is used of 20 mg 2×daily with meals and 40 mg HS. Cp and blood counts are followed weekly for a time, adjusting the TM dose as necessary to maintain target. After a stable Cp and TM dose are established, Cp and blood counts are followed every 2-4 weeks. The following battery of neuropsychometric tests are carried out at the beginning and end of the treatment 12 months later: MMSE, CDR, and ADAS-Cog. It is contemplated that few drop-outs will occur, since TM is well-tolerated. For statistical purposes, drop-outs will be subject to intention-to-treat analysis.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant art are intended to be within the scope of the following claims.

I claim:

1. A method of treating Alzheimer's disease in a patient, comprising administering to said patient a biologically effective amount of a thiomolybdate.

2. The method of claim 1, wherein said thiomolybdate forms a thiomolybdate-copper-protein complex in said patient.

3. The method of claim 1, wherein said thiomolybdate is tetrathiomolybdate.

4. The method of claim 1, wherein said biologically effective amount of the thiomolybdate is between about 20 mg and about 200 mg.

5. The method of claim 1, wherein administering said thiomolybdate lowers available copper levels.

6. The method of claim 1, wherein administering said first agent lowers serum ceruloplasmin levels.

7. The method of claim 6, wherein said ceruloplasmin levels are lowered to between about 5 to about 15 mg/dl.

8. The method of claim 6, wherein said ceruloplasmin levels are decreased to between 10% to about 90% of the ceruloplasmin level prior to said administering.

9. The method of claim 6, wherein said ceruloplasmin levels are decreased to about 50% of the ceruloplasmin level prior to said administering.

10. A method of treating Alzheimer's disease in a patient, comprising titrating the administration to the patient of an amount of a thiomolybdate so as to maintain the patient's serum ceruloplasmin level at between about 5 to about 15 mg/dl.

11. A method of treating Alzheimer's disease in a patient, comprising administering an induction dose of a thiomolybdate so as to rapidly reduce the patient's serum ceruloplasmin level to about 5 and 15 mg/dl; and subsequently administering a maintenance dose of said thiomolybdate so as to maintain the patient's serum ceruloplasmin level at between about 5 to about 15 mg/dl.

12. A method of treating Alzheimer's disease in a patient, comprising administering to said patient a biologically effective amount of a slow release formulation of a thiomolybdate.

13. The method of claim 12, wherein said thiomolybdate is tetrathiomolybdate.

* * * * *